(12) United States Patent
Bazant et al.

(10) Patent No.: US 7,708,873 B2
(45) Date of Patent: May 4, 2010

(54) INDUCED-CHARGE ELECTRO-OSMOTIC MICROFLUIDIC DEVICES

(75) Inventors: Martin Z. Bazant, Winchester, MA (US); Yuxing Ben, Duncan, OK (US); Jeremy Levitan, Cambridge, MA (US); John-Paul Urbanski, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/700,949

(22) Filed: Feb. 1, 2007

(65) Prior Publication Data
US 2008/0000772 A1   Jan. 3, 2008

Related U.S. Application Data

(60) Provisional application No. 60/764,358, filed on Feb. 2, 2006.

(51) Int. Cl.
G01N 27/447 (2006.01)
G01N 27/453 (2006.01)
A61K 9/22 (2006.01)

(52) U.S. Cl. .................. 204/451; 204/450; 204/600; 204/601; 604/890.1; 604/892.1

(58) Field of Classification Search ......... 204/600–605, 204/450–455; 435/4; 604/890.1, 892.1
See application file for complete search history.

(56) References Cited

U.S. PATENT DOCUMENTS

| | | | |
|---|---|---|---|
| 4,540,403 A * | 9/1985 | Theeuwes ............ 604/85 |
| 4,908,112 A | 3/1990 | Pace et al. |
| 5,092,972 A | 3/1992 | Ghowsi et al. |
| 5,660,703 A | 8/1997 | Dasgupta et al. |
| 6,156,181 A * | 12/2000 | Parce et al. ............ 204/600 |
| 6,379,974 B1 | 4/2002 | Parce et al. |
| 6,394,759 B1 | 5/2002 | Parce et al. |
| 6,447,727 B1 | 9/2002 | Parce et al. |
| 6,465,257 B1 | 10/2002 | Parce et al. |
| 6,508,273 B1 | 1/2003 | Van Den Berg et al. |
| 6,730,204 B2 * | 5/2004 | Mariella, Jr. ............ 204/547 |
| 6,939,032 B2 * | 9/2005 | Cosby et al. ............ 366/114 |
| 7,063,778 B2 | 6/2006 | Mpholo et al. |
| 7,081,189 B2 * | 7/2006 | Squires et al. ............ 204/451 |

(Continued)

FOREIGN PATENT DOCUMENTS

WO   WO 99/67639 A1 * 12/1999

OTHER PUBLICATIONS

Sasaki et al. "Rapid Mixing Based on AC Electroosmosis in Microchannel," from the Proceedings of Micro Total Analysis Systems 2005, pp. 1096-1098.*

(Continued)

*Primary Examiner*—Alex Noguerola
(74) *Attorney, Agent, or Firm*—Pearl Cohen Zedek Latzer, LLP; Mark S. Cohen

(57) ABSTRACT

This invention provides devices and apparatuses comprising the same, for efficient pumping and/or mixing of relatively small volumes of fluid. Such devices utilize nonlinear electrokinetics as a primary mechanism for driving fluid flow. Methods of cellular analysis and high-throughput, multi-step product formation using devices of this invention are described.

64 Claims, 21 Drawing Sheets

U.S. PATENT DOCUMENTS

| | | | |
|---|---|---|---|
| 7,105,382 B2* | 9/2006 | Myers et al. | 438/122 |
| 2003/0016429 A1 | 1/2003 | Ikeda et al. | |
| 2003/0031090 A1* | 2/2003 | Ho et al. | 366/341 |
| 2005/0129526 A1 | 6/2005 | Dukhin et al. | |

OTHER PUBLICATIONS

Ghosal, "Review: Fluid Mechanics of electrosomotic flow and its effect on band broadening in capillary electrophoresis," Electrophoresis 2004, 25, 214-228.*

Dissertation submitted Jul. 2004 at Notre Dame University entitled "Nonlinear Electrokinetic Phenomena in Microfluidic Devices," by Yuxing Ben.*

Ajdari (2000) "Pumping liquids using asymmetric electrode arrays." Physical Review E Rapid Communications vol. 61 No. 1: 45-48.

Ajdari (2002) "Electrokinetic 'ratchet' pumps for microfluids." Applied Physics 75, 271-274.

Bazant, et al (2004) "Induced-Charge Electrokinetic Phenomona: Theory and Microfluidic Applications." Physical Review Letters vol. 92 No. 6: 066101-1-066104.

Brown, et al (2000) "Pumping of water with ac electric fields applied to asymmetric pairs of microelectrodes." Physical Review E vol. 63, 016305-1-016305-8.

Bown, et al (2006) "AC electroosmotic flow in DNA concentrator." Microfluid Nanofluid, vol. 2: 513-523.

Cahill, et al (2004) "Electro-osmotic streaming application of traveling-wave electric fields." Physical Review E vol. 70, 013605-1-013605-8.

Chu, et al (2006) "Nonlinear etectrochemical relaxation around conductors." Physical Review vol. 74 011501-1-011501-25.

Debesset, et al (2004) "An AC electro-osmotic micro-pump for circular chromatographic applications." Lab Chip, 4, 396-400.

Ejsing, et al (2006) "Frequency response in surface-potential driven electro-hydrodynamics" Physical Review E 037302-1-037302-4.

Gonzalez, et al (2000) "Fluid flow induced by non-uniform ac electric fields in electrolytes on microelectrodes." Physical Review E vol. 61 No. 4: 4019-4028.

Gonzalez, et al (2006) "Electrothermal flows generated by alternating and rotating electric fields in Microsystems." J. Fluid. Mech. vol. 564, 415-433.

Green, et al (2000) "Ac electrokinetics: a survey of sub-micrometre particle dynamics." J. Phys. D: Appl. Phys. Physical Review E vol. 33, 632-641.

Green, et al (2000) "Electric field induced fluid flow on microelectrodes: the effect of illumination." J. Phys. D: Appl. Phys. vol. 33, L13-L17.

Green, et al (2000) "Fluid flow induced by non-uniform ac electric fields in electrolytes on microelectrodes." Physical Review E vol. 61 4011-4018.

Green, et al (2002) "Fluid flow induced by nonuniform ac electric fields in electrolytes on microelectrodes. III. Observation of streamlines and numerical simulation." Physical Review E vol. 66, 026305-1-026305-11.

Levitan, et al (2005) "Experimental observation of induced-charge elctro-osmosis around a metal wire in a microchannel." Physiochem. Eng. Aspects. Physical Review E vol. 267: 122-132.

Meinhart, et al (2003) "Measurement of AC Electrokinetic Flows." Biomedical Microdevices, vol. 5, 139-145.

Mpholo, et al (2003) "Low voltage plug flow pumping using anisotropic electrode arrays." Sensors and Actuators, vol. 92: 262-268.

Olesen, et al (2006) "ac electrokinetic micropumps: The effect of geometrical confinement, Faradaic current injection, and nonlinear surface capacitance." Physical Review E , 056313-1-056313-16.

Ramos, et al (2003) "Pumping of liquids with ac voltages applied to asymmetric pairs of microelectrodes." Physical Review E , vol. 67: 056302-1-056302-11.

Ramos, et al (1999) "AC Electric-Field-Induced Fluid Flow in Microelectrodes." Journal of Colloid and Interface Science, vol. 217: 420-422.

Ramos, et al (2005) "Pumping of liquids with traveling-wave electroosmosis." Journal of Applied Physics, vol. 97: 084906-1-084906-8.

Sigurdson, et al (2005) "Electrothermal stirring for heterogeneous immunoassays." Lab Chip, vol. 5: 1366-1373.

Squires, et al (2004) "Induced-charge electro-osmosis." J. Fluid Mech. vol. 509: 217-252.

Squires, et al (2005) "Breaking symmetries in ICEO" Journal of Fluid Mechanis vol. 560, 65-101.

Squires, et al (2004) "Microfluidics: Fluid Physics at the Nanoliter Scale." Department of Applied Physics, California Institute of Technology. 1-50.

Stone, et al (2004) "Engineering Flows in Small Devices: Microfluidics Toward a Lab-on-a-Chip." Annu. Rev. Fluid Mech., vol. 36: 381-411.

Studer, et al (2002) "Fabrication of microfluidic devices for AC electrokinetic fluid pumping." Microelectronic Engineering, vols. 61-62: 915-920.

Studar, et al (2004) "An integrated AC electrokinetic pump in a microfluidic loop for fast and tunable flow control." Analyst, vol. 129: 944-949.

Urbanski, et al (2006) "Fast ac electro-osmotic micropumps with nonplaner electrodes." Applied Physics Letters, vol. 89: 143508-1-143508-3.

Wong, et al (2004) "Electrokinetics in Micro Devices for Biotechnology Applications." Transactions on Mechatronics, vol. 9, No. 2, 366-376.

Wong, et al (2004) "Electrokinetic Bioprocessor for Concentrating Cells and Molecules." Anal. Chem. 76, 6908-6914.

Wu, et al (2005) "Particle detection by electrical impedance spectroscopy with asymmetric polarization AC electroosmotic trapping," Microfluid Nanofluid, vol. 1: 161-167.

Wu, et al (2006) "Biased AC Electro-Osmosis for On-Chip Bioparticle Processing." Transactions on Mechatronics, vol. 5, No. 2, 84-89.

Squires, et al (2005) "Microfluidics: Fluid Physics at the Nanoliter Scale." Department of Reviews of Modern Pysics vol. 7:3 pp. 977-1026.

Bazant, et al (2006) "Theoretical prediction of Fast 3D AC electro-osmotic pumps." Lab Chip, 6, 1455-1461.

* cited by examiner

INDUCED-CHARGE ELECTRO-OSMOTIC MICROFLUIDIC DEVICES

CROSS REFERENCE TO RELATED APPLICATIONS

This application claims the benefit of U.S. Provisional Application Ser. No. 60/764,358, filed Feb. 2, 2006, which is hereby incorporated by reference in its entirety.

GOVERNMENT SUPPORT

This invention was produced with Government support under Grant Number DAAD-19-02-D -0002US awarded by the Army Research Office. The government has certain rights in the invention.

FIELD OF THE INVENTION

The invention relates to the fields of microfluidics, micro-total-analysis systems (μTAS) and micro-electro-mechanical systems (MEMS), in particular microfluidic pumps and mixers driven by induced-charge electro-osmosis.

BACKGROUND OF THE INVENTION

The ability to transport fluids in micron-sized channels is essential for many emerging technologies, such as in vivo drug delivery devices, micro-electro-mechanical systems (MEMS), and micro-total-analysis systems (μTAS). New methods for the rapid mixing of non-homogeneous fluids in micron-scale devices are also required, since the absence of turbulent mixing on these small length scales implies that mixing occurs by molecular diffusion alone. This typically takes from seconds to minutes—far too slow for envisioned applications. New technologies are thus required for the manipulation, transport and mixing of fluids on these small length scales.

Microfluidics is a growing area of science and technology with important applications in biomedical devices and portable electronics. Traditional pressure-driven flows do not scale well with miniaturization, due to large viscous stresses, so other pumping techniques have been explored. An attractive alternative is electro-osmosis, the effective slip of a liquid electrolyte past a solid surface in response to an applied electric field, since it does not involve any moving parts, is unaffected by miniaturization, and integrates well with standard microelectronics and fabrication methods. The standard technique of (capillary) electro-osmosis involves a DC electric field applied down a microchannel made of insulating material to generate a plug flow. The electric field acts on the equilibrium surface charge in the diffuse-part of the double layer, and the resulting electro-osmotic flow is linear in the applied field.

Various methods have been described to alter the surface charge in linear electro-osmosis to allow some degree of local flow control. For example, one method applies "field-effect electro-osmosis" to control capillary electro-osmosis by applying voltages at secondary electrodes just outside the channel surface, to alter the equilibrium surface charge (or "zeta potential") driving steady flow at the insulating channel wall and another controls liquid flow down a traditional insulating capillary by the same effect.

Capillary electro-osmosis, with or without field-effect flow control, however, is not ideal for certain microfluidic applications, since the electric field is applied down the channel, a large voltage is required, e.g. 100 Volts across a 1 cm device to generate typical fields of 100 V/cm. Since electro-osmosis is linear in the applied field, a direct current must be sustained through Faradaic electrochemical reactions at the electrodes generating the field, which can produce gas bubbles, electrode degradation/dissolution, hydrodynamic instability, and sample contamination. Further, the typical fluid velocity is fairly small (e.g. 100 micron/sec for a 100 Volt/cm field) and only increases linearly with the voltage. It would be preferable to drive flows with low-voltage alternating currents in many microfluidic applications, while somehow increasing the flow rate for the same applied field.

Microfluidic devices based on nonlinear electro-osmotic flow have also been developed. For example, nonlinear electro-osmotic flow, varying as the square of the applied voltage, termed "AC electro-osmosis" (ACEO), over a pair of flat, parallel-stripe microelectrodes on a flat insulating surface, has been described.

While existing ACEO pumps operate at much lower power (mA) and lower voltage (Volt) than microfluidic pumps based on linear electro-osmosis, nonetheless, current ACEO devices are somewhat inefficient for long-range pumping, and more general flow topologies for simultaneous mixing and pumping have not been developed.

SUMMARY OF THE INVENTION

In one embodiment, this invention provides a device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%.

In one embodiment, the electric field is comprised of a DC electric field, or in another embodiment, the electric field is comprised of an AC or pulsed AC electric field In another embodiment, the microfluidic channels are comprised of a transparent material, which in one embodiment is a plastic or in another embodiment is a polymer. In one embodiment, the device is comprised of a material, which is transparent at a given wavelength corresponding to excitation and emission of a fluorophor. In one embodiment, the device is comprised of a material, which is transmissive at a certain wavelength, or in some embodiments, at a wavelength that corresponds to excitation/emission of a compound or reagent. In another embodiment, the microfluidic channels and/or devices comprising the same are comprised of a material functionalized via SAM, or in another embodiment, comprising an adhesion layer, as described herein.

In one embodiment, the plurality of electrodes are arranged so as to produce:

electro-osmotic flows with at least one varied trajectory in a region of said chamber, resulting in mixing of said electrolyte fluid;

a dominant electroosmotic flow which drives said electrolyte fluid across said chamber;

or a combination thereof.

In one embodiment, the microfluidic device comprises:

at least two background electrodes connected to said source, providing said electric field in said microchannel; and at least one pumping element comprising two or more parallel-positioned or interdigitated electrodes positioned therebetween; wherein electrodes in said pumping element vary in height with respect to each other, said background electrodes, or a combination thereof.

In one embodiment, the pumping element is held at a fixed potential, relative to that of the background electrodes. In another embodiment, at least one electrode in the pumping element is grounded to one of the background electrodes. In another embodiment, the microchannel comprises multiple background electrodes, multiple pumping units placed therebetween, or a combination thereof.

In another embodiment, each electrode in the pumping unit nearest to the background electrode connected to the source will have an opposite polarity as compared to the background electrode. In another embodiment, an electrode in the pumping unit is connected to the background electrode connected to said source, which is of the same polarity. In another embodiment, the electrodes in the pumping unit are arranged asymmettically with respect to a central axis in the pumping unit. In another embodiment, at least one electrode in the pumping element is positioned on a different vertical plane, than the background electrodes.

In another embodiment, electrodes are parallel-positioned or interdigitated. In another embodiment, at least one electrode of the plurality of electrodes is not flat.

In another embodiment, the plurality of electrodes comprises at least one electrode, or a portion thereof, which is raised with respect to another electrode, or another portion of said at least one electrode.

In another embodiment, the plurality of electrodes comprises at least one electrode, or a portion thereof, which is lowered with respect to another electrode, or another portion of said at least one electrode. In another embodiment, the plurality of electrodes comprises at least one or at least a portion thereof having a height or depth, which is varied proportionally to a width of another electrode, another portion of said at least one electrode, or a combination thereof. In another embodiment, the plurality of electrodes comprises at least one electrode or portions thereof, having height or depth variations from about 1% to about 1000% of:

a width of another electrode, another portion of said at least one electrode, or a combination thereof;

a gap between said at least one electrode and another electrode;

or a combination thereof.

In another embodiment, the electrodes are not co-axial, with respect to each other, in any dimension. In another embodiment, the positioning of the electrodes in the microfluidic channel is varied with respect to gaps between the electrodes, spacing of the electrodes, or a combination thereof. In another embodiment, the electrodes are arranged in a symmetric pattern in said microfluidic channel, and in another embodiment, the gaps between the electrodes, the spacing of the electrodes, or a combination thereof is equal.

In another embodiment, the electrodes are arranged in a asymmetric pattern in the microfluidic channel, and in another embodiment, the gaps between said electrodes, said spacing of said electrodes, height of said electrodes or portions thereof, shapes or said electrodes or portions thereof, or a combination thereof is unequal.

In another embodiment, the electrodes are arranged in a gradient pattern in the microfluidic channel.

In another embodiment, the devices comprise a plurality of electrodes, wherein at least one electrode comprises at least one raised portion of said electrode in the form of a cylinder of arbitrary cross section, or in another embodiment, at least one electrode comprises an edge, which is straight and not parallel to another edge in said electrode or in another electrode, or in another embodiment, the electrode comprises an edge, which forms a chevron or sawtooth pattern, either vertically or horizontally.

In another embodiment, the devices comprise a plurality of electrodes, wherein at least one electrode comprises an edge, which is curved, or in another embodiment, the electrode comprises an edge, which forms a wavy or arc-like pattern, vertically, horizontally, or a combination thereof, or in another embodiment, at least one electrode comprises an exposed surface, which is flat, and not coplanar with another exposed surface of said electrode or of another electrode. In another embodiment, at least one electrode comprises an exposed surface, which is not flat, and arbitrarily curved in three dimensions In another embodiment, the gaps are between about 1 micron and about 50 microns, and in another embodiment, the electrode widths are between about 0.1 microns and about 50 microns.

In another embodiment, the source applies a peak to peak AC voltage of between about 0.1 and about 10 Volts. In another embodiment, the AC frequency is between about 1 Hz and about 100 kHz.

In another embodiment, this invention provides an apparatus comprising a device of this invention.

In another embodiment, this invention provides a method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid.

In another embodiment, this invention provides a method of circulating or conducting a fluid, comprising applying a fluid to a device or an apparatus of this invention.

In another embodiment, this invention provides a method of cellular analysis, comprising the steps of:

a. introducing a buffered suspension comprising cells to a first port of a device;

b. introducing a reagent for cellular analysis to said first or to a second port of said device, said device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electro-osmotic flow is generated, which drives said electrolyte fluid across said chamber, or a combination thereof; and c. analyzing at least one parameter affected by contact between said suspension and said reagent.

In one embodiment, the reagent is an antibody, a nucleic acid, an enzyme, a substrate, a ligand, or a combination thereof. In another embodiment, the reagent is coupled to a detectable marker, which in another embodiment is a fluorescent compound. In another embodiment, the device is coupled to a fluorimeter or fluorescent microscope. In another embodiment, the device is comprised of a transparent material.

In another embodiment, the method further comprises the step of introducing a cellular lysis agent in a port of said device. According to this aspect of the invention, and in one embodiment, the reagent specifically interacts or detects an intracellular compound.

In another embodiment, this invention provides a method of high-throughput, multi-step product formation, the method comprising the steps of:
  a. introducing a first liquid comprising a precursor to a first port of a device;
  b. introducing a second liquid comprising a reagent, catalyst, reactant, cofactor, or combination thereof to said first port, or a second port of said device, said device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, and a product of said precursor is formed in said device; and
  c. collecting said product from said device.

In one embodiment, the method further comprises the step of carrying out iterative introductions of said second liquid, as in (b), to a port of the device. In one embodiment, the reagent is an antibody, a nucleic acid, an enzyme, a substrate, a ligand, a reactant or a combination thereof.

In another embodiment, this invention provides a method of drug processing and delivery, the method comprising the steps of:
  a. introducing a drug and a liquid comprising a buffer, a catalyst, or combination thereof to a device, comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid comprising said drug; a dominant electroosmotic flow is generated, which drives said electrolyte fluid comprising said drug across said chamber, or a combination thereof; and
  b. collecting said drug, delivering said drug to a subject, or a combination thereof.

In one embodiment, the method further comprises carrying out iterative introductions of said second liquid to said inlet ports. In another embodiment, the second liquid serves to dilute the drug to a desired concentration.

In another embodiment, this invention provides a method of analyte detection or assay, comprising the steps of:
  a. introducing a first fluid comprising an analyte to a first port of a microfluidic device;
  b. introducing a second fluid comprising a reagent to said first port or to a second port of said microfluidic device, said microfluidic device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said fluid comprising said analyte and reagent; a dominant electroosmotic flow is generated, which drives said electrolyte fluid comprising said analyte and reagent across said chamber, or a combination thereof; and
  c. detecting, analyzing, or a combination thereof, of said analyte.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
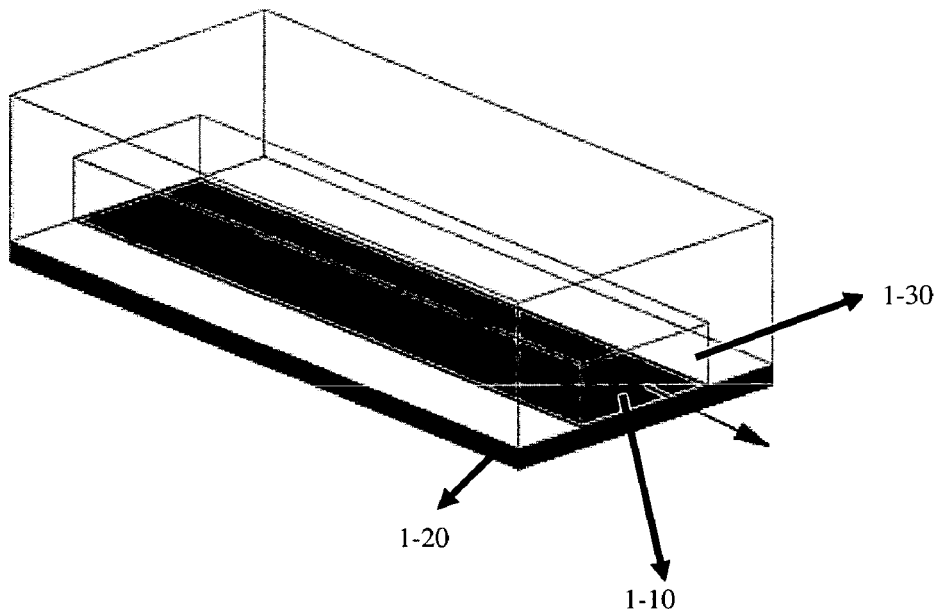
FIG. 1 schematically depicts embodiments of devices of this invention. A. General form of microfluidic channels (1-30) with electrokinetic pumps (shaded region) (1-10) patterned on a substrate (1-20) with a molded-polymer cap. Lighter arrows indicate the direction of pumping. The channel may be straight (A) or may have recessed cavities (1-40) (B). The upper surface or side walls may contain sensing elements or other electrokinetic pumps (C). For example, the upper surface could be identical to the lower, each with a pump, with side walls formed by a separator layer to form the channel.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in some embodiments, devices and apparatuses comprising the same, for the mixing and/or pumping of relatively small volumes of fluid. Such devices utilize nonlinear electrokinetics as a primary mechanism for driving fluid flow.

In one embodiment, this invention makes use of ACEO-based devices which pump and/or mix fluid, by a mechanism which utilizes nonlinear electrokinetic pumps and mixers involving three-dimensional structures in microchannels. The driving principle in these devices is termed "induced-charge electro-osmosis" (ICEO), which, in one embodiment refers to nonlinear (voltage-squared) electro-osmotic flow, which results when an electric field acts on its own induced charge at a polarizable (metal or dielectric) surface.

In one embodiment, this invention provides a device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%.

In one embodiment, this invention provides a device, comprising at least one microfluidic channel, said microfluidic channel comprising:
    a passageway for conducting an electrolyte fluid or circulating an electrolyte fluid, or a combination thereof; and
    a plurality of electrodes positioned on, or comprising a surface of said microfluidic channel, wherein:

at least two of said plurality of electrodes are connected to a source, providing an electric field in said microchannel;

said electrodes are parallel-positioned or interdigitated; and said electrodes or portions thereof are varied in height.

In one embodiment, this invention provides a microfluidic device comprising:

at least one port for fluid entry into, egress from, or a combination thereof said device; and at least one microfluidic channel in fluid communication with said ports, wherein said microfluidic channel comprises:

a passageway for transmitting an electrolyte fluid; and a plurality of electrodes connected to a source, providing an electric field in said microchannel; wherein said electrodes are parallel-positioned or interdigitated and are co-axial, with respect to each other, in at most one dimension, whereby said electric field produces a dominant electro-osmotic flow across said microfluidic channel.

In one embodiment, this invention provides a microfluidic device comprising at least one inlet port, at least one outlet port and at least one microfluidic channel in fluid communication with said ports.

In one embodiment, the microfluidic channel comprises:

a passageway for transmitting an electrolyte fluid;

at least two background electrodes connected to a source, providing an electric field in said microchannel; and at least one pumping element comprising two or more parallel-positioned or interdigitated electrodes, positioned between said at least two electrodes;

wherein said pumping element is positioned co-axially, with respect to said electrodes, in at most one dimension, so that interactions between said field and said pumping element produce electro-osmotic flow.

In one embodiment, the microfluidic device comprises placement of the elements on a substrate, or in another embodiment, the microfluidic chamber is contiguous with the substrate.

In one embodiment, the term "a" refers to at least one, which in some embodiments, is one, or in some embodiments two or more, or in some embodiments, pairs of, or in some embodiments, a series of, or in some embodiments, any multiplicity as desired and applicable for the indicated application.

In one embodiment, the substrate and/or other components of the device can be made from a wide variety of materials including, but not limited to, silicon, silicon dioxide, silicon nitride, glass and fused silica, gallium arsenide, indium phosphide, III-V materials, PDMS, silicone rubber, aluminum, ceramics, polyimide, quartz, plastics, resins and polymers including polymethylmethacrylate (PMMA), acrylics, polyethylene, polyethylene terepthalate, polycarbonate, polystyrene and other styrene copolymers, polypropylene, polytetrafluoroethylene, superalloys, zircaloy?, steel, gold, silver, copper, tungsten, molybdeumn, tantalum, KOVAR, KEVLAR, KAPTON, MYLAR, teflon, brass, sapphire, other plastics, or other flexible plastics (polyimide), ceramics, etc., or a combination thereof.

In some embodiments, the devices will comprise at least one bubble trap or at least one gas permeable membrane proximal to a microfluidic channel, which in turn may facilitate filling of such channel with a fluid as described herein.

The substrate may be ground or processed flat. High quality glasses such as high melting borosilicate or fused silicas may be used, in some embodiments, for their UV transmission properties when any of the sample manipulation and/or detection steps require light based technologies. In addition, as outlined herein, portions of the internal and/or external surfaces of the device may be coated with a variety of coatings as needed, to facilitate the manipulation or detection technique performed, to enhance flow, to promote mixing, or combinations thereof.

In one embodiment, the substrate comprises a metal-bilayer. In some embodiments, such substrates comprise adhesive or bonding layers such as titanium or chrome or other appropriate metal, which is patterned or placed between the electrode surface and another component of the device substrate, for example, between a distal gold electrode and an underlying glass or plastic substrate.

In one embodiment, the metal-bilayer is such that a metal is attached directly to an electrode, which comprises, or is attached to another component of the substrate.

In another embodiment, the substrate comprises an adhesive layer between, for example underlying glass or plastic substrate and an electrode such as a polymer, a monolayer, a multilayer, a metal or a metal oxide, comprising iron, molybdenum, copper, vanadium, tin, tungsten, gold, aluminum, tantalum, niobium, titanium, zirconium, nickel, cobalt, silver, chromium or any combination thereof. In another embodiment the substrate comprises electrodes of zinc, gold, copper, magnesium, silver, aluminum, iron, carbon or metal alloys such as zinc, copper, aluminum, magnesium, which may serve as anodes, and alloys of silver, copper, gold as cathodes.

In another embodiment, the substrate comprises electrode couples including, but not limited to, zinc-copper, magnesium-copper, zinc-silver, zinc-gold, magnesium-gold, aluminum-gold, magnesium-silver, magnesium-gold, aluminum-copper, aluminum-silver, copper-silver, iron-copper, iron-silver, iron-conductive carbon, zinc-conductive carbon, copper-conductive carbon, magnesium-conductive carbon, and aluminum-conductive carbon.

In some embodiments, the substrate may be further coated with a dielectric and/or a self-assembled monolayer (SAM), to provide specific functionality to the surface of the device to which the material is applied.

In one embodiment, the term "chambers" "channels" and/or "microchannels" are interchangeable, and refer to a cavity of any size or geometry, which accommodates at least the indicated components and is suitable for the indicated task and/or application.

comprise the same materials as the substrate, or in another embodiment, are comprised of a suitable material which prevents adhesion to the channels, or in another embodiment, are comprised of a material which promotes adhesion of certain material to the channels, or combinations thereof. In some embodiments, such materials may be deposited according to a desired pattern to facilitate a particular application.

In another embodiment, the substrate and/or microchannels of the devices of this invention comprise a material which is functionalized to minimize, reduce or prevent adherence of materials introduced into the device. For example, in one embodiment, the functionalization comprises coating with extracellular matrix protein/s, amino acids, PEG, or PEG functionalized SAM's or is slightly charged to prevent adhesion of cells or cellular material to the surface. In another embodiment, functionalization comprises treatment of a surface to minimize, reduce or prevent background fluorescence. Such functionalization may comprise, for example, inclusion of anti-quenching materials, as are known in the art. In another embodiment, the functionalization may comprise treatment with specific materials to alter flow properties of the material through the device. In another embodiment, such functionalization may be in discrete regions, randomly, or may entirely functionalize an exposed surface of a device of this invention.

In one embodiment, the invention provides for a microchip comprising the devices of this invention. In one embodiment, the microchip may be made of a wide variety of materials and can be configured in a large number of ways, as described and exemplified herein, in some embodiments and other embodiments will be apparent to one of skill in the art.

The composition of the substrate will depend on a variety of factors, including the techniques used to create the device, the use of the device, the composition of the sample, the molecules to be assayed, the type of analysis conducted following assay, the size of internal structures, the placement of electronic components, etc. In some embodiments, the devices of the invention will be sterilizable as well, in some embodiments, this is not required. In some embodiments, the devices are disposable or, in another embodiment, re-usable.

Microfluidic chips used in the methods and devices of this invention may be fabricated using a variety of techniques, including, but not limited to, hot embossing, such as described in H. Becker, et al., Sensors and Materials, 11, 297, (1999), hereby incorporated by reference, molding of elastomers, such as described in D. C. Duffy, et. al., Anal. Chem., 70, 4974, (1998), hereby incorporated by reference, injection molding, LIGA, soft lithography, silicon fabrication and related thin film processing techniques, as known in the art, photolithography and reactive ion etching techniques, as exemplified herein. In one embodiment, glass etching and diffusion bonding of fused silica substrates may be used to prepare microfluidic chips.

In one embodiment, microfabrication technology, or microtechnology or MEMS, applies the tools and processes of semiconductor fabrication to the formation of, for example, physical structures. Microfabrication technology allows one, in one embodiment, to precisely design features (e.g., reservoirs, wells, channels) with dimensions in the range of <1 µm to several centimeters on chips made, in other embodiments, of silicon, glass, or plastics. Such technology may be used to construct the microchannels of the devices of this invention, in one embodiment.

In one embodiment, fabrication of the device may be accomplished as follows: first, a glass substrate is metallized. The choice of metal can be made with respect to a variety of desired design specifications, including resistance to oxidation, compatibility with biological materials, compatibility with substrates, etc. The metallization layer may be deposited in a specific pattern (i.e. through adhesive or shadow-masked metal evaporation or sputtering), in one embodiment, or, in another embodiment, it may be etched subsequent to deposition. Metals can include, but are not limited to gold, copper, silver, platinum, rhodium, chromium, etc. In some embodiments, the substrate may be coated with an initial layer of a thin metal, which promotes adhesion of another metal to the substrate. In some embodiments, metals may also be adhered to the substrate via adhesive. In some embodiments, the substrate is ground flat to promote adhesion. In some embodiments, the substrate is roughened to promote metal adhesion.

According to this aspect of the invention, and in one embodiment, the deposited metal may either be deposited in the final topology (i.e. through a mask) or, in another embodiment, patterned post-deposition. According to the latter embodiment, a variety of methods may be used to create the final pattern, as will be understood by one skilled in the art, including inter-alia, etching and laser ablation. Mechanical forms of removal (milling, etc.) may be used, in other embodiments.

In one embodiment, gold is deposited on chromium and the gold is etched using a photoresist mask and a wet gold etchant. The chromium remains a uniform film, providing electrical connection for subsequent electrodeposition (forming the anode connection). In another embodiment, gold is deposited via electron-beam evaporation onto an adhesion layer of titanium. The gold is patterned using a wet etchant and photoresist mask. The titanium is left undisturbed for subsequent electrodeposition.

In another embodiment, the metal may be patterned prior to deposition. A shadow mask can be utilized in one embodiment. The desired shape is etched or machined through a thin metal pattern or other substrate. The etched substrate is then held parallel to the base substrate and the material is deposited via evaporation or sputtering through the mask onto the substrate. In some embodiments, this method is desirable in that it reduces the number of etch steps.

In another embodiment, the patterned surface is formed by transferring a pre-etched or stamped metal film with adhesive onto the substrate. In one embodiment, the various devices on the layer have a common electrical connection enabling subsequent electrodeposition, and are deposited strategically so that release and dicing results in proper electrical isolation.

In another embodiment, a rigid stamp is used to puncture a thin metal film on a relatively pliable elastic (plastic) substrate. The rigid stamp can have, in some embodiments sharp or blunt edges.

In some embodiments, the thickness of deposited metals is tailored to specific applications. In one embodiment, thin metal is deposited onto the surface of the wafer and patterned. According to this aspect of the invention, and in one embodiment, the patterned surface forms a common anodic connection for electroplating into a mold.

In one embodiment, molding may be used. In one embodiment, molding comprises a variety of plastics, ceramics, or other material which is dissimilar to the base substrate. In one embodiment, the molding material is removed following electroplating. In some embodiments, the molding material is sacrificial.

In another embodiment, thick (greater than a few microns) metal is deposited and subsequently etched to form raised metal features.

In other embodiments, welding, assembly via SAMs, selective oxidation of thin metals (conversion of, for instance, aluminum to aluminum oxide) comprise some of the methods used to form insulating areas and provide electrical isolation.

In other embodiments, passivation of the metal surfaces with dielectric materials may be conducted, including, but not limited to, spin-on-glass, low temperature oxide deposition, plastics, photoresists, and other sputtered, evaporated, or vapor-deposited insulators.

In some embodiments, the microfluidic channels used in the devices and/or methods of this invention, which convey and/or mix fluid, may be constructed of a material which renders it transparent or semitransparent, in order to image the materials being assayed, or in another embodiment, to ascertain the progress of the assay, etc. In some embodiments, the materials further have low conductivity and high chemical resistance to buffer solutions and/or mild organics. In other embodiments, the material is of a machinable or moldable polymeric material, and may comprise insulators, ceramics, metals or insulator-coated metals. In other embodiments, the channel may be constructed from a polymer material that is resistant to alkaline aqueous solutions and mild organics. In another embodiment, the channel comprises at least one surface which is transparent or semi-transparent, such that, in one embodiment, imaging of the device is possible.

In one embodiment, the inlet, or in another embodiment, the outlet may comprise an area of the substrate in fluidic communication with one or more microfluidic channels, in one embodiment, and/or a sample reservoir, in another embodiment. Inlets and outlets may be fabricated in a wide variety of ways, depending upon, in one embodiment, on the substrate material utilized and/or in another embodiment, the dimensions used. In one embodiment inlets and/or outlets are formed using conventional tubing, which prevents sample leakage, when fluid is applied to the device, under pressure. In one embodiment inlets and/or outlets are formed of a material which withstands application of voltage, even high voltage, to the device. In one embodiment, the inlet may further comprise a means of applying a constant pressure, to generate pressure-driven flow in the device.

In one embodiment, a "device" or "apparatus" of this invention will comprise at least the elements as described herein. In one embodiment, the devices of this invention comprise at least one microchannel, which may be formed as described herein, or via using other microfabrication means known in the art. In one embodiment, the device may comprise a plurality of channels. In some embodiments, the devices of this invention will comprise a plurality of channels, or microchannels. In one embodiment, the phrase "a plurality of channels" refers to more than two channels, or, in another embodiment, channels patterned according to a desired application, which in some embodiments, refers to channels varying by several orders of magnitude, whether on the scale of tens, hundreds, thousands, etc., as will be appreciated by one skilled in the art.

In one embodiment, the devices of this invention comprise pump and/or mix fluids using non-linear electroosmotic flow generated within the device.

In one embodiment, the devices of this invention comprise electrodes connected to a source providing an electric field in the microchannel, wherein the device comprises two or more parallel or interdigitated electrodes, which when in the presence of electrolyte fluids in the device and application of the field produce electro-osmotic flows so that said electrolyte fluid is driven across the microfluidic channels.

In some embodiments, the term "electrode" is to understood to refer to the metal electrode per se, as well as a substrate onto which such an electrode is affixed, or which comprises the electrode, or is proximal to the electrode.

The electrodes of the devices of this invention will have varied height, in some embodiments, or in other embodiments, will not be co-axial, with regard to Cartesian axes, in more than one dimension. It is to be understood that with reference to varied spatial apportionment of the electrodes, e.g. their height, that such reference is in terms of the vertical placement of the electrode, as well as the electrode placed on an underlying substrate. For example, this invention is to be understood to comprise a chamber comprising a pair of electrodes, wherein the electrodes have a comparable width and depth, however one electrodes height may be 10 micron with another being 40 microns, or with another also being 10 microns, however the electrode is positioned on a substrate of 30 microns in height.

It is to be understood that with reference to variance in height, such reference is to be understood to encompass distance normal or orthogonal to the surface on which the electrodes are placed, or in other embodiments, in the direction orthogonal to the mean plane of the surface while, for example, "horizontal" may refer to a direction coplanar with the mean plane of the surface.

In some embodiments, the arrangement of the electrodes is such so as to promote mixing of the materials in the microchannel, as will be appreciated by one skilled in the art, and as exemplified hereinbelow.

In some embodiments, the geometries of the electrodes are varied so as to promote mixing of the fluid in discrete regions of the channel, and/or conveyance of mixed material.

In some embodiments, the device is so constructed so as to promote mixing in certain channels and conveyance to other channels, which in turn may comprise additional steps, which require mixing, as described herein.

In some embodiments, the devices of this invention facilitate deposition of fluids at a site distal to the microchannels, for further processing, or other manipulations of the conveyed material.

In some embodiments, electroosmosis in the devices of this result in the creation of a dominant flow. The term "dominant flow" refers, in some embodiments, to propulsion of fluid in a desired direction (also referred to as "positive direction"), with minimal, or less propulsion of fluid in an undesired direction (also referred to as "negative direction"). In some embodiments, concurrent propulsion in both positive and negative directions may result in drastically reduced overall flow, which occurs with planar electrodes, which are approximately likewise proportioned in at least two of three dimensions, for example, likewise in terms of height and depth, and varied at most in terms of width, in previous ACEO devices. Devices of this invention are likewise proportioned in at most only one of three dimensions, thus varied in terms of height and depth, of an electrode, or portions thereof. Thus, in some embodiments, electrodes in devices of this invention are likewise proportioned in terms of width, likewise proportioned in terms of their depth, however the height of each electrode, or in some embodiments, the height of portions of each electrode, or in some embodiments, the height of pairs of electrodes, or in some embodiments, the height of portions of electrode pairs are varied. In some embodiments, such height alterations may comprise raised or stepped electrode structures, or lowers or recessed electrode structures in a device to provide vertical differences in the electrode structure.

In some embodiments, the terms "height alterations" or "height variance" or other grammatical forms thereof, refer to differences in height, which exceed by at least 1.5%, or in some embodiments, 3%, or in some embodiments, 5%, or in some embodiments, 7.5%, or in some embodiments, 10%, or more the referenced electrode. For example, a planar electrode pair in an array may vary in height by up to 0.25%, as a result, for example, of different deposition of material forming the electrodes on a surface of a channel in the device. In the devices of this invention, in contrast, height variances between at least two electrodes, or electrode pairs, or series in a given device, will be more pronounced, and not a reflection of undesired variance due to material deposition.

In some embodiments, the term "dominant flow" refers to electroosmotic flows, or flows as a result of application of an electric field in a chamber of the devices of this invention. It is to be understood that a dominant flow may be instituted that is less in magnitude, or varied in direction, for example, than other flows in the device, such as other background flows, pressure-driven flows for applying materials to the device, etc.

In some embodiments, the devices of this invention may cause flows for mixing or controlling flow rate (faster/slower/stopping/starting . . . ) in a channel which also has a stronger more "dominant" background flow (e.g. pressure-driven from elsewhere), where the device's dominant effect is still smaller than the background flow, yet is nonetheless greater in magnitude than similar electroosmotic flows would be with the use of planar electrodes. "Dominant" in reference to flows caused by the devices/apparatuses/methods of this invention may be understood, in some embodiments, to specifically exclude background flow, or non-electroosmotic flow.

In some embodiments, the electrodes and metal structures are all "flat" in the sense that the primary exposed surfaces are co-planar and parallel to at least one surface of the channel, although the electrodes may be arranged at different heights and transverse positions in three-dimensional geometries. In other embodiments, the devices comprise periodic arrays of non-flat, three-dimensional electrodes, with raised and lowered sections (on a single electrode).

In another embodiment, at least one electrode of the plurality of electrodes is not flat. In another embodiment, the plurality of electrodes comprises at least one electrode, which is raised with respect to another electrode. In another embodiment, the plurality of electrodes comprises at least one electrode, which is lowered with respect to another electrode. In another embodiment, the plurality of electrodes comprises at least one electrode having a height, which is proportional to a width of another electrode. In another embodiment, the plurality of electrodes comprises at least one electrode having a height, which varies by about 1% to about 100% of a width of another electrode. In another embodiment, the electrodes are not co-axial, with respect to each other, in any dimension. In another embodiment, the positioning of the electrodes in the microfluidic channel is varied with respect to gaps between the electrodes, spacing of the electrodes, or a combination thereof. In another embodiment, the electrodes are arranged in a symmetric pattern in said microfluidic channel, and in another embodiment, the gaps between the electrodes, the spacing of the electrodes, or a combination thereof is equal.

It is to be understood that any variance as described herein with reference to one electrode versus another in the plurality of the devices/apparatuses of this invention is to be taken to refer to portions of electrodes as well, where variance in shape, width, depth, height reflects such variance within a single electrode, in terms of portions of the electrode, different electrodes in the device and any combination thereof.

In another embodiment, the electrodes are arranged in an asymmetric pattern in the microfluidic channel, and in another embodiment, the gaps between the electrodes, the spacing of the electrodes, or a combination thereof is unequal.

In another embodiment, the electrodes are arranged in a gradient pattern in the microfluidic channel.

The term "gradient", in some embodiments, refers to an arrangement which has gradual or gradated differences, for example in electrode height, from one terminus of such arrangement to another, or in some embodiments, gradual or gradated differences, for example in electrode width, gradual or gradated differences, for example in electrode depth, gradual or gradated differences, for example in electrode shape, gradual or gradated differences, for example in electrode circumference, gradual or gradated differences, for example in the angle at which each electrode is deposited in an array in a device of the invention, or gradual or gradated differences, in any combination thereof, or any desired parameter of the same. In some embodiments, the term gradual or gradated differences refers to differences, which are based on a pattern, in ascending or descending value, which may be consecutive or non-consecutive.

In some embodiments, the term "gradient" refers to any of parameter with regard to electrode geometry, which may vary by any defined/desired period, for example incrementally, or as a multiple or exponential scale, in one or more directions. For example, the layout (gaps, widths, heights, etc.) of each pair of electrodes in an interdigitated array could be rescaled to get larger (or smaller) with distance along the array in the direction of pumping so that the local pumping flow is slower (or faster).

In some embodiment, the gradient may be a function of the gaps between electrodes, spacing of electrodes, height of electrodes or portions thereof, shapes of electrodes or portions thereof, or a combination thereof.

In some embodiments, electrodes are arranged in a pattern as pairs, or series. In some embodiments, arrangement of electrodes which vary in at least 2 or 3 dimensions, in pairs may be such that when a field is applied, one of the electrodes in the pair promotes fluid conductance in the dominant direction, and one in the undesired direction. In some embodiments, such electrodes may be constructed in particular geometries, as described herein, and as will be appreciated by one skilled in the art, such that fluid conductance in the desired direction, versus undesired direction is optimized. In some embodiments, the reverse is effected, such that certain electrode pairs, in some embodiments, promote greater fluid flow in a non-dominant direction, or in varied trajectories from that of the dominant or desired direction. According to this aspect, and in some embodiments, such electrodes may be positioned in between another electrode pair, which promotes fluid flow in a dominant direction, such that mixing of the fluid is localized to the first electrode pair, which when mixed is then conveyed in a dominant direction by the latter electrode pair. Various permutations of such arrangements to promote mixing and/or conveyance are readily apparent to one skilled in the art.

In some embodiments, the electrodes may be arranged in a series, with varying at least 2 of the 3 dimensions of at least one electrode in a given series. Such series may be odd- or even-in number. In some embodiments, the electrodes in a given series may vary in any way as described herein in terms of electrode geometry, patterning in the device, or a combination thereof, and the devices of this invention may comprise multiple series, which in turn may add to the complexity of the arrays of electrodes and capabilities of the devices of this invention.

In another embodiment, the gaps are between about 1 micron and about 50 microns, and in another embodiment, the electrode widths are between about 0.1 microns and about 50 microns.

In some embodiments, the term "dominant flow" refers to propulsion of fluid in alternating directions, which may be modulated, for example via varying the frequency or strength of the field applied, and/or varying or modulating the electrode heights, or portions thereof, resulting in a net conveyance of fluid in a desired direction at a specific time or condition. In some embodiments, the term "dominant flow" refers, to greater propulsion of fluid in a positive rather than negative direction. In some embodiments, the term "greater propulsion" refers to a net propulsion of 51%, or in another embodiment, 55%, or in another embodiment, 60%, or in another embodiment, 65%, or in another embodiment, 70%, or in another embodiment, 72%, or in another embodiment, 75%, or in another embodiment, 80%, or in another embodiment, 83%, or in another embodiment, 85%, or in another embodiment, 87%, or in another embodiment, 90%, or in another embodiment, 95% of the fluid being conveyed in a device of the invention, in a desired or positive direction. In some embodiments, the term "greater propulsion" reflects propulsion of the amount of fluid conveyed in a desired direction as a function of time, with propulsion being greater in a desired direction, predictably, in comparison to a similarly constructed device comprising electrodes of comparable, as opposed to varied height.

In some embodiments, the term "dominant flow" reflects propulsion of fluid conveyed in a desired direction, wherein such fluid is well mixed during, or prior to conveyance in a net desired direction.

The devices of this invention enable conveyance of a fluid, which is an electrolyte fluid. In one embodiment, the term "electrolyte fluid" refers to a solution, or in another embodiment, a suspension, or, in another embodiment, any liquid which will be conveyed upon the operation of a device of this invention. In one embodiment, such a fluid may comprise a liquid comprising salts or ionic species. In one embodiment, the ionic species may be present, at any concentration, which facilitates conduction through the devices of this invention. In one embodiment, the liquid is water, or in another embodiment, distilled deionized water, which has an ionic concentration ranging from about 10 nM to about 0.1M. In one embodiment, a salt solution, ranging in concentration from about 10 nM to about 0.1M is used.

In another embodiment, the fluid comprises solutions or buffered media for use suitable for the particular application of the device, for example, with regards to the method of cellular analysis, the buffer will be appropriate for the cells being assayed. In one embodiment, the fluid may comprise a medium in which the sample material is solubilized or suspended. In one embodiment, such a fluid may comprise bodily fluids such as, in some embodiments, blood, urine, serum, lymph, saliva, anal and vaginal secretions, perspiration and semen, or in another embodiment, homogenates of solid tissues, as described, such as, for example, liver, spleen, bone marrow, lung, muscle, nervous system tissue, etc., and may be obtained from virtually any organism, including, for example mammals, rodents, bacteria, etc. In some embodiments, the solutions or buffered media may comprise environmental samples such as, for example, materials obtained from air, agricultural, water or soil sources, which are present in a fluid which can be subjected to the methods of this invention. In another embodiment, such samples may be biological warfare agent samples; research samples and may comprise, for example, glycoproteins, biotoxins, purified proteins, etc. In another embodiment, such fluids may be diluted, so as to comprise a final electrolyte concentration which ranges from between about 10 nM-0.1M.

In one embodiment, the pH, ionic strength, temperature or combination thereof of the media/solution, etc., may be varied, to affect the assay conditions, as described herein, the rate of transit through the device, mixing within the device, or combination thereof.

As will be appreciated by those in the art, virtually any experimental manipulation may have been done on the sample prior to its use in embodiments of the present invention. For example, a variety of manipulations may be performed to generate a liquid sample of sufficient quantity from a raw sample. In some embodiments, gas samples and aerosol samples are so processed to generate a liquid sample containing molecules whose separation may be accomplished according to the methods of this invention.

In some embodiments, the devices of this invention make use of non-linear, electroosmotic flow to convey and/or mix fluids. In one embodiment, such flow is generated by the elements of the device, and their respective positioning in the device, as exemplified and described herein. In one embodiment, the pumping element is placed in an orientation that is perpendicular to the axis of the electric field, in a device of this invention. In one embodiment, the term "perpendicular" or "perpendicularly" refers to an orientation of a 90° angle with respect to the field axis, +/−5, or in another embodiment, at a 90° angle of +/−10°, or in another embodiment, at a 90° angle +/−20°.

Device operation relies upon the evolution of an electric field within the microchannel, which occurs, in some embodiments, as described in U.S. patent application Ser. No. 11/252,871, fully incorporated herein by reference.

In some embodiments of this invention, the devices exploit the effect of fixed-potential induced-charge electroosmosis (ICEO), where a "background" AC electric field acts on a "pumping" metal surface held a fixed potential relative to the background circuit, where "background electrodes" (B) and "pumping elements" (P) are arranged in periodic designs for efficient and long-range pumping down a microchannel. In some embodiments, modifications to the pumping elements are effected and fluid mixing can be achieved, at the same time as net pumping down the channel.

In one embodiment, each electrode in the pumping unit nearest to the electrode connected to the source will have an opposite polarity as compared to the electrode connected to the source. In another embodiment, the electrode in the pumping unit is connected to the electrode connected to the source, which is of the same polarity.

In some embodiments, background electrodes are positioned at a distance from the pumping elements of this invention. A characteristic separation, $L_0$, between the background electrodes sets the overall length scale of the device (including the smaller pumping elements). By providing the background electric field driving the flow, it also sets the scale of maximum slip velocity over the pumping element, $U_0 = \in V^2/\eta L_0$, and the lower bound on operating frequency, $v_0 = D/\lambda L_0$, according to the theory of fixed-potential ICEO, when V is the applied voltage; D is the diffusion coefficient of ions; λ is the Debye screening length; and $\in$ and η are the permittivity and viscosity of the fluid, respectively.

Reducing $L_0$ as much as possible, in one embodiment, is desirable when fabricating the devices of this invention. In one embodiment, $L_0$ will range from 0.01 to 1000 microns, or in another embodiment, 1-100, or in another embodiment, 10-100, or in another embodiment, 25-100, or in another embodiment, 25-500 microns.

In one embodiment, the background electrodes are so positioned so as not to be too close to the electrodes in the pumping elements described. In one embodiment, $L_1$ is the characteristic separation between a background electrode and the nearest pumping surface, and is less than $L_0$. According to this aspect of the invention, the AC frequency v must be larger than $v_1 = D/\lambda L_1$. In one embodiment, this is accomplished via the increase of the spacing of B and P in a simple linear layout as in FIG. 2.

In another embodiment, this is accomplished via raising the pumping elements into the channel or lowering the background electrodes into the substrate as exemplified hereinbelow. In another embodiment, the background electrodes are positioned off the main channel, for example in a recessed cavity, as exemplified herein. In another embodiment, combinations of these can be used, for example, recessed and lowered background electrodes. In some embodiments, the positioning of the background electrodes and pumping elements is such that the longitudinal period $L_0$ is comparable to, or in another embodiment, only slightly larger than the length of the pumping element.

In one embodiment, the pumping elements consist of pairs of interlaced electrodes connected to the background electrodes as exemplified hereinbelow, for example, as shown in FIG. 5. In fixed-potential ICEO, these electrodes should become fully screened by ions due to capacitive charging, before any screening of the background electrodes occurs. This can be accomplished by making the characteristic spacing $L_2$ of the adjacent electrodes in the pumping element smaller than $L_1$ and operating at a frequency v below $v_2 = D/\lambda L_2$ (>$v_1$). In one embodiment, the electrodes are not symmetrical with respect to a central axis in the pumping unit.

In some embodiments, the widths of the + and – electrodes in each pumping element are chosen to bias pumping in one direction, while maintaining sufficiently fast charging of the surfaces, as exemplified herein. For example, to pump via a background field directed from B+ to B–, a P–/+ pumping element placed therebetween should have its surface mostly covered by the electrode at the same voltage as B+, so its induced counter-charge in the diffuse part of the double layer in the fluid is positive. This assumes nearly complete screening of the closely spaced electrode surfaces in the pumping element before the further separated background electrodes become significantly screened during each AC period, in the appropriate frequency range, $v_1 < v < v_2$.

In some embodiments, the pumping element comprises interlaced electrodes, which can be varied to adjust the frequency response, pumping rate, and/or mixing capability of the device. In some embodiments, the electrodes of the pumping element comprise parallel stripes with arms, which can protrude into adjacent electrodes in the direction of desired fluid flow in the channel, which can shorten the electrode spacing and thus raise the upper critical frequency, $v_2$. Near this frequency, there will also be normal ACEO flow transverse to the channel, causing rolls that, in some embodiments are useful for mixing in the channel, or in other embodiments, passing particles in the fluid over a sensor on, for example, another wall of the microchannel. In another embodiment, the pumping element is not co-axial, with respect to the electrodes, in any dimension. In another embodiment, the pumping element is positioned on a different vertical plane, than the background electrodes.

In one embodiment, the pumping element comprises at least one electrode, which is not flat. In some embodiments, the electrodes in the pumping elements are so constructed so as to comprise sections having at least two different vertical positions. In some embodiments, the transition between sections of different vertical heights is smooth, or in other embodiments, step-wise. In some embodiments, the different vertical positions of the sections differ with respect to the background electrode, and with other sections in the same electrode, and in some embodiments, with other electrodes of which the pumping element is comprised.

In some embodiments, the devices of this invention comprise electrodes, which are interlaced electrodes, which can be varied to adjust the frequency response, rate of fluid conductance, and/or mixing capability of the device.

In some embodiments, the electrodes of this invention comprise parallel stripes with arms, which can protrude into adjacent electrodes in the direction of desired fluid flow in the channel, which can shorten the electrode spacing and thus raise the upper critical frequency, $v_2$. Near this frequency, there will also be normal ACEO flow transverse to the channel, causing rolls that, in some embodiments are useful for mixing in the channel, or in other embodiments, passing particles in the fluid over a sensor on, for example, another wall of the microchannel. In another embodiment, at least one electrode in the device, or an electrode of an electrode pair, or at least one electrode in an electrode series is not co-axial, with respect to other device electrodes, in any dimension.

The design of electrodes which comprise sections which vary in terms of their vertical position may be readily accomplished by known means in the art. For example, the devices may be fabricated as described herein, with successive electroplatings in order to alter the height, shape, etc. of the electrode. In some embodiments, such manufacture results in the production of electrodes with smooth transitions between the different vertical positions, and in other embodiments, with step-wise transitions, which vary in terms of the degree of drop between the different vertical positions. Positioning of these electrodes within the device, will, in some embodiments, be a reflection of a desired flow rate through the devices of this invention. In some embodiments, construction of the devices with such pumping elements facilitates greater flow rate, as a function of a "conveyor-belt" phenomenon, as described and exemplified herein.

In one embodiment, the pumping element is an array of pumping elements, as will be appreciated by one skilled in the art. Some embodiments of arrays of such elements are described herein, and polarity of the respective electrodes comprising the elements may be varied as a function of their placement in the device, as will be appreciated by one skilled in the art. In some embodiments, the pumping elements may have electrodes arranged with a variety of geometries, such as a square, hexagon, interlocking or inter-digitating designs, etc., as will be appreciated by one skilled in the art. Such orientation may be particularly useful in promoting mixing of the fluids used in the devices and methods of this invention. In one embodiment, a single unit functions as both micropump and micromixer, as will be appreciated by one skilled in the art. In one embodiment, the term "mixing" as used herein refers to circulation of materials to promote their distribution in a volume of space, for example, a mixture of 2 species, in a device of this invention, refers, in one embodiment, to a random distribution of the 2 species within a given volume of space of the device, e.g., in a microchannel of the devices of this invention. In one embodiment, the term "circulation" and "mixing" are interchangeable. In one embodiment, mixing refers to a change in a particular distribution which is not accompanied by agitation of the sample, in one embodiment, or in another embodiment, minimal agitation and/or formation of "bubbles" in the liquid medium in which the species are conveyed.

In some embodiments, the pumping element will comprise electrodes fashioned to assume a variety of geometries, as described and exemplified herein, to reflect a consideration of a desired trajectory for conducting the fluid in the devices of this invention, to suit a particular application. In some embodiments, the geometry may approximate a checkerboard, interlocked "E" designs, designs as depicted herein, or one related thereto.

While the electrode and field polarities as "+" and "–" signs throughout, all fields can also be AC or DC corresponding to electrode polarities oscillating between + and –, giving rise to the same induced-charge electro-osmotic flow. Thus all of the devices of the invention can operate in AC or DC.

In some embodiments, the present invention provides for the operation of the device in AC with DC offset, as will be understood by one skilled in the art, for example, as described in U.S. Pat. No. 5,907,155. In another embodiment, asymmetric driving signals may be used.

In some embodiments, this invention takes advantage of the fact that there is a competition between regions of oppositely directed electro-osmotic slip on the surfaces of interlaced electrodes of opposite polarity, which in turn results in net pumping over the surface. According to this aspect of the invention, by raising the surfaces pumping in the desired direction (and/or lowering those not pumping in the desired direction) one effectively "buries" the reverse convection rolls. If the height difference is comparable to the width of the buried electrodes, the reverse convection rolls turn over near the upper surface and provide an effective "conveyor belt" for the primary pumping flow over the raised electrodes, as further described and exemplified hereinbelow.

Figure 10A:
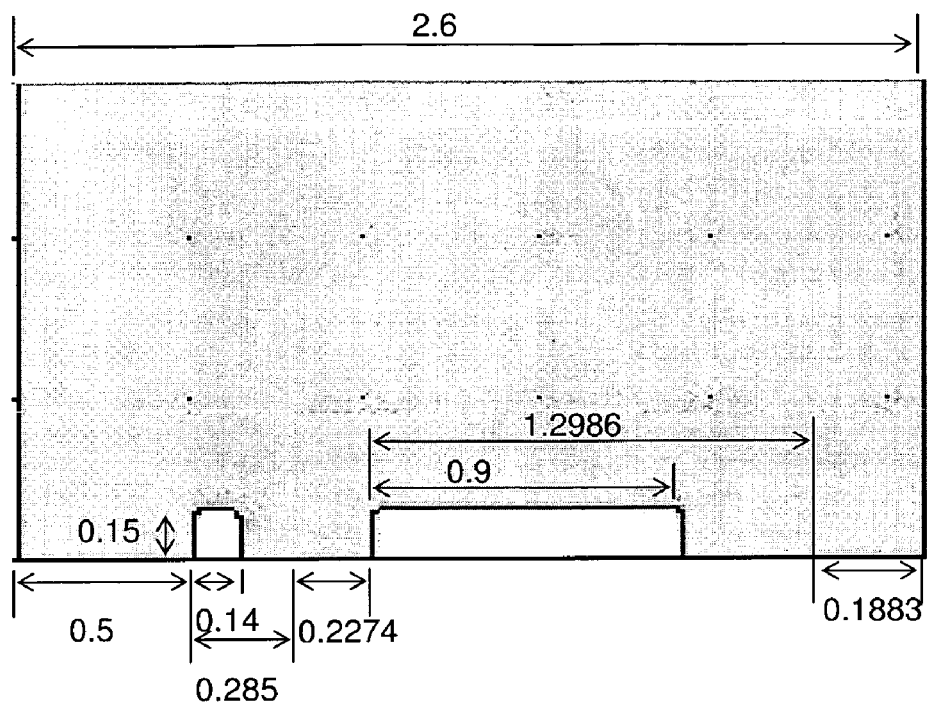
FIG. 10 demonstrates device designs, depicting the geometry (A) and simulated flow (B) for another embodiment of stepped electrodes.

In some embodiments, the pumping element has raised portions of the electrodes that pump in the dominant direction (up to stagnation points on each electrode), by a height varied proportionally to the width of the unraised region, for example as depicted in FIG. 10).

In some embodiments, the devices of this invention comprise pumping elements comprising raised electrodes, or in other embodiments, raised portions of electrodes, whose height is about proportional to the width of the unraised, recessed or combination thereof electrode, or portion of an electrode. In some embodiments the pumping elements comprising raised electrodes, or in other embodiments, raised portions of electrodes, have a height less than the width of the unraised, recessed or combination thereof electrode, or portion of an electrode. In some embodiments, the term "less than" in this context is by a value of about 1%, or about 5%, or about 8%, or about 10%, or about 15%, or about 17%, or about 20%, or about 25% or about 50%, as compared to the referenced value or parameter.

In some embodiments, the term "about" as used in this invention, is to be understood to encompass a value deviating by +/−1%, or in another embodiment, by +/−2.5%, or in another embodiment, by +/−5%, or in another embodiment, by +/−7.5%, or in another embodiment, by +/−10%, or in another embodiment, by +/−15%, or in another embodiment, by +/−20%, or in another embodiment, by +/−25%, with respect to the referenced value or parameter.

The simulated flow field shows that the reverse rolls have been recessed below a fairly smooth pumping flow, which is aided by the reduced hydrodynamic resistance of the tops of the reverse rolls. Plotting the time-averaged flow rate versus AC frequency of this versus previous designs shows a greater flow rates, achieving even as much as ten times faster than previously cited rates. (see for example, FIG. 11). Greater flow rates may be achieved by varying the geometry of the componenets of the device, and in view of the specific conditions employed.

This invention provides, in some embodiments, specific designs for periodic three-dimensional electrode structures, which achieve much faster flows than existing ACEO devices by roughly an order of magnitude, for the same applied voltage and minimum feature size, based on preliminary calculations and experiments conducted, for example as provided hereinbelow. In some embodiments, the design of the devices of this invention exploit the basic idea of fixed-potential ICEO, as well as a new concept of recessing reverse convection rolls as a "conveyor belt" to enhance the pumping flow driven by raised surfaces.

In one embodiment, the device is adapted such that analysis of a species of interest may be conducted, in one embodiment, in the device, or in another embodiment, downstream of the device. In one embodiment, analysis downstream of the device refers to removal of the obtained product from the device, and placement in an appropriate setting for analysis, or in another embodiment, construction of a conduit from the device, for example, from a collection port, which relays the material to an appropriate setting for analysis. In one embodiment, such analysis may comprise signal acquisition, and in another embodiment, a data processor. In one embodiment, the signal can be a photon, electrical current/impedance measurement or change in measurements. It is to be understood that the devices of this invention may be useful in various analytical systems, including bio-analysis micro-systems, due to the simplicity, performance, robustness, and ability to be integrated to other separation and detection systems and any integration of the device into such a system is to be considered as part of this invention.

In one embodiment, this invention provides an apparatus comprising a device of this invention, which in some embodiments, comprises the analytical modules as described herein.

Device geometry can take a variety of shapes and sizes. The background electrodes and/or pumping electrodes can be raised off the base substrate or flat. Background electrodes can, in some embodiments, be integrated into microchannels, microchannel walls, recessed from the conducting channel, as will be appreciated by one skilled in the art.

In some embodiments, devices with multiple electrodes, may comprise electrodes which are all of the same shape, different shapes, different sizes, etc. In some embodiments, the electrodes are fashioned as steps, rounded steps, trapezoids, which are continuous along the y-axis, z-axis, or combinations thereof, or in some embodiments, are discontinuous along the y-axis, z-axis, or combinations thereof. The electrodes of which the devices of this invention are comprised are co-axial in at most one dimension. The term "co-axial" refers, in some embodiments, to sharing a Cartesian axis with the indicated element. In some embodiments, the electrodes in the devices of this invention share an x-axis, a y-axis, but not a z-axis. In some embodiments, the electrodes as positioned in the devices of this invention share an x-axis and not a y- or a z-axis. In some embodiments, the electrodes as positioned in the devices of this invention have a comparable overall geometry, which differs in overall scale, or in some embodiments, differ primarily in height.

In some embodiments, electrodes are raised or lowered above the mean level of the microchannel surface, on which such electrodes are patterned or affixed, or the surface of the substrate, which comprises the electrodes as part of the microchannel surface. Such raising or lowering, will exceed that of the normal thickness of a metal layer, for example, such raising or lowering will be greater than a typical 1 micron thickness of previous electrodes used in certain microfluidic devices, such that the devices of this invention are more truly 3 dimensional structures.

In some embodiments, such electrodes may be formed or arranged in any geometry, such that electrodes are coaxial in at most one dimension, when such electrodes result in fluid flows of opposing direction.

External circuitry can be used to control electrical connections and/or to fix the voltage/potential of any or all of the electrodes. Background electrode potential can be controlled relative to the pumping element electrodes in magnitude, frequency, and phase lag.

In some embodiments, the total charge on the electrodes can also be controlled. Charge can be controlled relative to the background electrodes in magnitude, frequency, and phase lag, as above.

In some embodiments, additional electrode geometries can include rounded portions, which can be fabricated for instance, by evaporating through a narrow slit, or by wet etching a vertical, electroplated electrode.

In some embodiments, the background electrodes can be arranged in a variety of geometries relative to the pumping electrode. The background electrodes can be parallel to one another and transverse to a background fluid flow, or in other embodiments, they can be parallel to one another and parallel to background fluid flow. In some embodiments, they can have an angle between them, resulting in some electric field gradients, which may enhance fluid mixing.

The electrical connections between electrodes and external circuitry can, in some embodiments, be as simple as planar wires connecting the center posts to the external circuits. The electrical connections can be electroplated, in some embodiments. The electrical connections can be buried beneath an insulating material, in some embodiments.

Driving and control electronics can be manufactured on-chip along with the electrodes, in some embodiments. The driving and control electronics can be a separate electronics module, in some embodiments, an external stand-alone unit or microfabricated electronics. The microfabricated electronics module, in some embodiments, can be wire-bonded to the chip containing the electrodes or can be flip-chip bonded.

Fluidic channels can be fabricated by a variety of means, including soft-lithographic molding of polymers on rigid or semi-rigid molds. Channels can also be fabricated in glass via wet etching, plasma etching or similar means. Channels can be formed in plastics via stamping, hot embossing, or other similar machining processes. The channels can then be bonded to the substrate containing the electrode structures. Alignment marks can be incorporated onto the substrate to facilitate assembly. In some instances, metal surfaces can be exposed on substrate and channels to enable metal-to-metal bonding. Glass-to-glass bonding can be done at elevated temperatures and with applied potential. Plastic-to-glass can be facilitated with cleaning of glass surfaces prior to bonding, or fabrication of the fluidic portion of the device can be accomplished by any means known in the art.

Raised supports of an insulating or semiconducting nature can be fabricated on the substrate as well, in some embodiments, on which the pumping electrodes and/or background electrode may be mounted, to provide for differences in height, for uses as described herein.

In some embodiments, this invention provides a device comprising a microfluidic loop. In some embodiments, the device will comprise ports and machinery such that fluid injected in one port can be recirculated across one or more regions of the device, for example to regions for the detection of materials, or in some embodiments, separation of material, or in some embodiments, mixing of materials, which may be effected by the micropumps of the devices of this invention, prior to ejection through another port, in some embodiments, as described and exemplified herein.

In another embodiment, this invention provides a method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid.

In another embodiment, this invention provides a method of circulating or conducting a fluid, said method comprising applying a fluid to a device comprising at least one microfluidic channel, said microfluidic channel comprising:

i. a passageway for conducting an electrolyte fluid or circulating an electrolyte fluid, or a combination thereof; and ii. a plurality of electrodes positioned on, or comprising a surface of said microfluidic channel, wherein:

at least two of said plurality of electrodes are connected to a source, providing an electric field in said microchannel;

wherein said electrodes are parallel-positioned or interdigitated; and said electrodes or portions thereof are not co-axial, with respect to each other, in any dimension;

whereby upon application of said electric field, electro-osmotic flows with varied trajectories are generated in a region of said microchannel, resulting in mixing of said electrolyte fluid; a dominant electroosmotic flow is generated, which drives said electrolyte fluid across said microfluidic channel, or a combination thereof, thereby circulating or conducting a fluid.

In another embodiment, this invention provides a method of circulating or conducting a fluid, comprising applying a fluid to a device or an apparatus of this invention.

In some embodiments, the invention provides methods, devices and apparatuses for mixing or stirring fluid in a fixed chamber, and may optionally provide for long range pumping down a channel of a device of this invention. In some embodiments, such stirring may be applied in a multitude of applications, including any of the methods as described herein, or other applications, readily appreciated by one skilled in the art. For example, such methods, devices and apparatuses may find application in bioassays, and may, for example, impart greater speed or sensitivity to such assays. In some embodiments, such methods, devices and apparatuses may find application in the construction, probing or assay of DNA arrays, in a fixed chamber, or in another embodiment, in a microfluidic loop arrangement and may, for example, impart greater speed or sensitivity to such assays, allow for smaller sample or probe quantities for such assay, or other advantages apparent to one in the art.

In some embodiments, the "circulating" or "mixing" capabilities of the methods, devices and apparatuses of this invention may involve some component of the flow over the electrodes impinging on another wall of the channel, resulting in recirculation, which in turn, may not flow in the "dominant" flow direction, yet in some aspects, will not detract from the flow in the dominant direction, since for example, pumping down a long channel may occur concurrent with weak or less transverse or sideways component flow impinging on the side walls to generate some mixing, while pumping down the channel.

In some embodiments, the methods, devices and apparatuses of this invention may circulate fluid in a "closed box" where fluid is injected into the device by any means known in the art, prior to or without conveyance of the fluid in a dominant direction, for example, down a long axis of a microchannel of a device of the invention.

In some embodiments, the term "mixing" refers to fluid in the devices/apparatuses of the invention having at least one varied trajectory. In some embodiments, the devices/apparatuses of the invention promote flow along at least one trajectory that effectively stirs the fluid, circulates the fluid, or a combination thereof.

In some embodiments, the invention provides devices/apparatuses/methods for circulating/mixing a fluid over a target surface with a bound reagent, or in other embodiments, circulates a fluid having a reagent that specifically fluorescently labels analytes that are bound to that surface, which may be assessed via optical means, or in some embodiments, the surface is so constructed so as to detect changes in gate voltage on a transistor structure when an analyte or reagent binds, and when binding creates electrical, conducting, or semiconducting connections between two electrodes on the surface. Such applications may find use in the methods of this invention, as described herein, and as will be appreciated by one skilled in the art.

In some embodiments, this invention provides for analysis, detection, concentration, processing, assay, production of any material in a microfluidic device, whose principle of operation comprises electro-osmotically driven fluid flow, for example, the incorporation of a source providing an electric field in a microchannel of the device, and provision of an electrokinetic means for generating fluid motion whereby interactions between the electric field and induced-charge produce electro-osmotic flows. Such flows may in turn, find application in fluid conductance, mixing of materials, or a combination thereof, and any application which makes use of these principles is to be considered as part of this invention, representing an embodiment thereof.

In some embodiments, the invention provides methods for circulating fluid in a microfluidic cavity, comprising applying the fluid to a device comprising two or more interdigitated electrodes connected to a source wherein at least one electrode has stepped or recessed features, which in some embodiments, produces a flow, which has a nonzero component directed toward a boundary of a channel in the device. In some embodiments, such devices and methods of their use allow for the conveyance of, inter alia, cells, analytes, antibodies, antigens, DNA, polymers, proteins in solution, and others over a desired surface, for example, a detection surface.

According to this aspect, and in some embodiments, a capture antibody, or cross-linking agent, or enzyme in solution is applied to such device, and is conducted such that these reagents come into contact with the desired surface. In some embodiments, a portion of the device optically transparent, or facilitates optical detection of a label, which may be incorporated in the agents or reagents as described herein, to facilitate detection. For example, at least a portion of the device may be transparent at a wavelength corresponding to excitation and emission for a fluorescent tag, which may be coupled to a reagent or compound in the fluids applied to the device. In some embodiments, according to this aspect, the device may be constructed to comprise non-transparent sections, to minimize or abrogate photobleaching of sensitive reagents.

In another embodiment, this invention provides a method of cellular analysis, comprising the steps of:
  a. introducing a buffered suspension comprising cells to a first port of a device;
  b. introducing a reagent for cellular analysis to said first or to a second port of said device, said device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof; and
  c. analyzing at least one parameter affected by contact between said suspension and said reagent.

In another embodiment, this invention provides a method of cellular analysis, comprising the steps of:
  a. introducing a buffered suspension comprising cells to a first port of a device;
  b. introducing a reagent for cellular analysis to said first or to a second port of said device, said device comprising at least one microfluidic channel, comprising a plurality of electrodes positioned on, or comprising a surface of said microfluidic channel, wherein:
    at least two of said plurality of electrodes are connected to a source, providing an electric field in said microchannel;
    wherein said electrodes are parallel-positioned or interdigitated; and
    said electrodes or portions thereof are not co-axial, with respect to each other, in any dimension;
    whereby upon application of said electric field, electro-osmotic flows with varied trajectories are generated in a region of said microchannel, resulting in mixing of said electrolyte fluid; a dominant electroosmotic flow is generated, which drives said electrolyte fluid across said microfluidic channel, or a combination thereof; and
  c. analyzing at least one parameter affected by contact between said suspension and said reagent.

In another embodiment, this invention provides a method of cellular analysis, comprising the steps of:
  a. introducing a buffered suspension comprising cells to a device of this invention, including any embodiment thereof;
  b. introducing a reagent for cellular analysis to the devices of this invention, whereby upon application of an electric field, electro-osmotic flows with varied trajectories are generated in a region of a microchannel in the device, resulting in mixing of electrolyte fluid; a dominant electroosmotic flow is generated, which drives electrolyte fluid across a microfluidic channel of the device, or a combination thereof; and
  c. analyzing at least one parameter affected by contact between said suspension and said reagent.

In one embodiment, the reagent is an antibody, a nucleic acid, an enzyme, a substrate, a ligand, or a combination thereof. In another embodiment, the reagent is coupled to a detectable marker, which in another embodiment is a fluorescent compound. In another embodiment, the device is coupled to a fluorimeter or fluorescent microscope. In another embodiment, the device is comprised of a transparent material.

In another embodiment, the method further comprises the step of introducing a cellular lysis agent in an inlet port of said device. According to this aspect of the invention, and in one embodiment, the reagent specifically interacts or detects an intracellular compound.

In another embodiment, a secondary reagent may also be present in addition to the lysing agent for facilitating further analysis or manipulation of the cells.

In one embodiment, the surface of the microchannel may be functionalized to reduce or enhance adsorption of species of interest to the surface of the device. In another embodiment, the surface of the microchannel has been functionalized to enhance or reduce the operation efficiency of the device.

In one embodiment, the device is further modified to contain an active agent in the microchannel, or in another embodiment, the active agent is introduced via an inlet into the device, or in another embodiment, a combination of the two is enacted. For example, and in one embodiment, the microchannel is coated with an enzyme at a region wherein molecules introduced in the inlet will be conveyed past, according to the methods of this invention. According to this aspect, the enzyme, such as, a protease, may come into contact with cellular contents, or a mixture of concentrated proteins, and digest them, which in another embodiment, allows for further assay of the digested species, for example, via introduction of a specific protease into an inlet which conveys the enzyme further downstream in the device, such that essentially digested material is then subjected to the activity of the specific protease. This is but one example, but it is apparent to one skilled in the art that any number of other reagents may be introduced, such as an antibody, nucleic acid probe, additional enzyme, substrate, etc.

In one embodiment, processed sample is conveyed to a separate analytical module. For example, in the protease digested material described hereinabove, the digestion products may, in another embodiment, be conveyed to a peptide analysis module, downstream of the device. The amino acid sequences of the digestion products may be determined and assembled to generate a sequence of the polypeptide. Prior to delivery to a peptide analysis module, the peptide may be conveyed to an interfacing module, which in turn, may perform one or more additional steps of separating, concentrating, and or focusing.

In another embodiment, the microchannel may be coated with a label, which in one embodiment is tagged, in order to identify a particular protein or peptide, or other molecule containing the recognized epitope, which may be a means of sensitive detection of a molecule in a large mixture, present at low concentration.

For example, in some embodiments, reagents may be incorporated in the buffers used in the methods and devices of this invention, to enable chemiluminescence detection. In some embodiments the method of detecting the labeled material includes, but is not limited to, optical absorbance, refractive index, fluorescence, phosphorescence, chemiluminescence, electrochemiluminescence, electrochemical detection, voltametry or conductivity. In some embodiments, detection occurs using laser-induced fluorescence, as is known in the art.

In some embodiments, the labels may include, but are not limited to, fluorescent lanthanide complexes, including those of Europium and Terbium, fluorescein, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-,tetraioide, which is sold under the name YOYO-1, Cy and Alexa dyes, and others described in the 9th Edition of the Molecular Probes Handbook by Richard P. Haugland, hereby expressly incorporated by reference. Labels may be added to 'label' the desired molecule, prior to introduction into the devices of this invention, in some embodiments, and in some embodiments the label is supplied in a microfluidic chamber. In some embodiments, the labels are attached covalently as is known in the art, or in other embodiments, via non-covalent attachment.

In some embodiments, photodiodes, confocal microscopes, CCD cameras, or photomultiplier tubes maybe used to image the labels thus incorporated, and may, in some embodiments, comprise the apparatus of the invention, representing, in some embodiments, a "lab on a chip" mechanism.

In one embodiment, detection is accomplished using laser-induced fluorescence, as known in the art. In some embodiments, the apparatus may further comprise a light source, detector, and other optical components to direct light onto the microfluidic chamber/chip and thereby collect fluorescent radiation thus emitted. The light source may comprise a laser light source, such as, in some embodiments, a laser diode, or in other embodiments, a violet or a red laser diode. In other embodiments, VCSELs, VECSELs, or diode-pumped solid state lasers may be similarly used. In some embodiments, a Brewster's angle laser induced fluorescence detector may used. In some embodiments, one or more beam steering mirrors may be used to direct the beam to a desired location for detection.

In one embodiment, a solution or buffered medium comprising the molecules for assay are used in the methods and for the devices of this invention. In one embodiment, such solutions or buffered media may comprise natural or synthetic compounds. In another embodiment, the solutions or buffered media may comprise supernatants or culture media, which in one embodiment, are harvested from cells, such as bacterial cultures, or in another embodiment, cultures of engineered cells, wherein in one embodiment, the cells express mutated proteins, or overexpress proteins, or other molecules of interest which may be thus applied. In another embodiment, the solutions or buffered media may comprise lysates or homogenates of cells or tissue, which in one embodiment, may be otherwise manipulated for example, wherein the lysates are subject to filtration, lipase or collagenase, etc., digestion, as will be understood by one skilled in the art. In one embodiment, such processing may be accomplished via introduction of the appropriate reagent into the device, via, coating of a specific channel, in one embodiment, or introduction via an inlet, in another embodiment.

It is to be understood that any complex mixture, comprising two or more molecules, whose assay is desired, may be used for the methods and in the devices of this invention, and represent an embodiment thereof.

In another embodiment, this invention provides a method of high-throughput, multi-step product formation, the method comprising the steps of:

a. introducing a first liquid comprising a precursor to a first port of a device;

b. introducing a second liquid comprising a reagent, catalyst, reactant, cofactor, or combination thereof to said first port, or a second port of said device, said device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, and a product of said precursor is formed in said device; and c. collecting said product from said device.

In another embodiment, this invention provides a method of high-throughput, multi-step product formation, the method comprising the steps of:

a. introducing a first liquid comprising a precursor to a first port of a device;

b. introducing a second liquid comprising a reagent, catalyst, reactant, cofactor, or combination thereof to said first port, or a second port of said device, said device comprising at least one microfluidic channel, comprising a plurality of electrodes positioned on, or comprising a surface of said microfluidic channel, wherein:

at least two of said plurality of electrodes are connected to a source, providing an electric field in said microchannel;

wherein said electrodes are parallel-positioned or interdigitated; and said electrodes or portions thereof are not co-axial, with respect to each other, in any dimension;

whereby upon application of said electric field, electro-osmotic flows with varied trajectories are generated in a region of said microchannel, resulting in mixing of said electrolyte fluid; a dominant electroosmotic flow is generated, which drives said electrolyte fluid across said microfluidic channel, or a combination thereof, and a product of said precursor is formed in said device; and c. collecting said product from said device.

In another embodiment, this invention provides a method of method of high-throughput, multi-step product formation, the method comprising the steps of:

a. introducing a first liquid comprising a precursor to a device of this invention, including any embodiment thereof;

b. introducing a second liquid comprising a reagent, catalyst, reactant, cofactor, or combination thereof to the device of this invention, whereby upon application of an electric field, electro-osmotic flows with varied trajectories are generated in a region of a microchannel of a device of this invention, resulting in mixing of said electrolyte fluid; a dominant electroosmotic flow is generated, which drives electrolyte fluid across the microfluidic channel, or a combination thereof, and a product of the precursor is formed in the device; and c. collecting the product from the device.

In one embodiment, the microfluidic device comprises:

i. one or more inlet ports;

ii. at least one outlet port; and iii. microfluidic channels in fluid communication with said ports, which further comprise at least two background electrodes connected to a source, providing an electric field in said microchannel; and at least one pumping element comprising two or more parallel-positioned or interdigitated electrodes, positioned between said at least two electrodes;

wherein said pumping element is positioned co-axially, with respect to said electrodes, in at most one dimension, so that interactions between said field and said pumping element produce electro-osmotic flows driving said electrolyte fluid across said microfluidic channel.

In another embodiment, this invention provides a method of analyte detection or assay, comprising the steps of:

a. introducing a first fluid comprising an analyte to a first port of a microfluidic device;

b. introducing a second fluid comprising a reagent to said first port or to a second port of said microfluidic device, said microfluidic device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said fluid comprising said analyte and reagent; a dominant electroosmotic flow is generated, which drives said electrolyte fluid comprising said analyte and reagent across said chamber, or a combination thereof; and c. detecting, analyzing, or a combination thereof, of said analyte.

In another embodiment, this invention provides a method of analyte detection or assay, comprising the steps of:

a. introducing a first fluid comprising an analyte to a first port of a microfluidic device;

b. introducing a second fluid comprising a reagent to said first port or to a second port of said microfluidic device, said microfluidic device comprising at least one microfluidic channel, comprising a plurality of electrodes positioned on, or comprising a surface of said microfluidic channel, wherein:

at least two of said plurality of electrodes are connected to a source, providing an electric field in said microchannel;

wherein said electrodes are parallel-positioned or interdigitated; and said electrodes or portions thereof are not co-axial, with respect to each other, in any dimension;

whereby upon application of an electric field, electro-osmotic flows with varied trajectories are generated in a region of a microchannel of a device of this invention, resulting in mixing of said electrolyte fluid comprising said analyte and reagent; a dominant electroosmotic flow is generated, which drives electrolyte fluid comprising said analyte and reagent across the microfluidic channel, or a combination thereof; and c. detecting, analyzing, or a combination thereof, of said analyte.

In another embodiment, this invention provides a method of analyte detection or assay, comprising the steps of:

a. introducing a first fluid comprising an analyte to a device of this invention, including any embodiment thereof;

b. introducing a second fluid comprising a reagent to the device, whereby upon application of said electric field, electro-osmotic flows with varied trajectories are generated in a region of said microchannel, resulting in mixing of said fluid comprising said analyte and reagent; a dominant electroosmotic flow is generated, which drives said electrolyte fluid comprising said analyte and reagent across said microfluidic channel, or a combination thereof; and c. detecting, analyzing, or a combination thereof, of said analyte.

In one embodiment, the microfluidic device comprises:

i. one or more inlet ports;

ii. at least one outlet port; and iii. microfluidic channels in fluid communication with said ports, which further comprise at least two background electrodes connected to a source, providing an electric field in said microchannel; and at least one pumping element comprising two or more parallel-positioned or interdigitated electrodes, positioned between said at least two electrodes;

wherein said pumping element is positioned co-axially, with respect to said electrodes, in at most one dimension, so that interactions between said field and said pumping element produce electro-osmotic flows driving said electrolyte fluid across said microfluidic channel.

In one embodiment, the method further comprises the step of carrying out iterative introductions of said second liquid, as in (b), to additional inlet ports. In one embodiment, the reagent is an antibody, a nucleic acid, an enzyme, a substrate, a ligand, a reactant or a combination thereof.

In another embodiment, this invention provides a method of drug processing and delivery, the method comprising the steps of:
a. introducing a drug and a liquid comprising a buffer, a catalyst, or combination thereof to a device, comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1%, whereby upon application of said electric field, electro-osmotic flows with at least one varied trajectory is generated in a region of said chamber, resulting in mixing of said electrolyte fluid comprising said drug; a dominant electroosmotic flow is generated, which drives said electrolyte fluid comprising said drug across said chamber, or a combination thereof; and
b. collecting said drug, delivering said drug to a subject, or a combination thereof.

In one embodiment, the method further comprises carrying out iterative introductions of said second liquid to said inlet ports. In another embodiment, the second liquid serves to dilute the drug to a desired concentration.

In another embodiment, this invention provides a method of drug processing and delivery, the method comprising the steps of:
a. introducing a drug and a liquid comprising a buffer, a catalyst, or combination thereof to a device, comprising at least one microfluidic channel, comprising a plurality of electrodes positioned on, or comprising a surface of said microfluidic channel, wherein:
at least two of said plurality of electrodes are connected to a source, providing an electric field in said microchannel;
wherein said electrodes are parallel-positioned or interdigitated; and
said electrodes or portions thereof are not co-axial, with respect to each other, in any dimension;
whereby upon application of said electric field, electro-osmotic flows with varied trajectories are generated in a region of said microchannel, resulting in mixing of said electrolyte fluid comprising said drug; a dominant electroosmotic flow is generated, which drives said electrolyte fluid comprising said drug across said microfluidic channel, or a combination thereof, and
b. collecting said drug, delivering said drug to a subject, or a combination thereof.

In some embodiments, the term "drug processing" refers to reconstitution of a drug, altering a drug, modifying a drug, or any preparation desired to prepare a drug or composition for administration to a subject.

In some embodiments, the invention provides devices preloaded with a compound, for example a lyophilized drug, which is packaged and distributed as such, under sterile conditions. In some embodiments, according to this aspect, a fluid is introduced into such a device, and the drug or other compound contained therewithin is reconstituted or diluted or processed, in some embodiments, just prior to delivery to a subject, or for any period of time, or for storage, etc.

In another embodiment, this invention provides a method of drug processing and delivery, the method comprising the steps of:

a. introducing a first liquid comprising a drug to a first port of a device of this invention, including any embodiment thereof;
b. introducing a second liquid comprising a buffer, a catalyst, or combination thereof to said first port or to a second port of said device, whereby upon application of an electric field, electro-osmotic flows with varied trajectories are generated in a region of a microchannel of the device, resulting in mixing of the electrolyte fluid comprising the drug; a dominant electroosmotic flow is generated, which drives electrolyte fluid comprising the drug across a microfluidic channel of the device, or a combination thereof; and
c. collecting the drug, delivering the drug to a subject or a combination thereof.

In one embodiment, the microfluidic device comprises:
i. one or more inlet ports;
ii. at least one outlet port; and
iii. microfluidic channels in fluid communication with said ports, which further comprise
at least two background electrodes connected to a source, providing an electric field in said microchannel; and
at least one pumping element comprising two or more parallel-positioned or interdigitated electrodes, positioned between said at least two electrodes;
wherein said pumping element is positioned co-axially, with respect to said electrodes, in at most one dimension, so that interactions between said field and said pumping element produce electro-osmotic flows driving said electrolyte fluid across said microfluidic channel.

In one embodiment, the method further comprises carrying out iterative introductions of said second liquid to said inlet ports. In another embodiment, the second liquid serves to dilute the drug to a desired concentration.

Metabolic processes and other chemical processes can involve multiple steps of reactions of precursors with an enzyme, or catalyst, or mimetic, etc., in some embodiments, with or without the involvement of cofactors, in other embodiments, to obtain specific products, which in turn are reacted, to form additional products, etc., until a final desired product is obtained. In one embodiment, the devices and/or methods of this invention are used for such a purpose. In one embodiment, such methodology enables use of smaller quantities of reagents, or precursors, which may be limiting, in other embodiments, wherein such methodology enables isolation of highly reactive intermediates, which in turn may promote greater product formation. It will be apparent to one skilled in the art that a means for stepwise, isolated or controlled synthesis provides many advantages, and is amenable to any number of permutations.

It is to be understood that any of the embodiments described herein, with regards to samples, reagents and device embodiments are applicable with regard to any method as described herein, representing embodiments thereof.

In another embodiment, the induced-charge electroosmotic devices of this invention circulate solutions containing probe molecules over target surfaces. In one embodiment, the probe may be any molecule, which specifically interacts with a target molecule, such as, for example, a nucleic acid, an antibody, a ligand, a receptor, etc. In another embodiment, the probe will have a moiety which can be chemically cross-linked with the desired target molecule, with reasonable specificity, as will be appreciated by one skilled in the art. According to this aspect of the invention and in one embodiment, a microchannel of the device may be coated with a mixture, lysate, sample, etc., comprising a target molecule of interest.

In one embodiment, such a device provides an advantage in terms of the time needed for assay, the higher sensitivity of detection, lower concentration of sample/reagents needed, since the sample may be recirculated over the target surface, or combination thereof.

In some embodiments, in devices for use in regulating drug delivery, the second liquid serves to dilute the drug to a desired concentration. In one embodiment, the device comprises valves, positioned to regulate fluid flow through the device, such as, for example, for regulating fluid flow through the outlet of the device, which in turn prevents depletion from the device, in one embodiment. In another embodiment, the positioning of valves provides an independent means of regulating fluid flow, apart from a relay from signals from the subject, which stimulate fluid flow through the device.

In another embodiment, this invention provides a device for use in drug delivery, wherein the device conveys fluid from a reservoir to an outlet port. In one embodiment, drug delivery according to this aspect of the invention, enables mixing of drug concentrations in the device, or altering the flow of the drug, or combination thereof, or in another embodiment, provides a means of continuous delivery. In one embodiment, such a device may be implanted in a subject, and provide drug delivery in situ. In one embodiment, such a device may be prepared so as to be suitable for transdermal drug delivery, as will be appreciated by one skilled in the art.

Although the present invention has been shown and described with respect to several preferred embodiments thereof, various changes, omissions and additions to the form and detail thereof, may be made therein, without departing from the spirit and scope of the invention.

EXAMPLES

Example 1

General Schematic for a Device Comprising Induced-Charge Electro-Osmotically Driven Microfluidic Pumps It is possible to create many permutations of a device comprising induced-charge electro-osmotically driven microfluidic mixers or pumps, or a combination thereof, as will be appreciated by one skilled in the art.

A general schematic of microfluidic devices for use in this invention is depicted in FIG. 1. In this embodiment, metal electrodes (1-10) are patterned onto a substrate (1-20), typically glass or silicon, to form an electrokinetic "pump". Fluid is pumped down a microfluidic channel (1-30), which may be formed by a molded-polymer (e.g. PDMS) cap. Typical dimensions for the cross section of the microchannel are of order 1-1000 microns in height and 10-10000 microns in width.

Figure 1B:
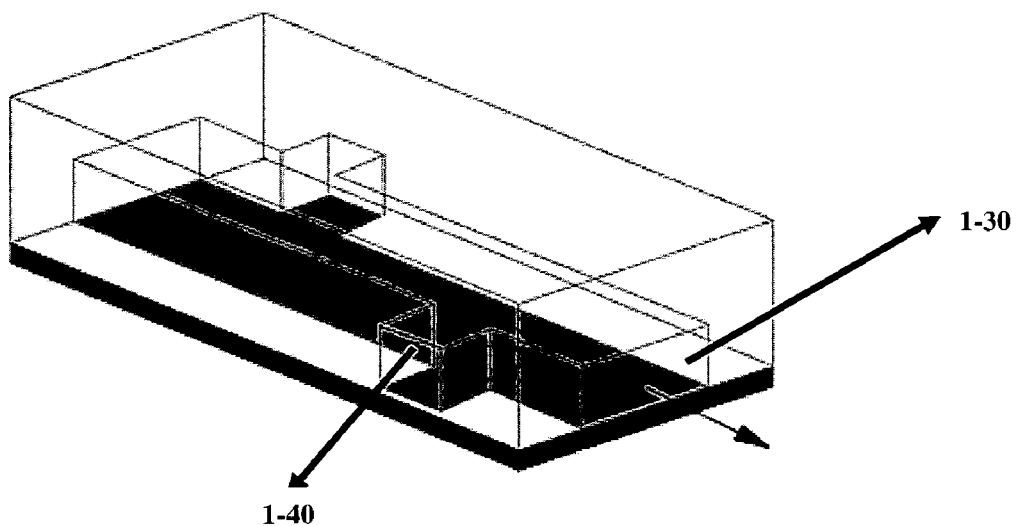
Figure 1C:
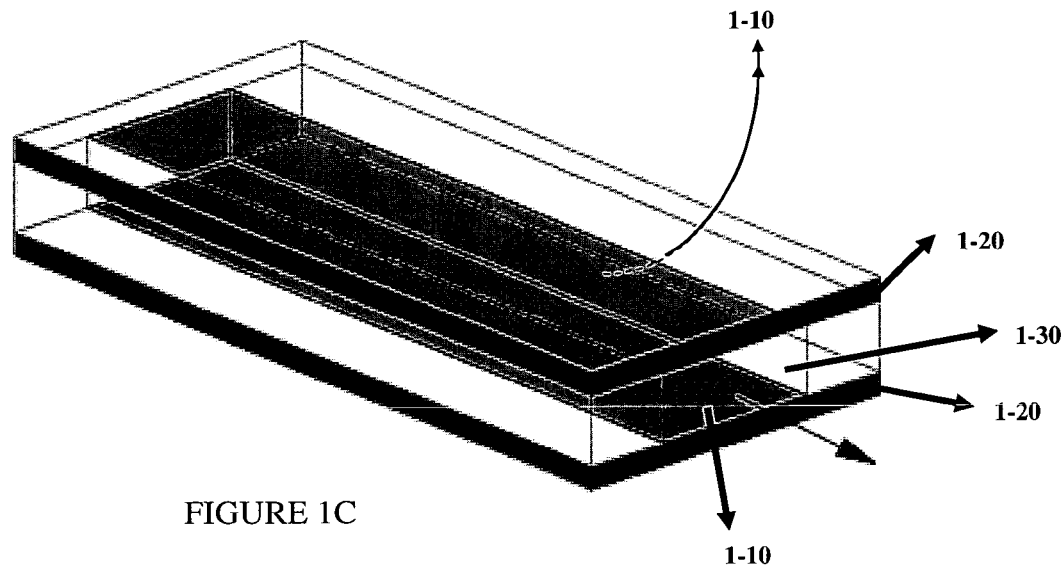

The microfluidic channels may be straight (FIG. 1A) or have recessed regions (1-40) (FIG. 1B). In such channels designed for biological or chemical sensing, the upper surface and side walls may have embedded sensors. In channels for long-range pumping, pressure generation, or electrokinetic injection, the upper surface may consist of a similar electrokinetic pump (on an upside-down substrate) with the channel formed by sandwiching a spacer layer in between as in FIG. 1C.

In FIG. 1, the effect of fixed-potential ICEO, where a "background" AC electric field acts on a "pumping" metal surface held a fixed potential relative to the background circuit, is shown. According to this embodiment, the cylinder can be grounded to one background electrode, and the ICEO pumping velocity is directed toward that electrode and depends on the position of the cylinder.

In one embodiment of the present invention, the "background electrodes" (B) and "pumping elements" (P) are positioned in periodic designs, which provide, in some embodiments, for more efficient, long-range pumping down a microchannel. Modifications to the pumping elements as depicted can produce mixing, as well as net pumping down the channel.

In some embodiments, the electrodes and metal structures are all "flat" in the sense that the primary exposed surfaces are co-planar and parallel to one channel wall (e.g. the glass or silicon substrate used in fabrication), although the electrodes may be arranged at different heights and transverse positions in three-dimensional geometries. In other embodiments, this invention provides devices comprising periodic arrays of non-flat, three-dimensional electrodes, with raised and lowered sections (on a single electrode).

Example 2

Circuitry and Spatial Layout for some Devices of this Invention

Figure 2A:
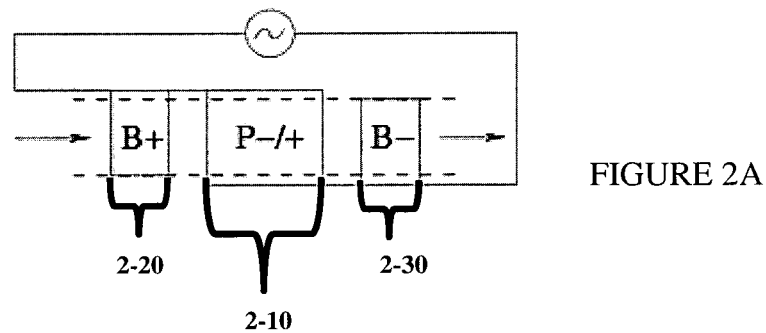
FIG. 2 schematically depicts an embodiment of the layout of the electrical circuit in a pump of this invention, consisting of background electrodes (B) (2-20; 2-30) and pumping elements (P) (2-10; 20-40) patterned on the substrate, in a single half period (A) or a complete period which may be repeated indefinitely (B). The channel side walls may meet the substrate (dashed lines) so as to cover the electrical connections between the elements and to the (typically AC) power source. $L_1$ (2-50) is the spacing between a background electrode and pumping element. Lighter arrows indicate the direction of fluid pumping down the microchannel.
Figure 2B:
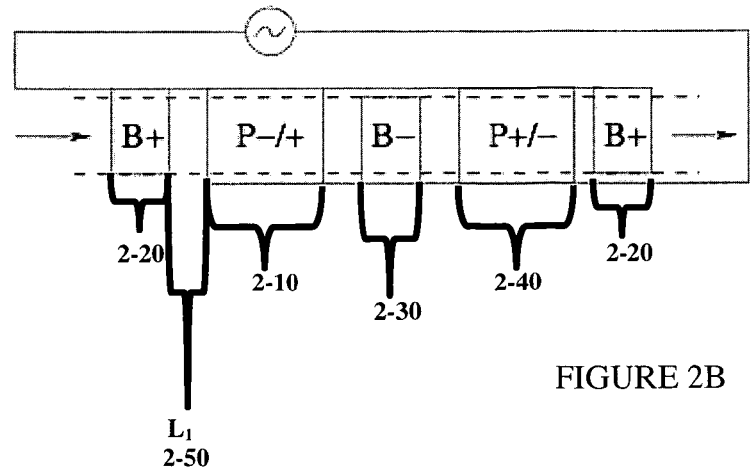

The electrical circuitry and general spatial layout are shown in FIG. 2. According to this embodiment, (FIG. 2A) two background electrodes, B+ (2-20) and B− (2-30), apply an AC electric field across a single primary pumping element, P−/+ (2-10), which consists of interlaced electrodes connected to B+ and B− as described further, hereinbelow. Another embodiment comprises successive positioning of the elements, for example as depicted in FIG. 2B, where a pumping element with the opposite symmetry, P+/− (240), is positioned in the device, in a repeating pattern, for example B+, P−/+, B−, P+/−, etc.

According to these embodiments, fluid pumps from left to right, as indicated by the arrows in FIG. 2. When the background electric field extends from B+ to B−, the P−/+pumping element causes pumping in the same direction since the induced double layer charge is predominantly positive, due to a larger surface area at the same voltage as B− (than at that of B+) in the pumping element, as described below.

The characteristic separation, $L_0$, between the background electrodes sets the overall length scale of the device (including the smaller pumping elements). By providing the background electric field driving the flow, it also sets the scale of maximum slip velocity over the pumping element, $U_0 = \in V^2 / \eta L_0$, and the lower bound on operating frequency, $v_0 = D/\lambda L_0$, (in the absence of Faradaic reactions, which would also permit DC operation at zero frequency) according to the theory of fixed-potential ICEO.

In these formulae, V is the applied voltage; D is the diffusion coefficient of ions; $\lambda$ is the Debye screening length; and $\in$ and $\eta$ are the permittivity and viscosity of the fluid, respectively. It is clearly desirable to reduce $L_0$ as much as possible while maintaining affordable and reliable fabrication and avoiding changes in the physics of ICEO, which may involve minimum feature sizes at the micron scale and $L_0$ of order 10-100 microns.

In order to avoid ionic screening of the background electrodes, in the devices of this invention, the placement of the background electrodes cannot be too close to the electrodes in the pumping elements described. If $L_1$ ($<L_0$) is the characteristic separation between a background electrode and the nearest pumping surface, then the AC frequency v must be larger than $v_1=D/\lambda L_1$ ($>v_0$). One embodiment of the device, which addresses this issue, increases the spacing of B and P in a simple linear layout as in FIG. 2. According to this embodiment, however, pumping velocity may be somewhat diminished (for the same voltage and minimum feature size) by increasing the period $L_0$.

Figure 3A:
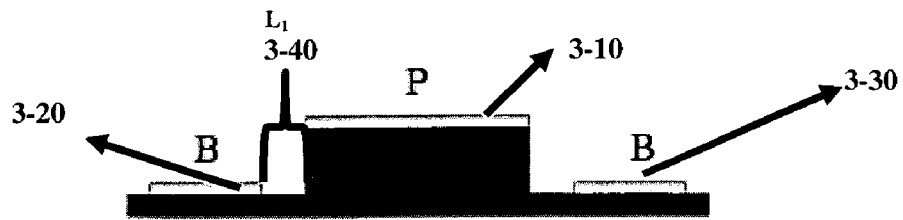
FIG. 3 schematically depicts a cross-sectional side view of the placement of background electrodes (B) (3-20; 3-30) and a pumping element (P) (3-10) in embodiments of the designs in FIG. 2 with raised pumping elements (A) or lowered background electrodes (B). $L_1$ (340) is the spacing between a background electrode and pumping element.
Figure 3B:
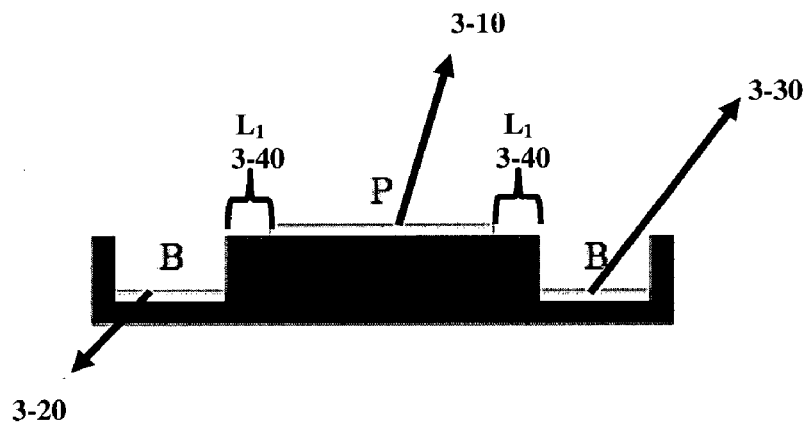

Another embodiment comprises raising the pumping elements (3-10) in the channel or, in another embodiment, lowering the background electrodes (3-20; 3-30) into the substrate as shown in FIGS. 3A and 3B, respectively. Raised electrodes are easily fabricated and have the added advantage of confining the background electric field closer to the ceiling of the microchannel, thus further increasing the flow rate.

Figure 4:
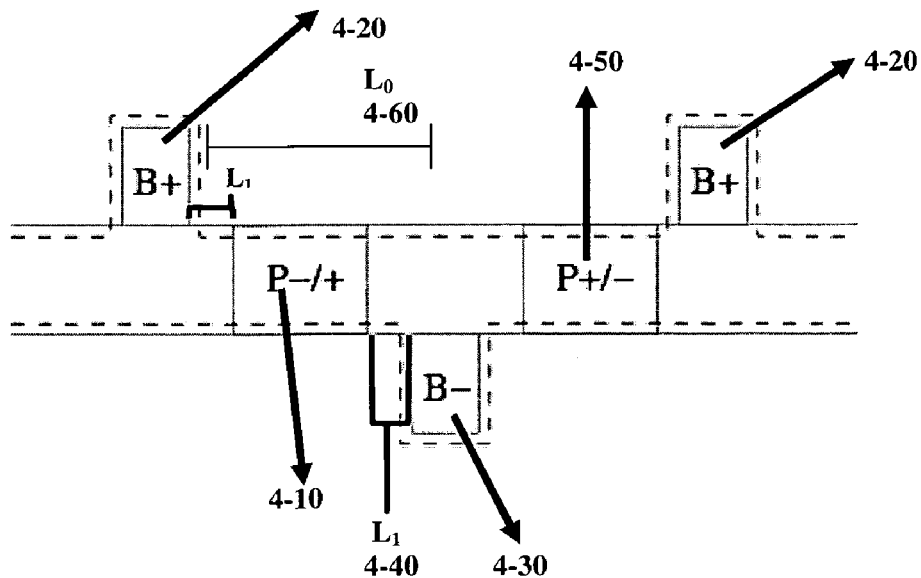
FIG. 4 schematically depicts a top/plan view of an arrangement of pumping elements (4-10) in a microchannel floor where the background electrodes are off to the side in recessed cavities (as shown in FIG. 1B). The dashed lines show possible positions for the side walls in this design. $L_1$ (3-40) represents the distance between the background electrode and pumping element, $L_0$ (3-60) the distance between the two background electrodes.

In another embodiment (FIG. 4), background electrodes (4-20; 4-30) are positioned laterally, in a recessed region of the microchannel wall (e.g. as shown in FIG. 1B). In another embodiment, such changes in positioning may be combined (e.g. combining FIGS. 3 and 4) such that the longitudinal period $L_0$ (3-60) is comparable to (or slightly larger than) the length of the pumping element.

The pumping elements of the devices of the invention, in some embodiments, consist of pairs of interlaced electrodes connected to the background electrodes (5-20; 5-30) as shown in FIG. 5. While two pairs of electrodes are shown in the figure, it is to be understood that additional pairs can be incorporated, as desired. In fixed-potential ICEO, these electrodes, in some embodiments, may be fully screened by ions due to capacitive charging, before any screening of the background electrodes occurs. This can be accomplished, for example, by making the characteristic spacing $L_2$ (5-70) of the adjacent electrodes in the pumping element smaller than $L_1$ (5-40) and operating at a frequency v below $v_2=D/\lambda L_2$ ($>v_1$).

In some embodiments, the widths of the + and − electrodes in each pumping element may be chosen so as to bias pumping in one direction, while maintaining sufficiently fast charging of the surfaces, as shown in FIG. 5. For example, to pump from left to right in FIG. 2, the P−/+ pumping element must have it surface mostly covered by the electrode at the same voltage as B+, so its induced counter-charge in the diffuse part of the double layer in the fluid is positive (or negative) when the background field is directed from B+ to B− (or vice versa). This assumes nearly complete screening of the closely spaced electrode surfaces in the pumping element before the further separated background electrodes become significantly screened during each AC period, in the appropriate frequency range, $v_1 \leq y \leq v_2$. There will also be normal ACEO flow near the upper critical frequency, $v_2$, which can cause pumping with a variety of asymmetries built into the design of the pumping element.

Viewed from above, the two-dimensional geometry of the interlaced electrodes in the pumping element can be varied to adjust the frequency response, pumping rate, and/or mixing capability. In addition to parallel stripes (FIG. 5A), arms of the thin electrode can protrude into the adjacent thick electrodes in the direction along the channel (FIG. 5B) to shorten the electrode spacing and thus raise the upper critical frequency, $v_2$. Near this frequency, there will also be normal ACEO flow transverse to the channel, causing rolls that may be useful for mixing in the channel or passing particles in the fluid over a sensor on another wall of the microchannel. If the arms are tilted (FIG. 5C), there will be simultaneous mixing and pumping at high frequency, while still preserving a simple, plug-like pumping flow down the channel at low frequency (when all the electrodes in the pumping element are largely screened). The mixing can be optimized by taking advantage of chaotic streamlines from staggered chevron patterns (FIG. 5D).

Example 3

Pumping Elements Having Electrodes of Different Heights May Increase Flow Rate

In some embodiments of the invention, the flow rate is increased by altering the geometry of the various parts, such that the slipping surfaces work together to pump fluid in a single direction. According to this embodiment, raising all the surfaces pumping in the desired direction (and/or lowering the others) serves to "bury" reverse convection rolls. If the height difference is comparable to the width of the buried electrodes, the reverse convection rolls turn over near the upper surface and provide an effective "conveyor belt" for the primary pumping flow over the raised electrodes. In this way, the reverse flows actually aid the primary pumping flow, rather than hinder it; the resulting flow may exceed that of designs where the reverse flow is replaced by flat no-slip surfaces in a planar geometry.

Figure 5A:
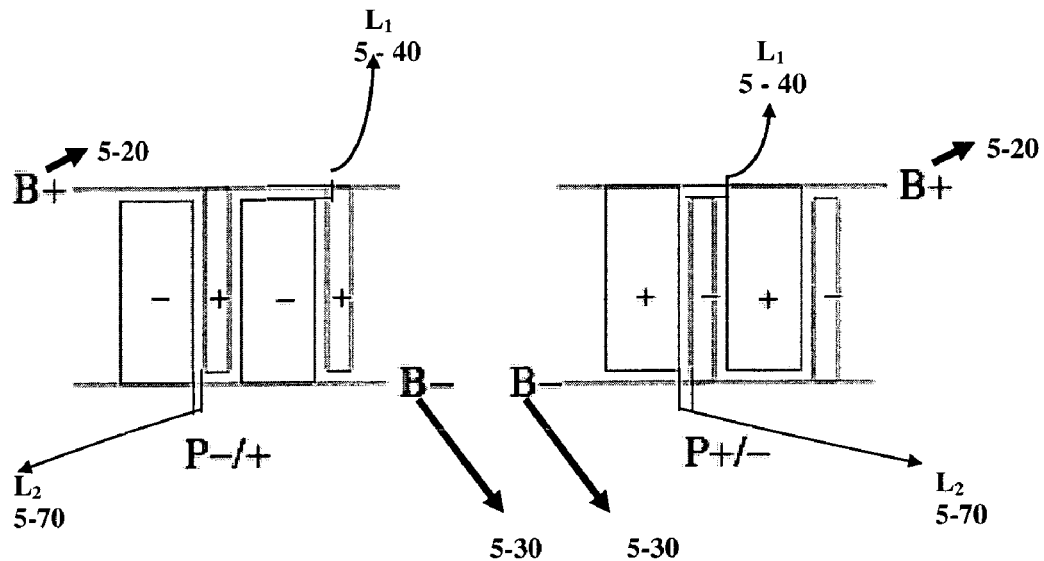
FIG. 5 schematically depicts a top/plan view of P+/− and P−/+ pumping elements with interdigitated + and − electrodes connected to the B+ (5-20) and B− (5-30) background electrodes, respectively. The simplest layout consists of parallel stripe electrodes (A), but more general interdigitated electrode geometries (B) are also possible to provide more flexibility in controlling the frequency response and the flow field. $L_1$ (5-40) represents the distance between the background electrode and pumping element, $L_2$ (5-70) the distance between the two electrodes in the pumping element. In particular, broken symmetry in the transverse direction (C) can cause secondary flows for mixing, in addition to the primary pumping flow down the channel.
Figure 5B:
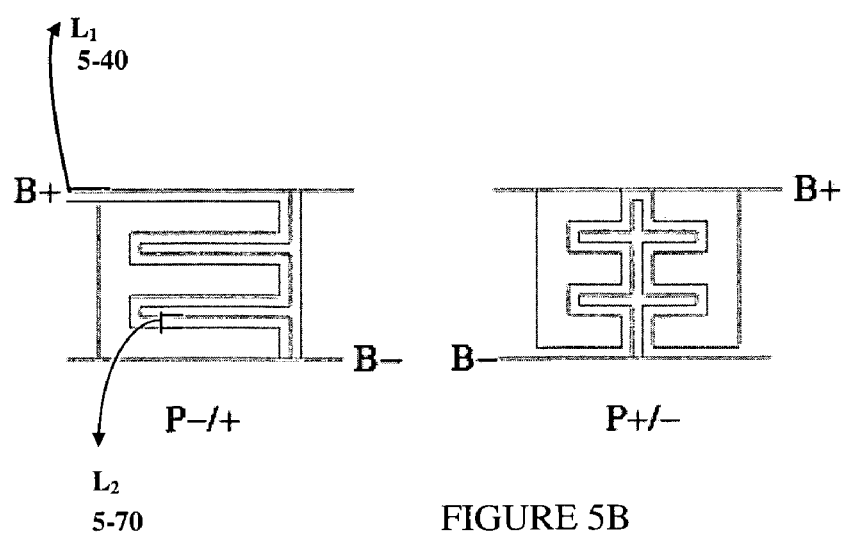
Figure 5C:
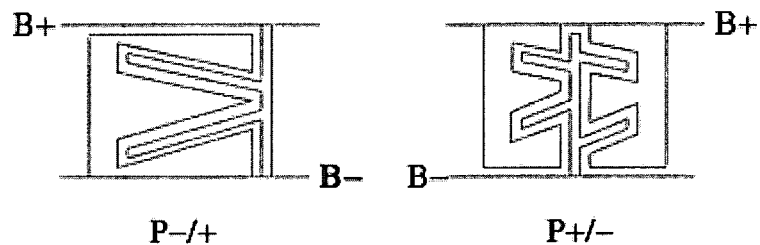
Figure 5D:
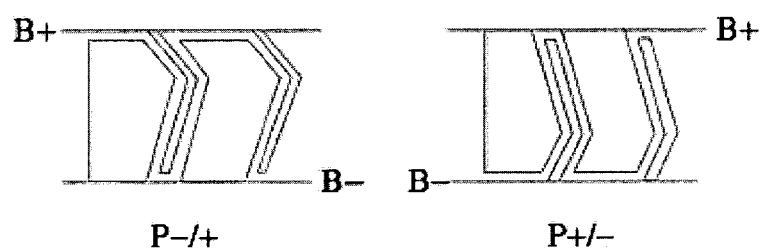

For example, with reference to the pumping element in FIG. 5A, consisting of planar interlaced parallel-stripe electrodes, which become nearly fully charged while a background electric field passes over the element to produce electro-osmotic flow. The background field could be steady DC, or alternating AC with a longer period than the charging time of the pumping electrodes.

Figure 6A:
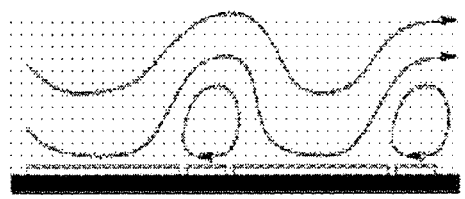
FIG. 6 schematically depicts a side view of embodiments of this invention comprising pumping elements with the plan layout of FIG. 5A, for time-averaged fixed-potential ICEO flow in an AC background electric field, showing planar geometry where reverse flows interfere with the primary pumping flow. A non-planar geometry with raised pumping electrodes where the long-range flow glides smoothly over a "conveyor belt" of recessed reverse convection rolls is shown in B.

A typical flow field above the pumping element comprising planar electrodes is depicted in FIG. 6A. With a planar geometry, the pumping flow must overcome and circumnavigate reverse convection rolls, as shown in the figure.

Figure 6B:
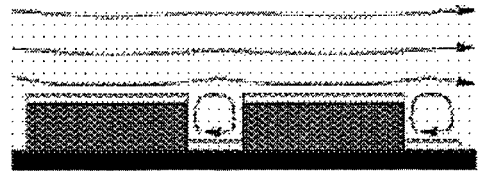

In one embodiment of this invention, the pumping electrodes are raised so as to recess the reverse convection rolls, as depicted in FIG. 6B. The pumping flow is then much smoother and straighter, streaming with little resistance over the recessed rolls (as on a conveyor belt), resulting in greatly enhanced pumping for the same voltage and electrode sizes.

Such modification can be made to any fixed-potential ICEO pumping-element designs, as described herein.

The characteristic scale of a convection roll in Stokes flow is a function of the geometry, so that the height of, in this embodiment, the raised pumping electrodes (or, in another embodiment, the depth of the recessed reverse electrodes) should be comparable to the width of the recessed electrodes (and vice versa). For each geometry, it is straightforward to perform experiments or simulations to determine the precise height at which the flow rate is maximized.

Recessed reverse convection rolls, furthermore, can act as traps for particles or molecules suspended in the fluid in a microfluidic device. If chemical reactions are initiated in a recessed region, then such a region can serve as a microreactor, and represents an embodiment of this invention.

The conveyor-belt principle as described can be applied to planar ACEO pumps with periodic arrays of pairs of two-level stepped electrodes.

Figure 7:
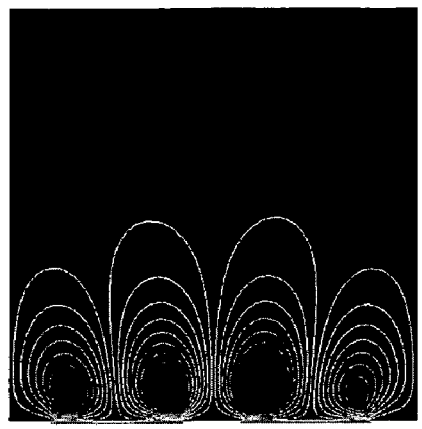
FIG. 7 demonstrates simulated time-averaged flow field for ACEO flow above a pair of symmetric planar electrodes in one period of a periodic array, as described.

For example, in a periodic array of symmetric electrode pairs, one spatial period of the time-averaged fluid streamlines at the frequency of maximum flow are as shown in FIG. 7, with the data consistent with that obtained based on simulations using a standard theoretical model [A. Ajdari, Physical Review E 61, R45-R48 (2000), A. Ramos, et al., Physical Review E 67, 056302 (2003), J. A. Levitan, et al., Colloids and Surfaces A 267, 122-132 (2005)]. The symmetric electrode pair exhibited the well-known pair of counter-rotating ACEO rolls as described by Ramos et al. [Journal of Colloid and Interface Science 217, 420-422 (1999)].

Figure 8A:
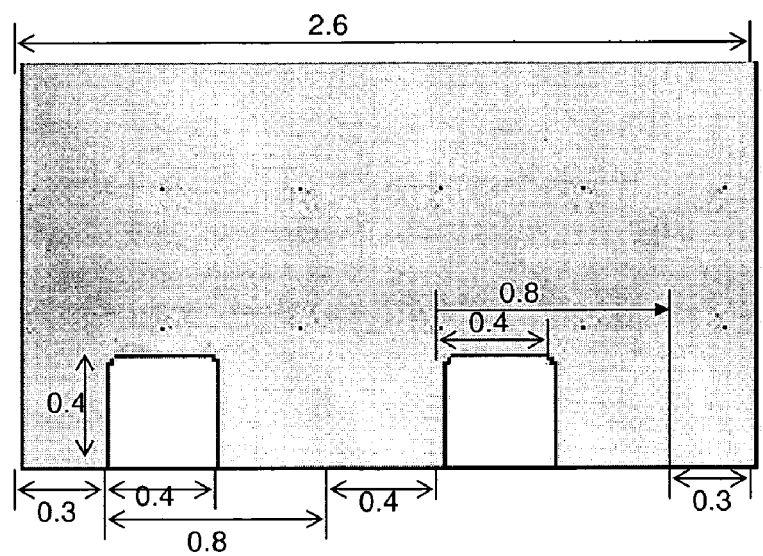
FIG. 8 demonstrates device designs, in which half of each electrode has been raised substantially (by half the electrode width) into the microchannel to create stepped electrodes. The geometry is shown in A and the simulated flow field in B.
Figure 8B:
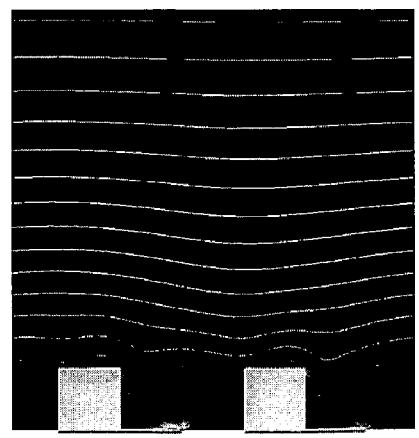

In some embodiments of the invention, the device comprises periodic pairs of symmetric electrodes by either (i) lowering the portions of the electrodes that pump in the undesired direction or (ii) raising the portions of the electrodes that pump in the desired direction. One embodiment of the latter design is as shown in FIG. 8A (in arbitrary length units, such as 10 microns=1 length unit), where the left half of each electrode in the pair is raised by half of the electrode width. The resulting asymmetric pair of stepped, multilevel electrodes takes advantage of the conveyor-belt effect to achieve a fast pumping flow driven by the raised portions, streaming over reverse convection rolls driven by the lower positions. This is illustrated by the simulated time-averaged flow at the peak frequency shown in FIG. 8B. Unlike the multi-level fixed-potential ICEO designs hereinabove, this pump has non-flat stepped electrodes, which also drive some electro-osmotic flow on the vertical sections.

Figure 9A:
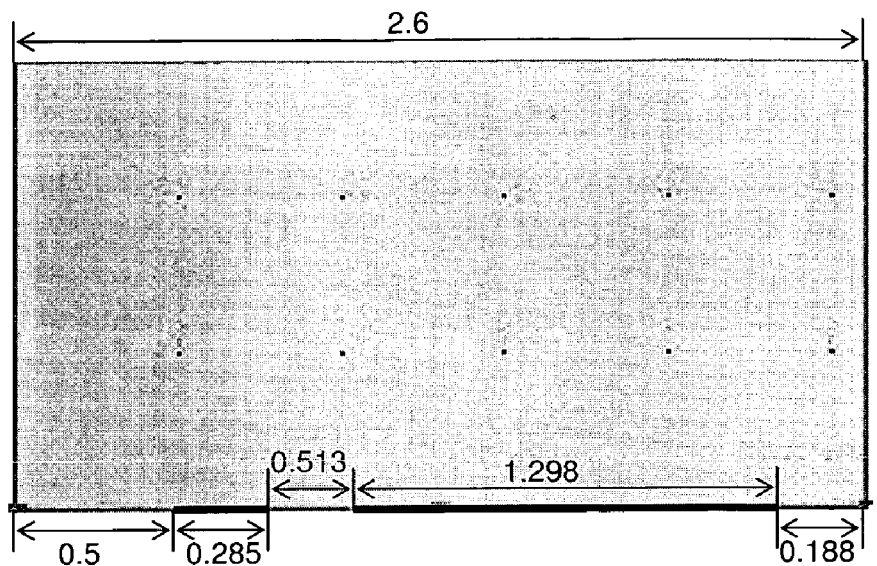
FIG. 9 demonstrates device designs, depicting the geometry (A) and simulated flow (B) for an ACEO pump with a periodic array of asymmetric pairs of flat electrodes.
Figure 9B:
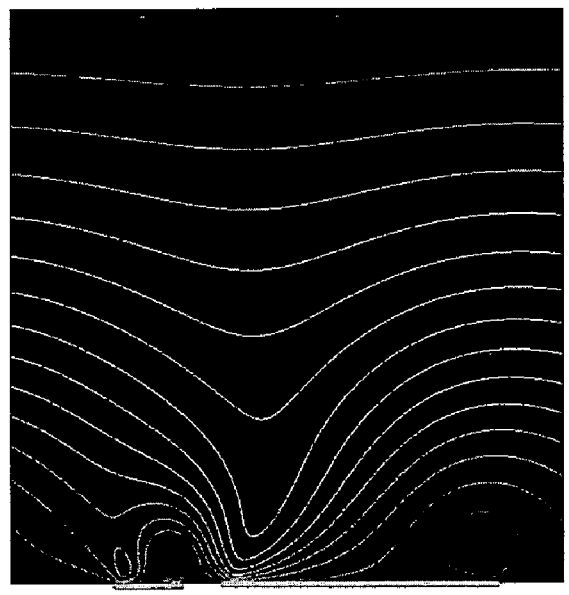

It is understood that the modification to the pumps for the devices of this invention may arise from any asymmetric planar electrode array. To illustrate this design procedure, for example, a planar periodic array of an asymmetric pair of electrodes as described in Studer et al. [V. Studer, et al., Analyst 129, 944-949 (2004)] was used. The geometry of the existing planar design is shown in FIG. 9A. The simulated flow field in FIG. 9B shows that pumping is achieved by an awkward competition between flow in the desired direction and reverse convection rolls above the surface.

Figure 10B:
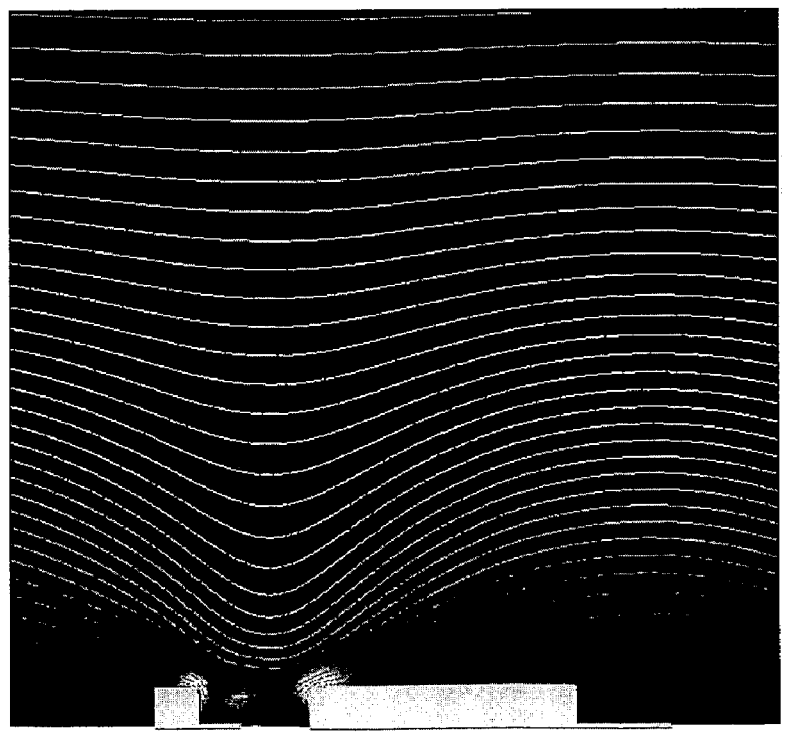

A much faster pump is obtained, however, when the design was altered to raise portions of the electrodes that pump in the dominant direction (up to stagnation points on each electrode), by a height comparable to the width of the unraised region. One embodiment of such a design is provided in FIG. 10A. The simulated flow field in FIG. 10B shows that the conveyor-belt principle applies again, as the reverse rolls have been recessed below a fairly smooth pumping flow, which is aided by the reduced hydrodynamic resistance of the tops of the reverse rolls.

Figure 11:
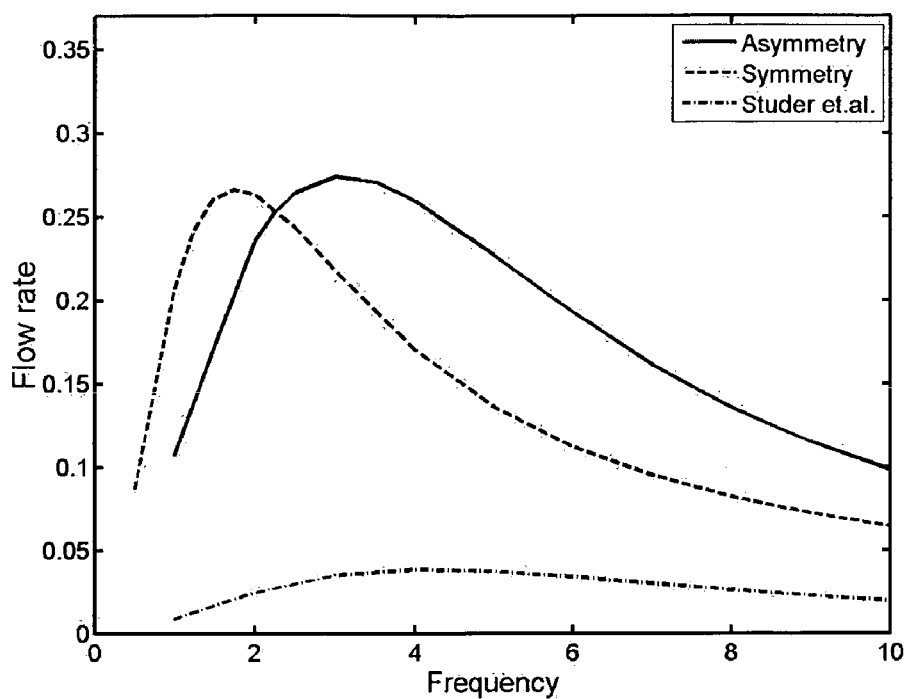
FIG. 11 demonstrates a simulated flow rate (arbitrary units) versus AC frequency for the designs in FIG. 8 ("Symmetry"), FIG. 9 ("Studer et al"), and FIG. 10 ("Asymmetry").

The simulated time-averaged flow rate versus AC frequency (at the same voltage and spatial period) is shown in FIG. 11 for the examples in FIGS. 8 to 10. The frequency response has a somewhat different shape in each case, although still roughly the same profile, however, designs using non-planar stepped electrodes have maximum flow rates roughly ten times faster than the planar design of Studer et al. (FIG. 9), which is currently thought as one of the fastest known ACEO pump and nearly optimal for planar arrays.

Figure 12:
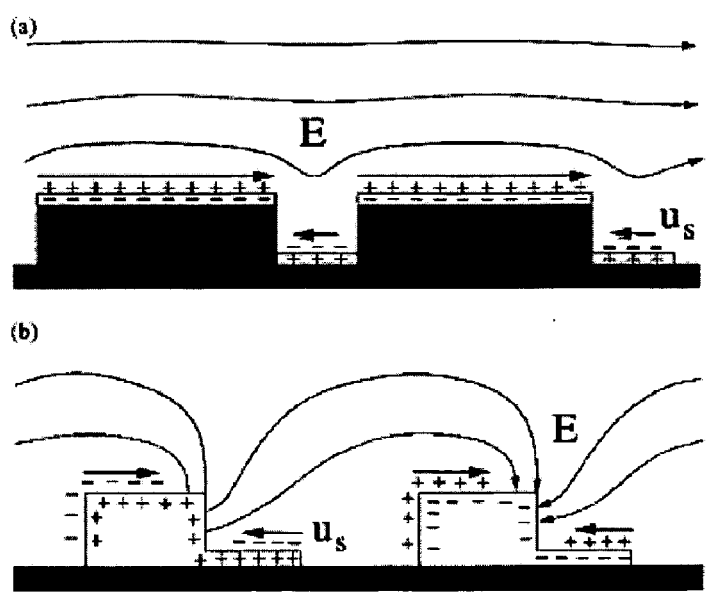
FIG. 12 depicts embodiments of devices of this invention. ICEO slip (thick arrows, $v_s$) producing a flow driven by the electric field (solid curves, E) acting on induced diffuse-layer charge (+, −) on electrodes (polarized as +, −) in a periodic array. (a) Fixed-potent potential ICEO driven by a DC or AC background electric field (applied at more distant, unscreened electrodes, not shown) over fully screened pumping electrodes. (b) ACEO at the resonant frequency, where each electrode is partially screened at its edges, while supplying the electric field from its center.

Differences in induced flow rates may be understood by considering ICEO flow involvement of non-uniform polarization of the double layer, and thus a non-uniform electro-osmotic slip distribution, in response to an applied electric field (FIG. 12).

In symmetric situations, the contributions of opposing slip cancel to produce no net electrophoretic motion or long-range fluid pumping, respectively, for a metal colloidal sphere in a uniform DC or AC electric field or a symmetric pair of electrodes applying an AC voltage. Net pumping by ACEO at electrode arrays can only be achieved by breaking spatial symmetry in each period. Broken symmetry is also required for induced charge electrophoresis of polarizable (conducting or dielectric) colloids. For this reason, it would seem that ICEO is inherently inefficient for fluid pumping over a surface (or electrophoretic motion), since the surface-averaged slip will always be much smaller than the maximum slip, due to the cancellation of opposing velocities. Certainly, this is the case with existing planar ACEO pumps, where ~mm s$^{-1}$ maximum velocities yield only ~100 μm s$^{-1}$ surface averaged slip velocities. This invention, however, provides a rationale for enhancing pumping ability, since as demonstrated herein, the former only applies to flat surfaces, where the opposing slip regions are aligned in maximal competition.

This invention demonstrates that in three dimensions, it is possible to design surfaces of nonuniform slip where essentially every region of the surface contributes to fluid pumping in a single direction. The simple principle, which applies to any situation of nonuniform slip is to raise regions pumping in the desired direction and recess regions of reverse slip. For an appropriate choice of the step height, the vortices driven by reverse slip on the recessed surfaces will recirculate near the level of the raised surfaces.

One embodiment of this rationale is shown in FIG. 12(a), where a background electric field (supplied by more distant, unscreened electrodes) passes over a surface with raised and lowered steps of alternating diffuse-layer charge (or zeta potential) to create the slip profile and flow in FIG. 12(b). The stepped electrodes enable achievement of diffuse-charge distributions as depicted through capacitive coupling by appropriately controlling the voltages in an AC (or DC) background electric field. The resulting fixed-potential ICEO flows drive fluid pumping in a dominant direction.

Electrical connections may involve grounding the raised electrodes to one background electrode (supplying the electric field) and the lowered electrodes to the other background electrode, as described. The pump would operate in the range of AC frequencies where the stepped electrodes become fully screened by diffuse charge, while the background electrodes remain unscreened.

Similarly, ACEO may be envisioned using partially-screened electrodes, which also supply the electric field, near the resonant RC frequency. In this case, the electric field is larger than in fixed-potential ICEO designs, for the same applied voltage, since there is no need to separate the background and pumping electrodes. ACEO flows at planar electrode arrays are generally strongest near the electrode edges and directed toward the electrode centers. It is natural therefore to raise the portion of the each electrode pumping in a desired direction (or lower the other portions) to create a fluid conveyor belt. As shown in FIG. 12(b), the charge and slip profiles are more complicated than with fixed-potential ICEO at fully screened electrodes, but the conveyor-belt principle leading to efficient pumping in one direction is the same.

With 3D electrode structures, the electric field can be manipulated to a greater degree, e.g. by introducing field singularities at corners and confined local "channels" for the electric field. In the regions of greatest slip, the electrode surface is fully screened and acts like an insulator. In a planar geometry, the electric field is bounded, but at a protruding corner it becomes singular. For example, in FIG. 12(a), the raised electrode makes an angle of $3\pi/2$ with the side wall, so the electric field has an insulating-corner singularity of $E \sim r^{1/3}$. In FIG. 12(b), the same singularity occurs at the outer corner of the raised electrode surface, which amplifies the pumping flow. The geometrical confinement of the electric field emanating from the recessed surfaces and side walls enhances its strength before it fans out over the raised electrodes.

Three-dimensional geometry can also affect the double-layer charging process and thus the frequency spectrum of ACEO flow. For example, the edge of an electrode on a flat insulating surface has an initial field singularity, $E \sim r^{-1/2}$, which locally accelerates double-layer charging prior to complete screening. For a raised electrode with an insulating side wall, as in FIG. 12(a), the field singularity is enhanced, $E \sim r^{-}$ 2/3, so the charging will occur more quickly, thus shifting the decay of ACEO flow to higher frequencies.

For a stepped electrode with conducting side walls as in FIG. 12(b), the initial singularity is weaker, E~$r^{-1/3}$, but after double-layer polarization the field remains singular, E~$r^{-1/3}$, as noted above.

To compare different pump designs, a commercial finite-element package (FEMLAB) was utilized, to solve the standard model equations for ICEO flows in weak electric fields with thin double layers, and simulations were conducted as described in Example 2.

The maximum slip velocity arises at the edges and is directed toward the center of each electrode. These converging flows meet at a stagnation point at the center and recirculate into the bulk. If the channel has a finite height, the streamlines close to form a vortex pair over each electrode.

As described herein, to create pumping in a dominant direction, it is possible to lower the electrode regions slipping to the opposite or raise those slipping to the right. In both cases, the goal the recess of the non-dominant slipping vortex recirculates fluid and dominant-slipping surfaces enhance pumping in the dominant direction. While changing the electrode geometry affects the electric field and induced double-layer charge, and thus the slip velocity distribution, it is not qualitatively different from that of planar geometry, where fluid is sucked in from the edge of each electrode toward the central region, where it is ejected into the bulk.

Figure 13:
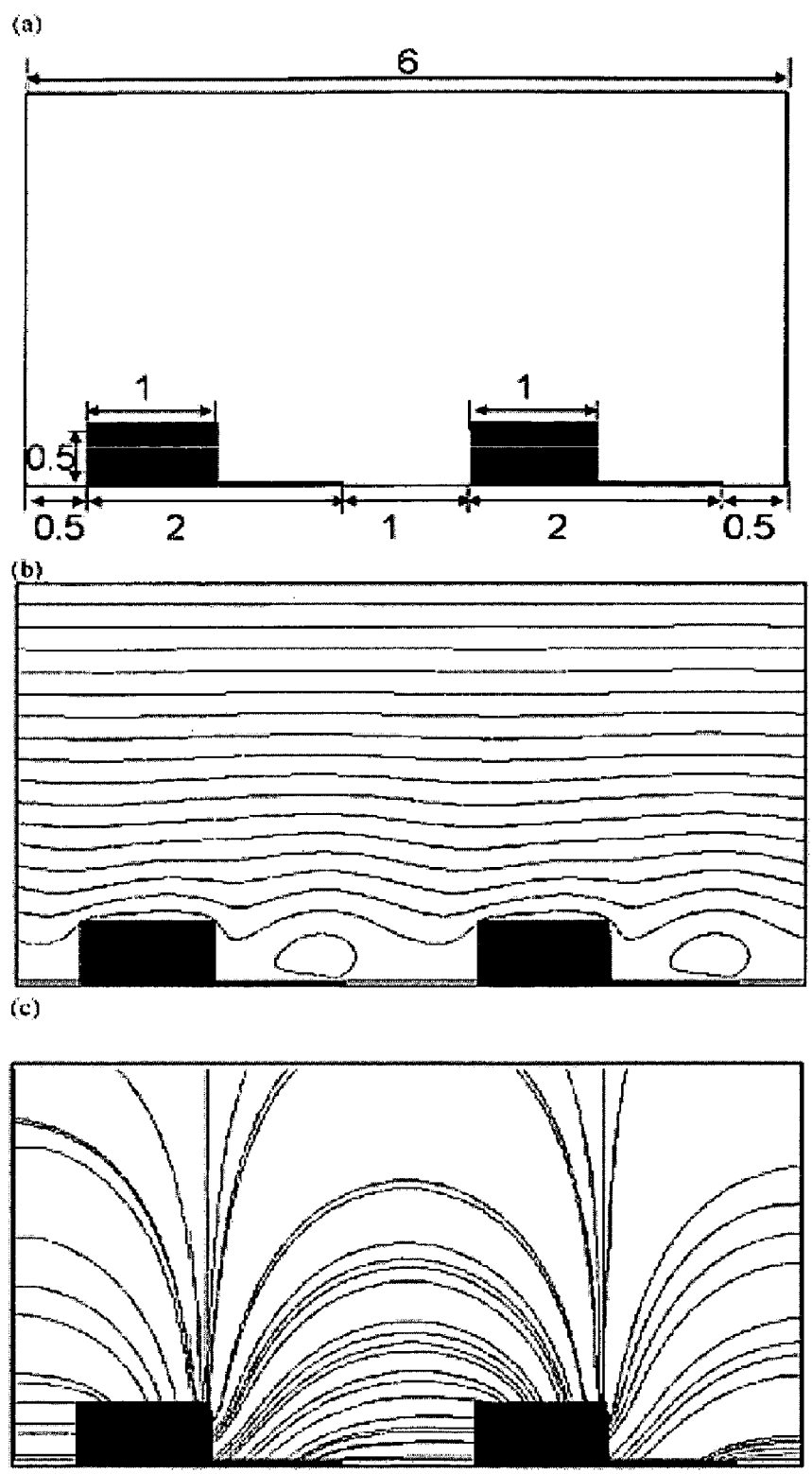
FIG. 13 depicts the simulation on of a 3D ACEO pump with a periodic array of stepped electrodes of alternating polarity in space and time. The geometry, shown in (a), has gaps and step widths all equal to minimum feature size L, so the horizon horizontal array period is 6 L. The channel height is 20 L, far beyond the range shown above. The length L sets the scales for velocity $U=\in V^2/\eta L(1+\delta)$ and electric field $E=V/L$. Simulation results are shown for AC frequency $\overline{\omega}=1/\tau$, near the maxim maximum flow rate, where $\tau=\lambda L/D$ $(1+\delta)$ is the "RC" charging time. The time-averaged fluid streamlines (b) clearly show a fluid conveyor belt, and the electric field in phase with the voltage peaks (c) resembles that of FIG. 12(b).

In this aspect, the height difference between the electrodes should be roughly equal to the width of the recessed slipping region, since Stokes flow has no intrinsic length scale. FIG. 13a demonstrates an embodiment, whereby a left half of each electrode is raised in a symmetric array by one quarter of its width. As shown in FIG. 13b for $\omega=1/\tau$, this successfully creates a fluid conveyor belt pumping from left to right. The electric field lines in phase with the AC forcing (real part of the complex amplitude), shown in FIG. 13c, indicates electrode polarization.

To test the efficiency of this aspect, simulations of planar ACEO pumps, were conducted in comparison to the aforementioned 3D design.

Figure 14:
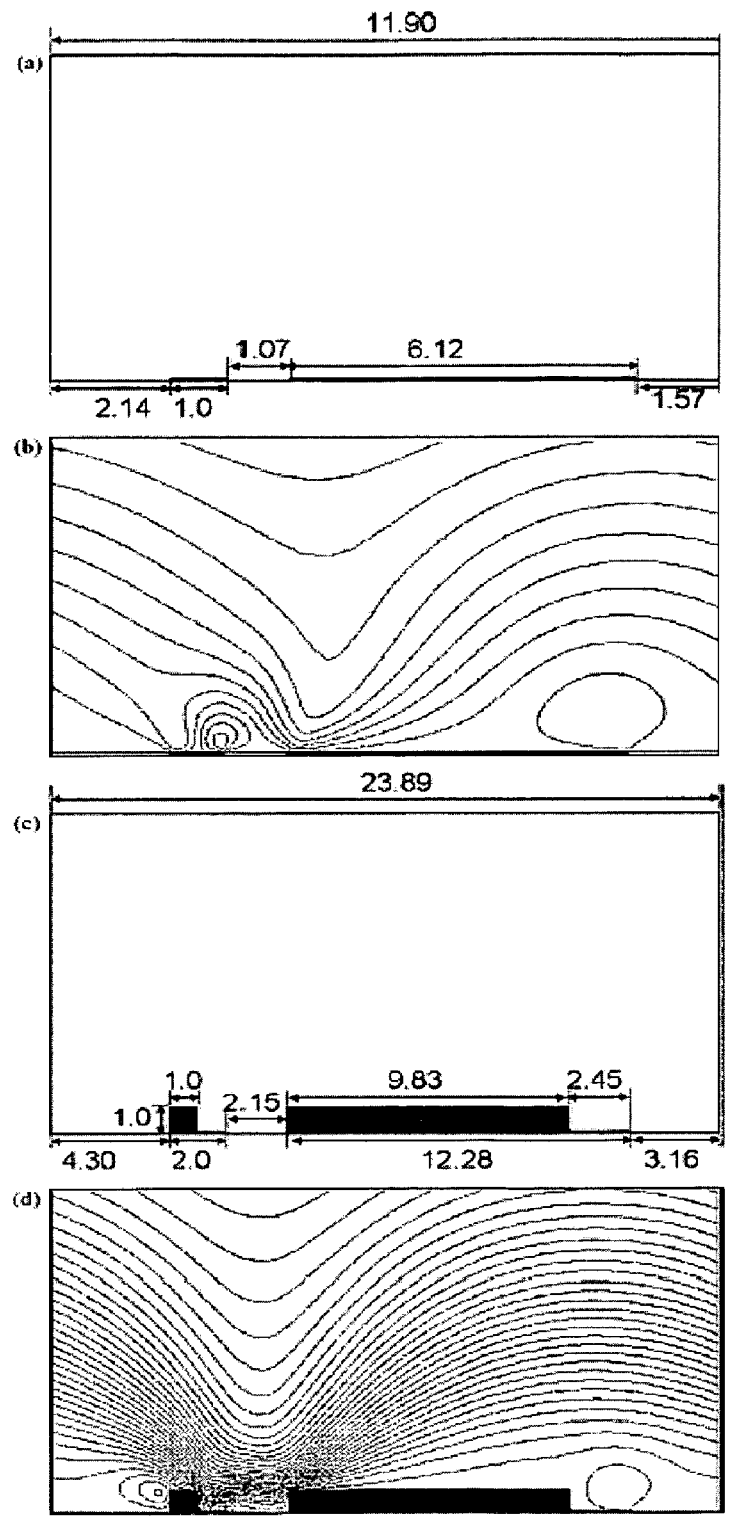
FIG. 14 depicts the geometry (a) and simulated time-averaged streamlines (b) for previous planar ACEO pumps (A. B. D. Brown, et al, Phys. Rev. E, 2001, 63, 016305; M. Mpholo, et al, Sens. Actuators, B, 2003, 92, 262; A Ramos et al., Phys. Rev. E, 2003, 67, 056302; V. Studer, et al. Microelectron. Eng., 2003, 61, 915; V. Studer, et al, Analyst, 2004, 129, 944) for $\overline{\omega}=1.0/\tau$, the optional frequency reported. The spacings and sizes of the electrode pair are asymmetric, which leads to long-range pumping from left to right, primarily driven by the larger electrode. The minimum feature size L is the width of smaller electrode, so the array period is 11.90 L. The geometry (c) and simulated flow (d) are also shown for an embodied design with stepped electrodes made by raising portions of the planar pump in (a) up to the stagnation points. The geometry is rescaled horizontally to set the minimum feature size L to the width of the smaller step, which results in a larger period of 23.89 L. In both simulation simulations, s, the channel height is again set to 20 L.

The planar design is depicted in FIG. 14a. The streamlines are shown in FIG. 14b $\omega=1/\tau$. The flow profile indicates long-range flow is achieved by tortuous streamlines, which must bypass reverse vortices, which is inefficient, and the surface-averaged slip velocity (which sets the flow rate in an effective Poiseuille flow for a channel with a nonuniform slip distribution) is orders of magnitude smaller than the maximum slip velocity.

Figure 15:
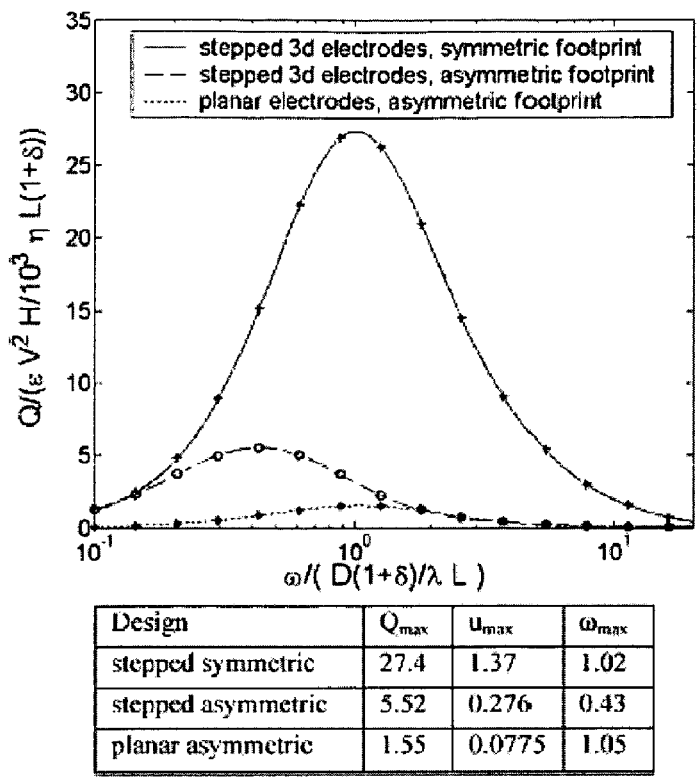
FIG. 15 demonstrates the flow rate versus frequency in dimensionless variables for the 3D ACEO pumps depicted in FIG. 13(a) and FIG. 14(c), compared with the standard planar pump in FIG. 14(a). The smooth curves are cubic splines through the simulation points. The table shows the flow rate $Q_{max}$, typical bulk velocity $v_{max}=Q_{max}/H$, and frequency $\overline{\omega}_{max}$ of maximum pumping for each design. For typical experiments (L=5 mm, V=1 V, $\lambda$=10 nm, D=0.5×10$^{-5}$ cm$^2$ s$^{-1}$), $v_{max}$ is scaled to 140 μm s$^{-1}$ and $\overline{\omega}_{max}$ to 10 kHz. For a microchannel of height H=100 μm and width 500 μm, $Q_{max}$ is scaled to 7 nL s$^{-1}$. (These estimates neglect surface capacitance, $\delta$=0).

3D designs as shown in FIG. 15, however provide for dramatically increased flow rate. Without any geometrical optimization, the stepped electrode array of FIG. 13 achieved a maximum flow rate of $Q_{max}=27.4\times10^{-3}$ UH, which is 17.6 times larger than that of the planar pump, $1.55\times10^{-3}$ UH. The peak frequency max was only slightly shifted, from $1.05/\tau$ for the planar pump to $1.02/\tau$ for the stepped pump.

For typical experimental conditions (L=5 μm, V=1 V) in aqueous solutions ($\lambda$=10 nm, D=$0.5\times10^{-5}$ $cm^2 s^{-1}$, $\in$=$7\times10^{-5}$ g $cm V^{-2} s^{-2}$, $\eta$=0.01 g $cm^{-1} s^{-1}$), the stepped pump has a mean velocity $v_{max}$=190 μm $s^{-1}$ and frequency $\overline{\omega}_{max}$=10 kHz at the maximum flow rate. The planar pump has almost the same peak frequency, but a much smaller velocity $v_{max}$=11 μm $s^{-1}$. For a microchannel of cross sectional height H=100 μm and width 500 μm, the stepped pump has a flow rate of 9.6 nL $s^{-1}$, compared to 0.54 mL $s^{-1}$ for the planar pump. With somewhat smaller feature sizes and/or geometrical optimization, the simulations suggest that mm $s^{-1}$ mean velocities should be attainable, while still applying only a few volts at 10-100 kHz.

Such velocities are comparable to traditional pressure-driven micro-flows and scale favorably with miniaturization. FIG. 14c, modifies an asymmetric planar pump of FIG. 14a by raising the portion of each electrode with slip in the pumping direction by a distance equal to half the smaller gap between electrodes. The horizontal length was also rescaled so that the minimum feature size L was the width of the smaller step. As shown in FIG. 15, this design has a flow rate $Q_{max}$=$5.52\times10^{-3}$ UH, which is four times faster than the planar asymmetric pump, although five times slower than the stepped design in FIG. 13 with a symmetric footprint (for the same minimum feature size). The asymmetric-footprint pump also has a lower peak frequency $\overline{\omega}$max=$0.43/\tau$ than some of the other embodiments described herein.

Example 4

Increased Flow Rate in Devices of this Invention

Several example geometries were microfabricated and systematically tested in comparison with a well-characterized planar pump geometry in a microfluidic loop. Microfabrication of the 3D electrodes was accomplished by patterning sputtered metal interdigitated electrodes, with width 20 μM and spacings between electrodes of 5 μm, on transparent glass substrates. In contrast with traditional planar ACEO pumps, an electroplating process was then employed to create stepped 3D geometries, with step widths of 15 μm and heights of 2.7 μm. Heights in the range of 1-5 μm were typically prepared, which all showed a comparable improvement in pumping performance over planar pumps.

The step height was controlled by adjusting the plating time. The step height was limited only by the thickness of photoresist used as a plating mask, although simulation suggested it was not necessary to create very tall steps to break symmetry. The 3D ACEO pumps were then capped with polymer devices containing microchannels to study the fluid flow.

The interdigitated electrodes were aligned within the microfluidic loop containing de-ionized water and fluorescent latex spheres were injected into the fluid loop opposite the electrodes to avoid electrophoresis of the spheres. Velocities were extracted from tracer particle motion at a variety of applied ac voltages and frequencies. For comparison, devices with planar ACEO geometry, with electrode widths of 4.2 and 25.7 μm and spacings between electrodes of 4.5 and 15.6 μm, were fabricated and tested using similar methods. The dimensions of the 3D ACEO pump were set to have the same 50 μm period between complementary electrode pairs as the planar pump.

Figure 16:
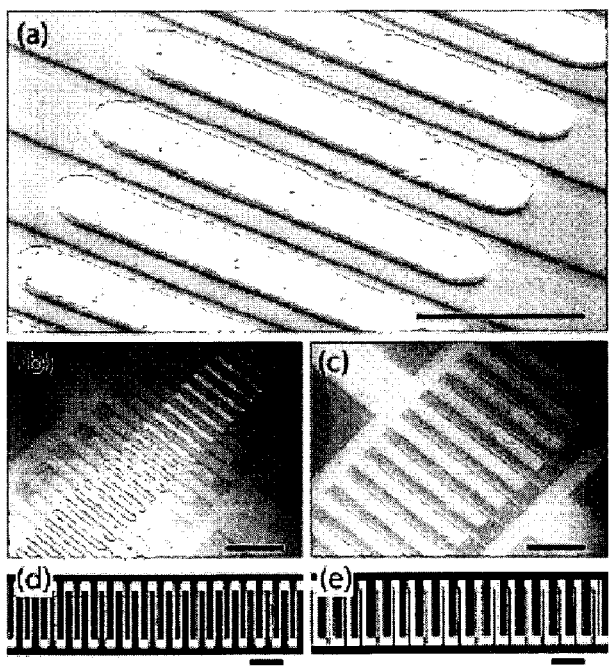
FIG. 16 depicts an embodiment of a device of this invention and a previous planar device. (a) Detail of three dimensional electroplated steps on the interdigitated electrodes. The gold electrodes are patterned on a quartz substrate. Scale bar indicates 50_m. The comparison between (b) nonplanar and (c) planar pump geometries clarifies a pumping lane. These ACEO designs are aligned within a PDMS microfluidic channel for characterization as pictured in (d) and (e). Scale bars in (b)-(e) indicate 100 μm.

FIG. 16 shows scanning electron micrographs of (a) the electroplated regions on planar substrates, and in (b) and (c) comparative images of the nonplanar and planar geometries, respectively. Further, (d) and (e) show photomicrographs of the planar and nonplanar geometries capped with polydimethylsiloxane (PDMS) loops.

Figure 17:
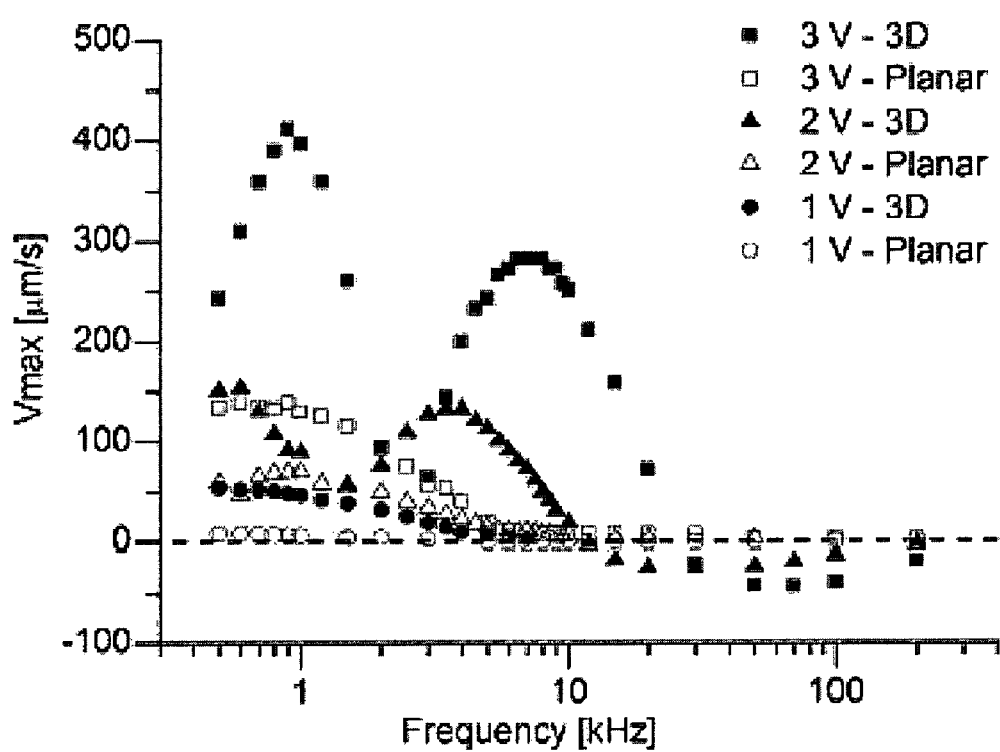
FIG. 17 plots fluid velocity as a function of applied voltage (peak to peak) and frequency in planar (open symbols) versus non planar (solid symbols) devices.

Plots of centerline fluid velocity versus frequency at various peak to peak voltages (V) were obtained (representative plots shown in FIG. 17). Some embodiments of nonplanar pumps of this invention were compared to previous planar designs. The peak velocity at 1 V was 10 μm/s for the planar device, in marked contrast to the much more rapid 55 μ/s for nonplanar devices of this invention.

At 2 V, the planar device demonstrated a peak velocity of 75 μm/s vs 150 μm/s for nonplanar devices, while at 3 V, the planar device showed a peak velocity of 150 μm/s vs 420 μm/s for nonplanar devices of this invention.

In all cases, the peak performance of the nonplanar device was faster than previous planar devices, and at 1 V exceeded the planar device by a factor of 5. The upper critical frequency for forward pumping in the nonplanar device increased substantially with voltage to allow a much broader band of operation. While the planar device pumping performance decayed quickly at frequencies above 1 kHz, the performance of the nonplanar designs demonstrated significant fluid velocity at 10 kHz for the higher voltages. Further, the performance of the nonplanar pumps improved as frequencies exceeded 4 kHz. At these higher frequencies, the difference in velocity between planar and nonplanar devices becomes quite dramatic. For instance, at 2 V and 4 kHz, the planar device exhibited a velocity of 40 μm/s and the nonplanar device exhibited velocity of 140 μm/s. Further, at 3 V and 10 kHz, the planar device demonstrated a velocity of 10 μm/s, whereas the nonplanar device demonstrated a velocity of 275 μm/s, a factor of 27.5 difference.

Changing the height of the pumping electrodes, as demonstrated herein, significantly enhanced fluid flow. Symmetric planar electrode arrangements, in marked contrast, did not generate directional flow. The nonplanar pumps also displayed a much larger frequency range, which could be useful in many applications.

Example 5

Additional Embodiments of Devices of this Invention

Figure 18A:
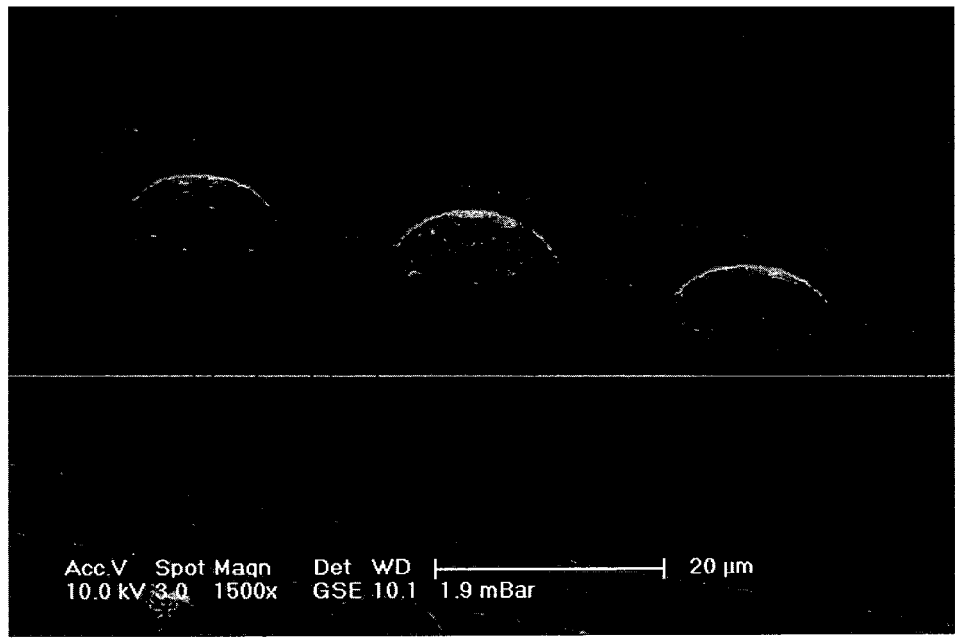
FIG. 18 is a scanning electron micrograph (SEM) of gold cylinders grown on planar gold electrode arrays, representing an embodiment of electrodes, which may be used in a device of this invention.
Figure 18B:
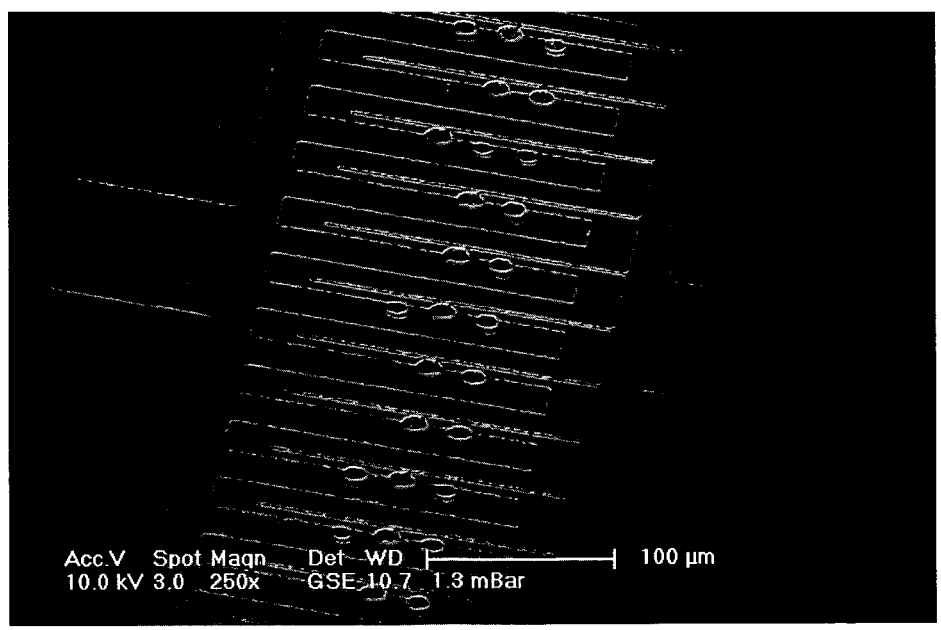

Other electrode geometries may be envisioned, which in turn may modify the induced flow. Some embodiments of such geometries includes use of a cylindrically-shaped electrode (FIG. 18), curved step electrodes, and other similar geometries, which are expected to modify the flow, for example, by reducing shear and hydrodynamic dispersion at the side walls of the channel.

Figure 19:
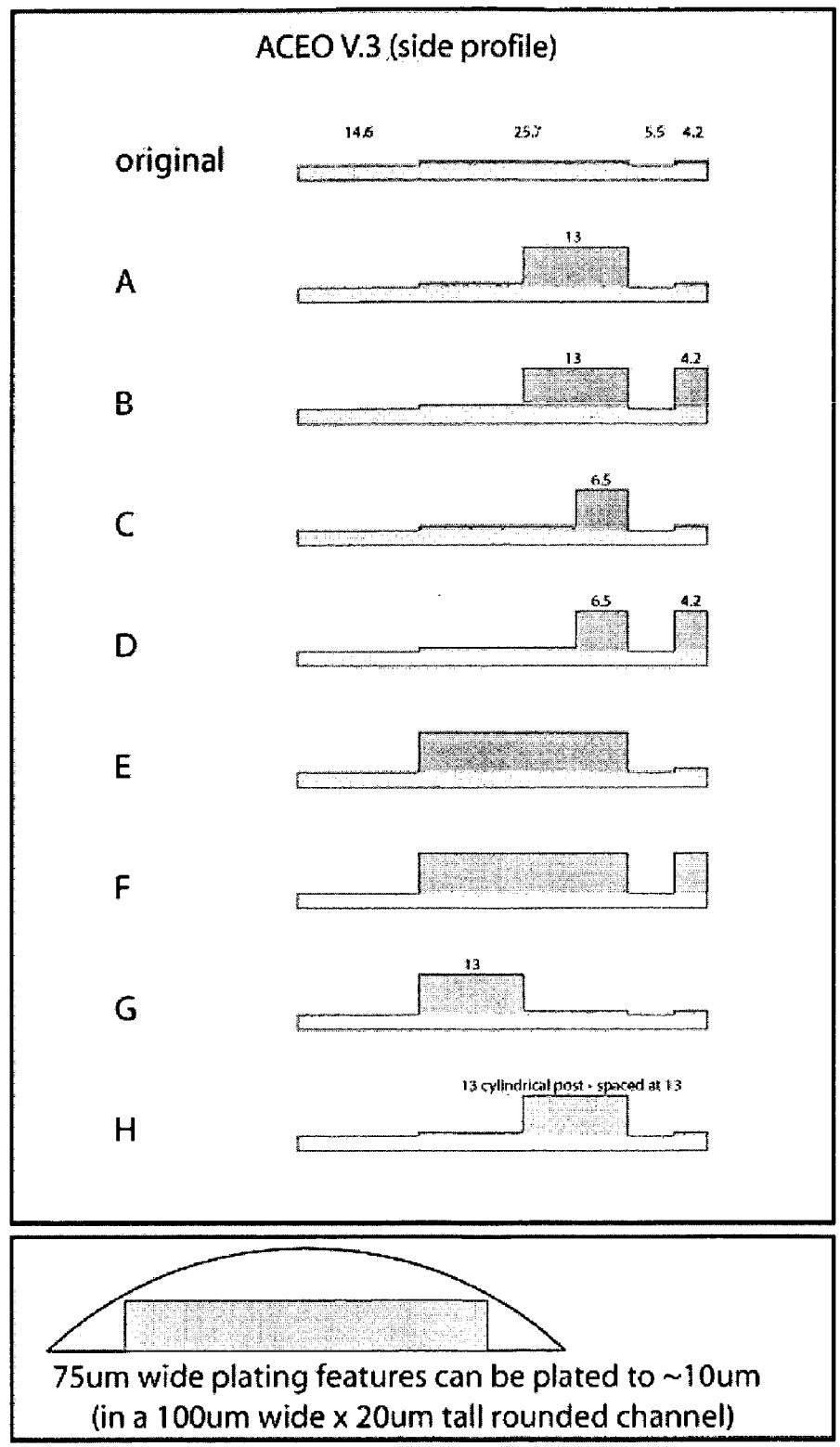
FIG. 19 schematically depicts side views of embodiments of stepped electrodes in one period of one embodiment of a parallel-stripe array micropump. Also shown at the bottom is a cross section of an embodiment of a microfluidic channel, made by soft lithography from PDMS FIG. 20A schematically depicts an embodiment of a chip design for a microfluidic loop.
Figure 20A:
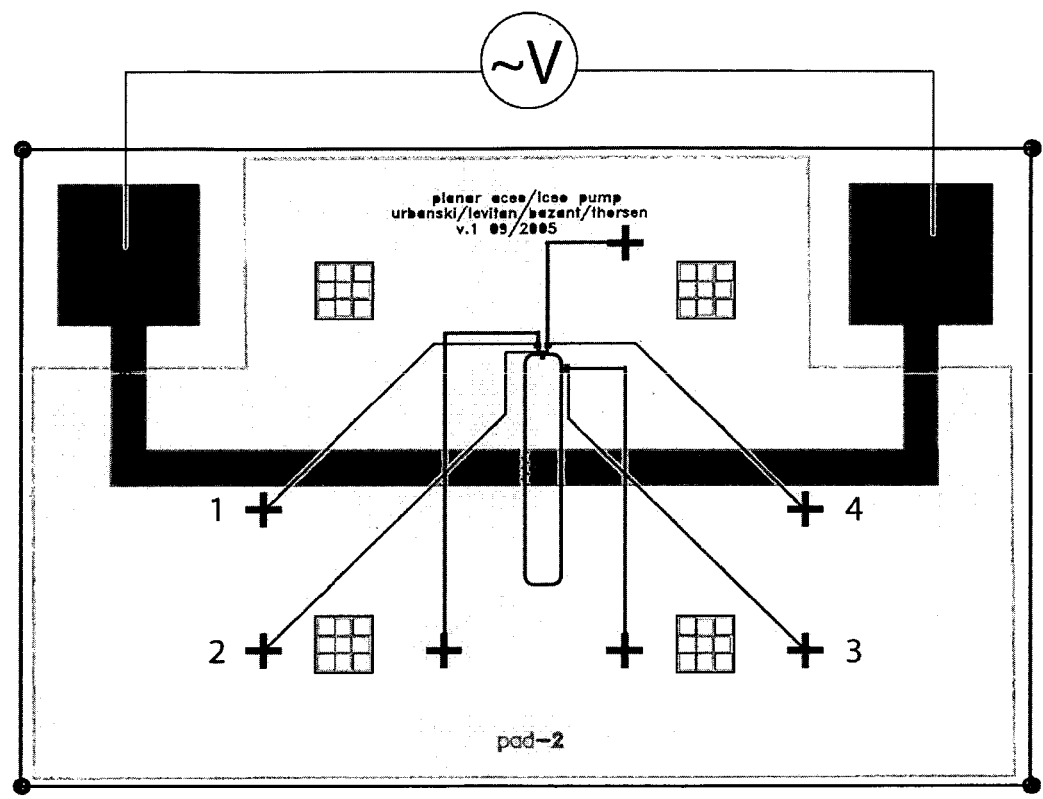
FIG. 20B is an annotated photo of an embodiment of a microfluidic loop and chip with soft-valving for flow controls.
Figure 20B:
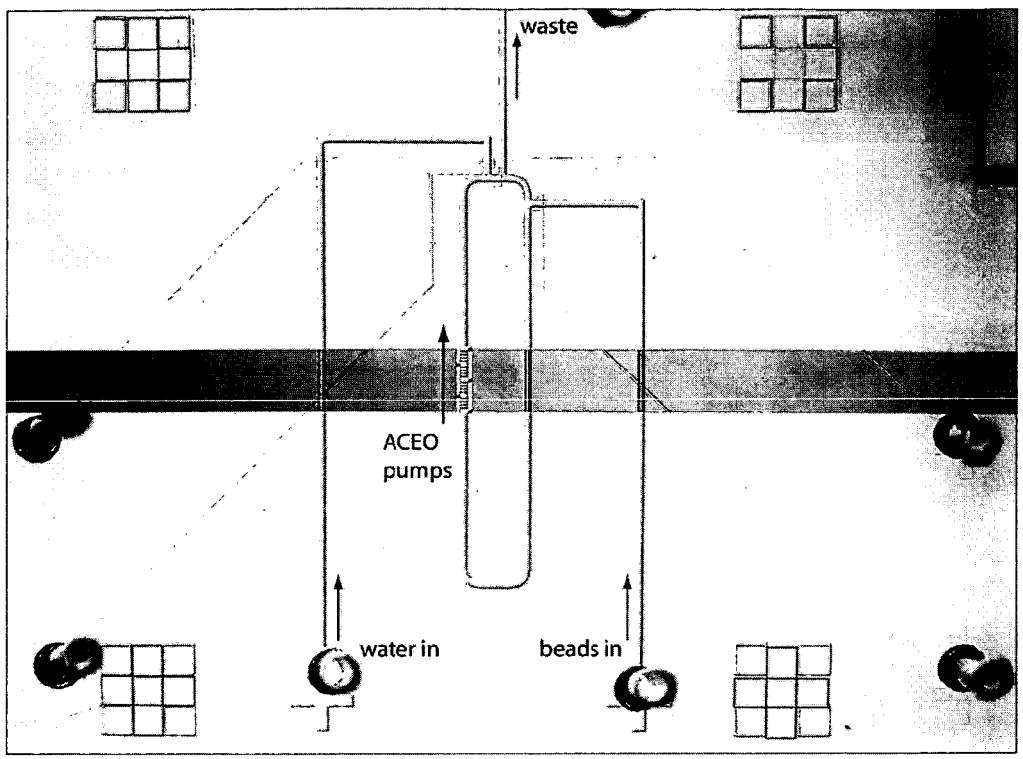

In addition, other embodiments of device designs as described in Examples 1-4 are presented (FIG. 19), as well as a chip design for a microfluidic loop, including soft-valving for flow controls (FIG. 20).

In some embodiments, altering the electrode or pumping element geometries, for example, may facilitate mixing of fluids introduced into the device, for example, in a direction transverse to that of the dominant flow.

Example 6

Additional Embodiments of Devices of this Invention

Materials and Methods

Pump Fabrication

The electrokinetic pumps were fabricated using a series of photo-patterning, etching, and electroplating steps. A 50 nm adhesion layer of chrome, followed by a 50 nm layer of gold was deposited by e-beam evaporation onto 4-inch borosilicate glass wafers which had been previously cleaned in a piranha solution (1:3 solution of hydrogen peroxide and sulfuric acid) for 20 minutes and roughened in a barrel asher for 2 minutes. The planar electrode structures were created by etching patterns with gold and chrome etchants, defined using standard positive resist photolithography (OCG 825) and a high resolution chrome mask. Three dimensional structures were created using a secondary photolithography and electroplating process. A second mask was aligned to base features, and a thick photoresist (10 μm, AZ 4620) is patterned for electroplating. Steps were electroplated to a desired height using gold solution (Orotemp 24C, Technic, Inc.) and the residual photoresist was stripped using acetone and isopropanol. The plating height was varied by adjusting the electroplating current and time. Individual rectangular devices were die-sawed, and, prior to testing, bare copper leads were attached using conductive silver epoxy. The resulting heights of the three dimensional structures were measured using a white light interferometer (Zygo Corp.).

Microfluidic Devices

Figure 21:
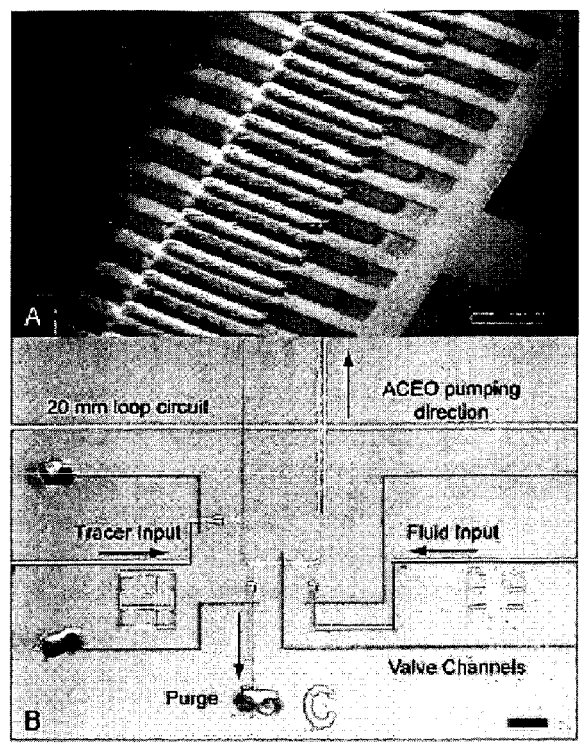
FIG. 21 depicts another embodiment of a device of this invention. (A) Scanning electron microscope image of a 3D ACEO pump comprised of interdigitated gold electrodes patterned on an insulating substrate. The scale bar indicates 100 mm. (B) The microfluidic device containing an integrated pumping loop with rectangular channels allows for repeatable characterization of different 3D ACEO pumps. When an alternating voltage is applied to the electrodes, the fluid is pumped in the counter clockwise direction within the closed circuit. Fresh operating fluid is loaded to the loop over the pumps, and tracer particles are input to the bottom left hand corner before every velocity measurement. The scale bar indicates 1 mm.

A microfluidic chip was designed to systematically study the performance of the various pump designs, following a similar methodology described previously by Studer et al. [Analyst 129 (10) (2004), 944-949.]. The devices were comprised by an assembly of the base glass substrate containing patterned electrodes, capped with a multilayer soft lithography (MSL) polydimethylsiloxane (PDMS) microfluidic device[Unger, et al. Science 288 (5463) (2000), 113-116]. On chip valves isolate fluid flow due to electrokinetic pumping from external pressure perturbations and were controlled using off chip pressure regulators. The testing loops had a circumference of 20 mm, and pump lengths were 5 mm. Microfluidic devices of this invention may be created using multilayer soft-lithography [M. A. Unger, supra]. The PDMS device was designed to allow channels of rectangular cross section to be used in the pumping loop. Previous studies using an enclosed loop [Studer, supra] relied on "push-down" MSL valves, which necessitated rounded flow channels. Rounded channels complicate fluid flow profiles, place a limit on the height of fluid channels which may be tested, and are not adequate for accommodating tall rectangular electroplated structures. The present design utilized internal interconnects between rectangular and rounded channels on two device layers, created by punching small holes in the thin PDMS membrane. In this manner, rectangular channels on the base layer may be used to create "push-up" valves to control fluid flow into the loop, and pressurized fluids were routed from rounded channels in and out of rectangular channels below. Rectangular channels of arbitrary height may also be tested within such loops in order to study the effects of electric field confinement on pumping [L. H. Olesen, et al., Phys. Rev. E 73 (5) (2006), 056313.]. The injection layer mold was fabricated using a positive resist (AZ 4620, Clariant) on a silicon wafer, which was reflowed after development to create molds of rounded cross section. Flow molds were created using a negative photoresist (SU-8 2050, Microchem) resulting in channels of rectangular cross section. A two layer microfluidic device was created using PDMS (Sylgard 184, Dow Corning). The top layer was cast using the injection mold, and aligned over a thin layer of partially cured PDMS which has been spun coat on the flow mold. After curing, devices were peeled from the molds and fluidic connections are punched with a flat luer stub adapter (BD Biosciences). Interconnects between the top and bottom fluid layers were created by small cuts with a scalpel. Injection and flow channels were 10 μm and 80 μm tall respectively, and both are 100 μm wide. Uniformity of all molds is ensured using a white light interferometer, and heights are found to vary by no more than approximately 1 μm over all channels. A plasma treatment was used to seal the ACEO substrates and PDMS caps, which were aligned and bonded under a microscope such that the 100 μm wide microchannels of rectangular cross section completely enclose the 80 μm wide plated pump structures. Complimentary grids on both the glass substrate and PDMS cap facilitated manual alignment within this tolerance. A representative microfabricated pump with electroplated steps and the microfluidic device is pictured in FIG. 21. FIG. 21(A) presents a scanning electron micrograph of the interdigitated fingers of a characteristic pump of the present study. FIG. 2(B) shows a photo micrograph of the lower half of the microfluidic experimental setup, including fluid control inputs and valve channels, and the gold ACEO pump.

Measurement Procedure

Fluid purging and metering operations are software controlled using micro-solenoids connected to the integrated MSL valves [Unger, supra]. Pressurized reservoirs of operating fluid (dilute potassium chloride), and a solution containing 1:250 tracers:water (v/v) are connected to the microfluidic device via tygon tubing. One input channel is used to load a solution of operating fluid in the loop, and the second input is used to inject flow markers (1.0 μm diameter fluorescent tracers, 505EX/515EM, Molecular Probes) in the corner of the pumping loop away from the electrodes to prevent interference due to electrophoresis or contamination of the pumps with particles [Studer, supra]. A signal generator (Agilent 3320A) is used to operate the ACEO pumps at various AC frequencies (0.5-10 kHz), at 3 V peak-to-peak (Vpp). Movies of the fluid far from the electrodes are recorded using a camera (Sony XCD-V50 B/W, 640×480 pixels) under an inverted fluorescent microscope with a 20× objective at each driving frequency in a similar manner for all pumps. The focal point of the microscope is set to the centerline of the microchannel to record the fastest moving particles. In order to achieve repeatable measurements and avoid any history effects on pumping, newly assembled devices were preconditioned for 60 minutes by pumping on fluid which did not contain beads. The pumping loop also was purged with fresh operating fluid prior to each measurement. Particle movies were analyzed using an open source particle image velocimetry code (URAPIV) through a MATLAB routine, which provided velocity measurements with less than 5% absolute error in calibration studies.

Numerical Methods

To allow for efficient numerical simulation, the electrodes were assumed to be sufficiently wide in the transverse direction for the problem to be effectively two-dimensional, and that the electrode array is sufficiently long to simulate a single electrode pair with periodic boundary conditions and ignore edge effects at the ends of the array.

The simple mathematical model used in previous simulations of ACEO pumps[A. Ramos, et al, J. Colloid Interface Sci. 217 (2) (1999), 420-422; A. Ajdari, Phys. Rev. E 61 (1) (2000), R45-R48., N. G. Green, et al., Phys. Rev. E 66 (2) (2002), 026305., L. H. Olesen, et al., Phys. Rev. E 73 (5) (2006), 056313., A. Ramos, et al., Phys. Rev. E 67 (5) (2003), 056302; B. P. Cahill, et al., Phys. Rev. E 70 (3) (2004), 036305; A. Ramos, et al., J. Appl. Phys. 97 (8) (2005), 084906; A. Gonzalez, et al., Phys. Rev. E 61 (4) (2000), 4019-4028, which are fully incorporated herein by reference)] and other phenomena of induced-charge electro-osmosis, which are justified for small voltages[A. Gonzalez, supra], $V \ll kT/e = 25$ mV.

ACEO experiments involve much larger voltages for which the theory becomes much more complicated. Nevertheless, the standard model has succeeded in capturing qualitative features of many experiments, thus it was used herein as a first approximation.

The first assumption for the simulations was that the double layers are thin enough to be treated as mathematical boundary layers surrounding a quasi-neutral bulk electrolyte, even during charging dynamics[M. Z. Bazant, et al, Phys. Rev. E 70 (2) (2004), 021506, fully incorporated herein by reference]. During nonlinear electrochemical relaxation in response to a large applied voltage, the bulk solution develops concentration gradients due to salt adsorption and tangential conduction by the double layers. Below a threshold voltage (a few times kT/e), however, it can be assumed that the bulk concentration (and conductivity) remain nearly uniform. In this limit, the bulk electrostatic potential satisfies Laplace's equation (Ohm's law), and the fluid velocity plays no role in the electrochemical dynamics, even with a large Peclet number. Neglecting Faradaic reactions, the double layer on each electrode acts like a capacitor with a constant capacitance in the linear regime of small voltages (<kT/e)] or a nonlinear differential capacitance at larger voltages, which depends on the specific model of the double layer. The non-electrode surfaces are assumed to be inert and non-polarizable. Typical flow velocities in ACEO experiments are on the order of a few millimeters per second. The fluid problem is therefore well into the incompressible, viscous flow regime, and the time-dependent Stokes equation can be employed. Use of the Helmholtz-Smoluchowski formula for determining induced-charge electro-osmotic slip velocity (outside the double layers) on the electrodes is assumed. Since the non-electrode surfaces are assumed to be non-polarizable, they can only permit linear fixed-charge electro-osmotic flows, which vanish upon time averaging, yielding effectively a no-slip condition.

For small voltages (<kT/e), the complete system of equations and boundary conditions is linear, so Gonzalez et al. [supra] and J. A. Levitan, et al, Colloids Surf, A 267 (1-3) (2005), 122-132, fully incorporated herein by reference) were followed in focusing on the steady sinusoidal response to a single-frequency AC voltage.

The electrostatic potential $\phi(x,y,t) = \text{Re}[\Phi(x,y)e^{i\omega t}]$, is expressed in terms of a time-independent complex-valued amplitude $\phi(x,y)$, which satisfies Laplace's equation:

$$\nabla^2 \Phi = 0 \qquad (1)$$

with the "RC" boundary condition at the electrode surfaces:

$$\hat{n} \cdot \nabla \Phi = \frac{i\omega \varepsilon_w \Lambda}{\sigma \lambda_D} (\Phi \pm V_{peak}) \qquad (2)$$

and an insulating boundary condition at the non-electrode surfaces:

$$\hat{n} \cdot \nabla \Phi = 0 \qquad (3)$$

Here $\varepsilon_w$ is the permissiivity of the solution, $\sigma$ is the electrical conductivity of the solution, $\lambda_D$ is the Debye length, and $\Lambda$ is the fraction of the total voltage across the double layer which is dropped across the diffuse layer (in the linear model). The latter is usually written as $\Lambda = (1+\delta)^{-1}$, where $\delta$ is the ratio of the diffuse-layer capacitance to the compact-layer capacitance.

Note that:

$$\tau_c = \frac{\varepsilon_w L \Lambda}{\sigma \lambda_D} = \frac{\lambda_D L \Lambda}{D} \quad (4)$$

is the natural "RC" time scale for charging of the double layers, where L is the geometrical length scale (usually the minimum feature size) and D is the typical ionic diffusivity.

The time-averaged fluid velocity is governed by the incompressible Stokes equations:

$$\nabla \cdot u = 0 \quad (5)$$

$$\nabla p = \eta \nabla^2 u \quad (6)$$

with no-slip conditions at non-electrode surfaces and the Helmholtz-Smoluchowski formula in the following form at the electrodes:

$$u_{\parallel} = \frac{\varepsilon_w \Lambda}{2\eta} \left( \frac{\text{Re}[\pm V_{peak} - \Phi]\text{Re}}{\left[\frac{\partial \Phi}{\partial x} + \text{Im}[+V_{peak} - \Phi]\text{Re}\left[\frac{\partial \Phi}{\partial x}\right]\right]} \right) \quad (7)$$

$$u_\perp = 0 \quad (8)$$

Where u is the time-averaged velocity field ($u_\parallel$ parallel and $u_\perp$ perpendicular to the electrode surface), p is the time-averaged pressure field, $\eta$ is the dynamic viscosity of the solution, and x is the coordinate along the electrodes.

Figure 22:
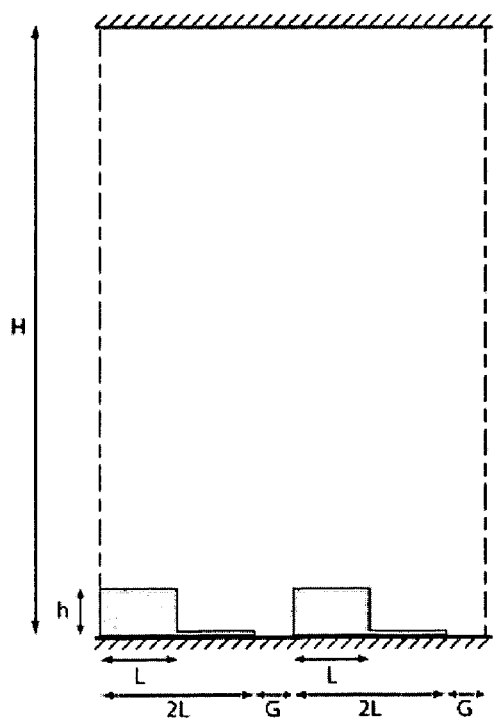
FIG. 22 schematically depicts the ACEO geometry used in the numerical model, with one complementary electrode pair located on an insulating substrate. The expected pumping direction is from left to right due to the FCB mechanism. The values of L, G and H in the present study are 10 mm, 5 mm and 80 mm, respectively. Periodic boundary conditions are imposed in the direction normal to the fluid flow, and no slip boundary conditions are imposed on the non-electrode surfaces. The heights of ACEO steps, h, range from 0 to 10 mm.

Simulations were completed using COMSOL Multiphysics 3.2b (COMSOL, Burlington, Mass.), a commercial program for performing electrical and hydrodynamic simulations using finite element methods, following methodologies previously described [Levitan, supra]. Each simulation used an automatically generated, triangular mesh and quadratic Lagrangian shape function. The mesh sizes were dependent on the exact geometry being studied; for the simulations for which results are presented herein, a typical mesh had approximately 35,000 elements and 1,000 boundary elements. Model dimensions and nomenclature are illustrated schematically in FIG. 22. The geometry was parametrically changed inside MATLAB scripts. Once the geometry was fixed, the mesh was automatically generated. The electrical problem was then solved and used as an input for solving the fluid system. Typical measures for pumping speed was the average value of the velocity (in the x-direction) along the periodic boundary of the system. It should be noted that even though the electrodes were relatively short, their sides (i.e. the step risers) must be treated as electrode surfaces, i.e. the double-layer capacitance model and the Helmholtz-Smoluchowski slip formula was applied on all sides of each in contact with the solution.

Results

It is clear from Eq. (2) that the appropriate non-dimensional frequency is scaled to the RC time, $$\Omega = \frac{\varepsilon_w \Lambda L}{\sigma \lambda_D} \omega \quad (9)$$

Similarly, Eq. (7) dictates that the velocity be scaled to the usual reference value for ICEO flows in the low-voltage model, $$U_{ref} = \frac{\varepsilon_w \Lambda V_{peak}^2}{\eta L} \quad (10)$$

Figure 23:
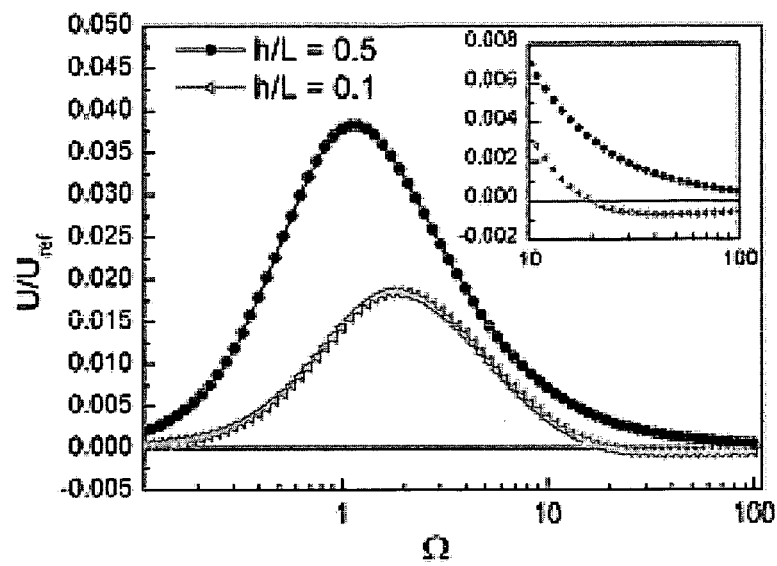
FIG. 23 plots the performance of pumps consisting of different step heights as a function of driving frequency. For moderate non-dimensional driving frequencies (W>>1), fast flows are developed as a result of the fluid conveyor belt principle. At high operating frequencies, negative pumping velocities, counter to the expected FCB mechanism, are observed for small values of h. The inset clarifies this flow reversal. If we fix L=0.2 (or d=4) for a 3 mM KCL solution, then the peak forward pumping in the figure occurs at 980 Hz. Moreover, if we fix the voltage at 3 Vpp, then the average outlet flow velocity at this frequency is 1.2 mm/s, which would correspond to 440 mm/s maximum velocity in the measurement loop, taking into account its hydraulic resistance.

Simulated data presented herein made use of these scales. The results of the parametric simulations for pumping velocities using two different step heights as a function of operating frequencies are presented in FIG. 23. The theoretical results for the maximum flow rate and peak frequency in the linear model were reasonably close to the corresponding experimental values, when $\Lambda=0.2$ or $\delta=4$, consistent with prior estimates of the degree to which the simplest theory (neglecting the compact layer) over-estimates the flow rate. The pumping performance for moderate (near optimal) and high (suboptimal) driving frequencies is summarized in FIG. 24 for a range of step heights. For large step heights, simulations were consistent with the results presented in the previous examples. For example, with h=0.5 L, the flow rate in FIG. 23 exhibited a single broad peak as a function of frequency consistent with "forward" flow due to the FCB mechanism. The peak frequency was at the expected scale of the characteristic RC charging frequency of the electrode geometry $\Omega \approx 1$. Thus, the flow rate of the non-planar 3D ACEO pumps was also much faster than that of standard planar designs with asymmetric flat electrode arrays, by more than an order of magnitude, for the same applied voltage and minimum feature size.

Figure 24:
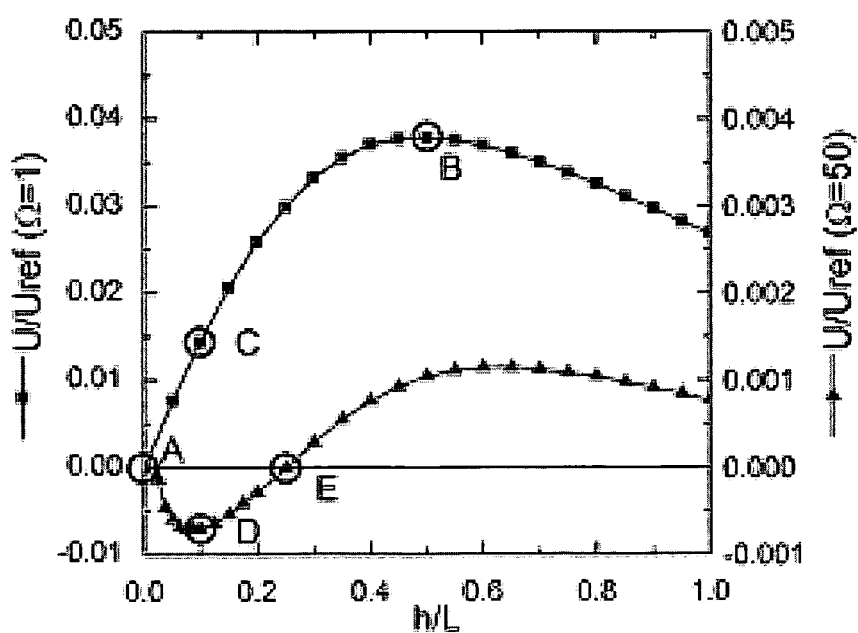
FIG. 24 plots the average fluid velocity computed across the outlet of the two-dimensional simulation as a function of electrode step height, for a high and low driving frequency. For moderate frequencies ($\Omega \gg 1$), idealized fluid conveyor belt pumping is observed for all h. Fluid streamlines and charging profiles developed in cases A and B are illustrated in FIGS. 25 (A) and (B). At high frequencies ($\Omega \ggg 10$), however, flow reversals are observed for low values of h. In these cases, charges are not able to screen across the entire electrode surfaces, and unexpected flow profiles are developed. At h/L>>0.1, for example, fluid flow may be switched from positive FCB pumping to reverse flow with a change of driving frequency. The streamlines in cases C and D provide further explanation in FIGS. 25 (C) and (D). Stagnation is also possible at higher frequencies. At point E, the partially developed vortices in the fluid conveyor belt are in balance with the smaller, but raised vortices on the top of the electrode steps. This case is illustrated in FIG. 25 (E).
Figure 25:
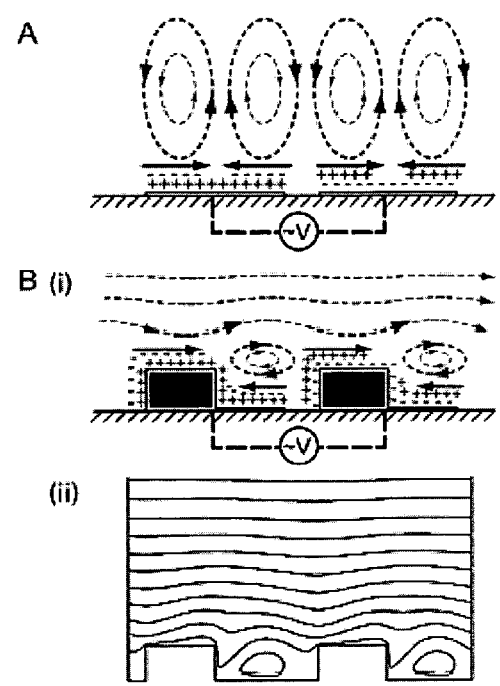
FIG. 25 is a schematic illustration of electrohydrodynamic profiles in cases A and B from FIG. 24. Surface slip and time averaged fluid streamlines are represented using solid and dashed arrows, respectively. At moderate frequencies, the double layer across the entire electrode is allowed to charge, and surface slip is fully developed. (A) If no steps are added to the symmetric electrodes (h=0), complementary vortices are sustained, and no directionality is possible. (B) (i) Charging dynamics are sketched alongside (ii) numerical fluid streamlines. For tall steps (h>>5 mm), the ideal fluid conveyor belt is developed.

The simulations also indicated that the fast flow rate was not very sensitive to the precise step height in the FCB regime, as shown in FIG. 24 for $\Omega \approx 1$. The frequency spectrum for fast pumping with large steps is easily understood in terms of the usual theoretical picture of ACEO flows, illustrated in FIGS. 25(A) and (B): At low frequencies $\Omega \ll 1$, the double layers have enough time within each AC period to become so charged as to fully screen the electric field, resulting in no electro-osmotic slip; at high frequencies $\Omega \gg 1$, there is not enough time for the double-layers to charge enough to contribute a significant voltage drop to the zeta potential, and hence there is also no slip. The peak at the RC frequency corresponds to a resonance where, in each period, the electrode double layers become partially charged near the edges, while leaving the central regions uncharged as sources of tangential electric field to drive induced electro-osmotic slip over the charged regions.

For smaller step heights, however, a more complicated frequency response was observed. The standard linear model for ACEO flow predicted some degree of flow reversal for non-planar pumps. FIG. 24, for $\Omega=50$ simulations at high frequencies predicted reverse flows for small step heights, which were almost as fast as the forward flows resulting from the FCB mechanism for large step heights.

Figure 26:
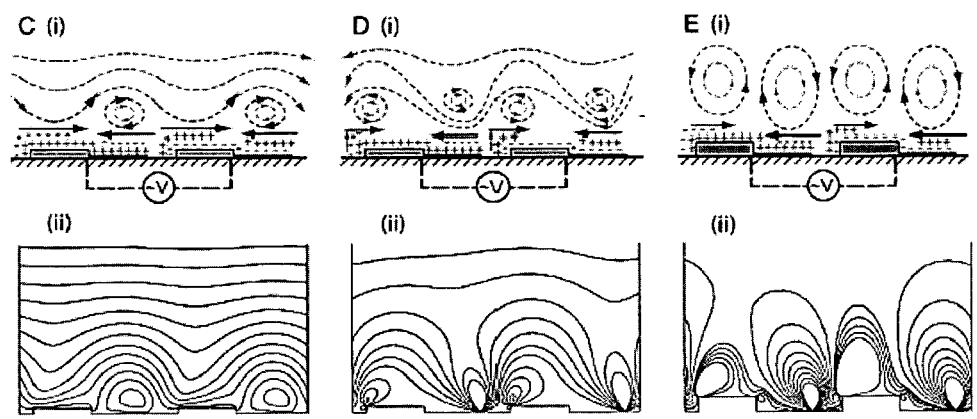
FIG. 26 schematically depicts the electrohydrodynamic profiles in cases C, D and E from FIG. 24—(i) charging dynamics are sketched alongside (ii) numerical fluid streamlines. Surface slip and time averaged fluid streamlines are represented using solid and dashed arrows, respectively. (C) At moderate frequencies, the double layer across the entire electrode is allowed to charge, and FCB pumping can be developed even for low step heights (h/L>>0.1). (D) For the same h/L, at high frequencies, only portions of the double layer near the strongest fields are allowed to charge. Surface slip on the low electrode portion develops more quickly than that on the step surface due to the geometry. As such, negative pumping is developed counter to the FCB mechanism. (E) An appropriate driving frequency at low step heights can also result in a balance between counter vortices on the non-planar electrodes. While the surface slip is further developed on the lower electrode surfaces, the smaller vortices are compensated by the step height, and no net pumping is achieved.
Figure 27:
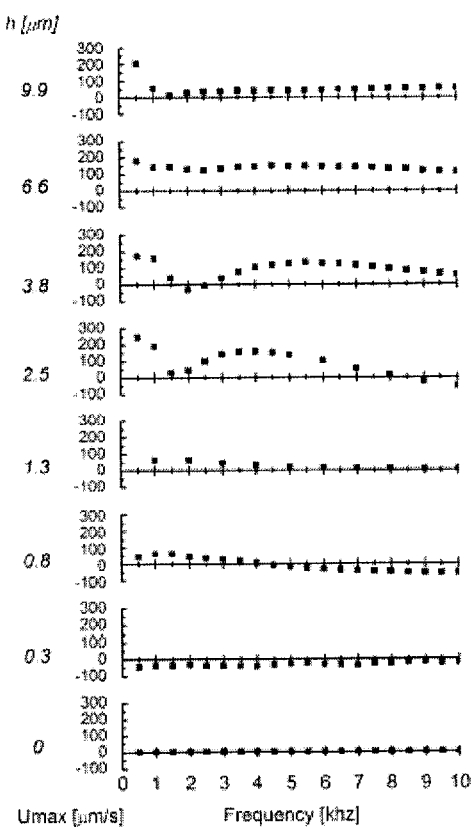
FIG. 27 plots centerline fluid velocity measured within microfluidic loops as a function of operating frequency using seven different 3D ACEO pumps. Positive velocity measurements are consistent with the fluid conveyor belt pumping mechanism of FIG. 21. Negative velocities are also observed for small submicron steps. The operating fluid is 3 mM KCl, and pumps are operated at 3 Vpp. The "double peaked" frequency response develops for intermediate step heights, and dampens out as the step height is further increased. At low frequencies, velocity response is difficult to predict, and between pumps of different step heights, peaks do not necessarily align at similar frequencies.

The mechanism for flow reversal at small step heights and high frequencies may, in some embodiments, be understood in terms of non-uniform charging dynamics in the non-planar electrode geometry, as illustrated in cases C and D of FIG. 26. At moderately high AC frequencies $\Omega \gg 1$, there was only enough time in each period for the double layers to charge close to the edges of the electrodes, where the normal electric field (prior to charging) was largest across the gap between the electrodes. In the non-planar geometry with asymmetric steps, the edges had different orientations, which affected the tangential electric field and the slip profile. The edge of the electrode step on the side of the raised surface (on the right of the gap) formed a shielded corner with a small tangential electric field, which reduces the slip compared to the lower electrode surface (on the left). Moreover, the vertical orientation of the step edge (on the right) led to slip which cannot pump in either direction, while the edge of the lower electrode surface (on the left) was horizontal and thus efficiently pumped away from the gap. The net effect was that the lower surface "won" in pumping in the reverse direction (to the left) for small step heights and high frequencies.

At lower frequencies near the optimum, more complete charging occurs across the electrodes, and the vertical edge contribution became insignificant, allowing the raised surface to win in pumping in the forward direction (to the right). Naturally, the balance of these two effects leads to an interesting case of zero flow at a special intermediate height and high frequency, in spite of a rather complicated flow profile, as shown in FIG. 26. sufficiently raised steps, any reverse flow on the lower surfaces tended to recirculate and help, rather than hinder, the forward flow from the raised surfaces.

Fluid velocity measurements were performed using a microfluidic device containing dilute KCl with a fixed 3 Vpp operating voltage. A range of driving frequencies from 0.5 to 10 kHz was applied. The experiments were performed with eight different ACEO devices, with step heights in the range of 0 μm (unplated) to 10 μm (plated). The pumps demonstrated complex velocity-frequency responses with increasing step height. Velocity measurements using a 3 μM KCl concentration are presented in FIG. 8. No directional pumping was evident without the addition of steps. With the addition of sub-micron steps on the electrodes, negative (reverse) pumping was observed at all frequencies. At higher plated step heights, the peak velocity—which was attained at lower frequencies—increased to a maximum at a height of around 3.8 μm and decreased up to 9.9 μm. Moreover, a "double peaked" frequency response was evident for intermediate step heights, although this effect dampened out as the step height is further increased.

Figure 28:
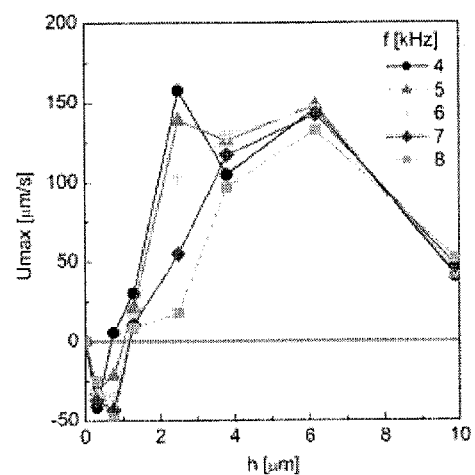
FIG. 28 plots centerline fluid velocity as a function of the ACEO electrode step height for various operating frequencies. The fluid is 3 mM KCl, pumped by an AC applied voltage 3 Vpp in the frequency range 4-8 kHz. Following from FIG. 27, peak velocities do not necessarily occur at similar driving frequencies for all pumps, and this frequency shifting results in a range of possible velocities for a given h. At large step heights the flow rate is strong, relatively insensitive to frequency and consistent with the fluid conveyor belt mechanism of FIG. 24. The data also shows relatively strong reverse flow at small, sub-micron step heights, which is not predicted by the simple linear model near the peak frequency. The simulations in FIG. 24 do predict a similar trend with height, but only at high frequencies far above the peak, where the flow rate is an order of magnitude smaller.

The individually-measured velocity-frequency spectrum curves were cross-sectioned to ascertain the effects of electrode step height on the average performance of the non-planar ACEO pumps. This data is presented in FIG. 28. The "double peaked" response contributes to velocity trends that overlap as h is increased across multiple frequencies. At high frequencies, greater than around 4 kHz, the velocity data as a function of height tended to collapse onto a single curve. A large spread in velocity measurements occurred for intermediate heights (h≈2-5 μm), in comparison to pumps with more conservative performance (h≈6-10 μm).

At low frequencies, velocity response was sensitive to driving frequency, particularly for pumps with steps in the range of ≈2-7 μm. Nonetheless, pumps with step heights in this intermediate range exhibited wide operating ranges, which were less sensitive to frequency, generally above 4 kHz.

For low step heights, very fast pumping may be achieved with tuning of the driving frequency. Taller pumps provided fast, steady pumping across a wide range of driving frequencies.

Pumps with large step heights exhibited robust, positive flow rates, in a direction consistent with the FCB mechanism. The shortest pump (h=0.3 μm) was not capable of pumping in the positive direction within the frequency range tested, however.

Conversely, the taller steps (h>≈6 μm) did not demonstrate flow reversal over the same frequency range. For electrode heights between 0.8 μm and 2.5 μm, however, transitions between forward and reverse flow occurred.

Thus systems designed with sufficiently low step heights may be used to pump fluid in both forward and reverse directions by appropriately tuning the driving frequency. This effect could be exploited to implement potentially useful bi-directional pumps in microfluidic devices.

The employed fabrication process used electroplating to create steps on the planar electrodes. Due to photolithography, however, the steps taper outwards with height as the 10 μm tall photoresist sidewalls were not perfectly vertical. The horizontal surface of the stepped electrodes also exhibited surface roughness due to the nature of electroplating (as observed in FIG. 21(a)). This is in contrast to the numerical model with straight and perpendicular electrode steps.

By applying only a few Volts at kHz frequencies, robust average velocities well over 100 μm/sec in a microfluidic loop only 25% covered by the electrode array (for measurement purposes) were demonstrated. Therefore, mm/s velocities at the same voltages should be attainable in practical devices more completely covered by pumping surfaces.

Such devices find many uses in lab-on-a-chip technology, especially in portable or implantable devices needing to operate at low power and low voltage, powered by a small battery.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device comprising at least one microfluidic chamber for conducting an electrolyte fluid or circulating an electrolyte fluid, or a combination thereof, said chamber comprising a plurality of stepped electrodes proximal to, or positioned on, a surface of said chamber, wherein at least two of said plurality of electrodes are connected to a source providing an electric field in said chamber and said electrodes or portions thereof are varied in height by at least 1% along flow direction in the region defined by the electrodes and with respect to said surface and whereby said plurality of electrodes are arranged so as to produce:
    electro-osmotic flows with at least one varied trajectory in a region of said chamber, resulting in mixing of said electrolyte fluid;
    a dominant electroosmotic flow which drives said electrolyte fluid across said chamber
    or a combination thereof.

2. The device of claim 1, wherein said electric field is comprised of a DC electric field.

3. The device of claim 1, wherein said electric field is comprised of an AC or pulsed AC electric field.

4. The device of claim 1, wherein said electrodes are parallel-positioned or interdigitated.

5. The device of claim 1, wherein said chamber is comprised of a transparent material.

6. The device of claim 1, further comprising at least one port for fluid entry into, egress from, or a combination thereof said device.

7. The device of claim 1, wherein said plurality of electrodes comprises at least one electrode, or a portion thereof, which is raised with respect to another electrode, or another portion of said at least one electrode.

8. The device of claim 1, wherein said plurality of electrodes comprises at least one electrode, or a portion thereof, which is lowered with respect to another electrode, or another portion of said at least one electrode.

9. The device of claim 1, wherein said plurality of electrodes comprises at least one electrode or at least a portion thereof having a height or depth, which is varied proportionally to a width of another electrode, another portion of said at least one electrode, or a combination thereof.

10. The device of claim 1, wherein said plurality of electrodes comprises at least one electrode, or portions thereof, having height or depth variations from about 1% to about 1000% of:
- a width of another electrode, another portion of said at least one electrode, or a combination thereof;
- a gap between said at least one electrode and another electrode;
- or a combination thereof.

11. The device of claim 1, wherein at least one electrode is not flat.

12. The device of claim 1, wherein at least one electrode comprises an edge, which is curved.

13. The device of claim 12, wherein said electrode comprises an edge, which forms a wavy or arc-like pattern, vertically, horizontally, or a combination thereof.

14. An apparatus comprising the device of claim 1.

15. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein said electric field is comprised of an AC or pulsed AC electric field with a DC offset.

16. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, said device comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof.

17. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1%, said device comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof, wherein said pumping element is held at a fixed potential, relative to that of said background electrodes.

18. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1%, said device comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof, wherein at least one electrode in said pumping element is grounded to one of said background electrodes.

19. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, said device comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof, wherein each electrode in said pumping element nearest to the background electrode connected to said source will have an opposite polarity as compared to said background electrode.

20. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof; and wherein an electrode in said pumping element is connected to the background electrode connected to said source, which is of the same polarity.

21. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, said device comprising:
- at least two background electrodes connected to said source, providing said electric field in said chamber; and
- at least one pumping element comprising two or more parallel-positioned or interdigitated electrodes positioned therebetween; wherein electrodes in said pumping element vary in height with respect to each other, said background electrodes, or a combination thereof, wherein electrodes in said pumping element are arranged asymmetrically with respect to a central axis in said pumping unit.

22. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein said electrodes are not co-axial, with respect to each other, in any dimension.

23. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof.

24. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof, wherein said electrodes are arranged in a symmetric pattern in said chamber.

25. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof, wherein said electrodes are arranged in a symmetric pattern in said chamber, wherein said gaps between said electrodes, said spacing of said electrodes, or a combination thereof is equal.

26. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof; and
wherein said electrodes are arranged in an asymmetric pattern in said chamber.

27. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof; and wherein said electrodes are arranged in an asymmetric pattern in said chamber, and wherein said gaps between said electrodes, said spacing of said electrodes, height of said electrodes or portions thereof, shapes of said electrodes or portions thereof, or a combination thereof is unequal.

28. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof; and
wherein said electrodes are arranged in a gradient pattern in said microfluidic channel.

29. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof, and wherein said gaps are between about 1 micron and about 50 microns.

30. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein positioning of said electrodes in said chamber is varied with respect to gaps between said electrodes, spacing of said electrodes, or a combination thereof, and wherein said electrode widths are between about 0.1 microns and about 50 microns.

31. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein at least one electrode comprises at least one raised portion of said electrode in the form of a cylinder of arbitrary cross section.

32. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein at least one electrode comprises an edge, which is straight and not parallel to another edge in said electrode or in another electrode.

33. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein at least one electrode comprises an edge, which is straight and not parallel to another edge in said electrode or in another electrode; and
wherein said electrode comprises an edge, which forms a chevron or sawtooth pattern, either vertically or horizontally.

34. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein at least one electrode comprises an exposed surface, which is flat, and not coplanar with another exposed surface of said electrode or of another electrode.

35. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface, wherein at least one electrode comprises an exposed surface, which is not flat, and arbitrarily curved in three dimensions.

36. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface; wherein said source applies a peak to peak AC voltage of between about 0.1 and about 10 Volts.

37. A device comprising at least one microfluidic chamber for conducting an electrolyte fluid or circulating an electrolyte fluid, or a combination thereof, said chamber comprising a plurality of electrodes proximal to, positioned on, or comprising a surface of said chamber, wherein at least two of said plurality of electrodes are connected to a source providing an electric field in said chamber and said electrodes or portions thereof are varied in height by at least 1% along flow direction and with respect to said surface; wherein said source applies a peak to peak AC voltage of between about 0.1 and about 10 Volts; wherein said AC frequency is between about 1 Hz and about 100 kHz.

38. A method of circulating or conducting a fluid, said method comprising applying a fluid to a device comprising at least one chamber comprising a plurality of stepped electrodes proximal to, or positioned on, a surface of said chamber, wherein at least two of said plurality of electrodes are connected to a source providing an electric field in said chamber and said electrodes or portions thereof are varied in height by at least 1% along flow direction in the region defined by the electrodes and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid.

39. The method of claim 38, wherein said plurality of electrodes comprises at least one electrode, or a portion thereof, which is lowered with respect to another electrode, or another portion of said at least one electrode.

40. The method of claim 38, wherein said electrodes are arranged in a symmetric pattern in said microfluidic channel.

41. The method of claim 38, wherein at least one electrode is not flat.

42. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, wherein said electric field is comprised of an AC or pulsed AC electric field.

43. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, wherein said plurality of electrodes comprises at least one electrode, or a portion thereof, which is raised with respect to another electrode, or another portion of said at least one electrode.

44. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid; wherein said plurality of electrodes comprises at least one electrode or at least a portion thereof having a height or depth, which is varied proportionally to a width of another electrode, another portion of said at least one electrode, or a combination thereof.

45. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid;
wherein said plurality of electrodes comprises at least one electrode, or portions thereof, having height or depth variations from about 1% to about 1000% of:
a width of another electrode, another portion of said at least one electrode, or a combination thereof;
a gap between said at least one electrode and another electrode;
or a combination thereof.

46. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, and wherein positioning of said electrodes in said chamber is varied with respect to gaps between said electrodes, spacing of said electrodes, or a combination thereof.

47. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, and wherein said electrodes are arranged in an asymmetric pattern in said microfluidic channel.

48. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, and wherein said electrodes are arranged in a gradient pattern in said microfluidic channel.

49. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, said method further comprising assay or analysis of said fluid.

50. A method of circulating or conducting a fluid, said method comprising applying a fluid to a device comprising at least one chamber comprising a plurality of electrodes proximal to, positioned on, or comprising a surface of said chamber, wherein at least two of said plurality of electrodes are connected to a source, providing an electric field in said chamber and said electrodes or portions thereof are varied in height by at least 1% along flow direction and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, thereby circulating or conducting a fluid, said method further comprising reconstituting a compound in said device, upon application of said fluid.

51. A method of cellular analysis comprising the steps of:
a. introducing a buffered suspension comprising cells to a first port of a device;
b. introducing a reagent for cellular analysis to said first or to a second port of said device, said device comprising at least one chamber comprising a plurality of stepped electrodes proximal to, or positioned on, a surface of said chamber, wherein at least two of said plurality of electrodes are connected to a source, providing an electric field in said chamber and said electrodes or portions thereof are varied in height by at least 1% along flow direction in the region defined by the electrodes and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof; and c. analyzing at least one parameter affected by contact between said suspension and said reagent.

52. The method of claim 51, wherein said reagent is an antibody, a nucleic acid, an enzyme, a substrate, a ligand, or a combination thereof.

53. The method of claim 51, wherein said reagent is coupled to a detectable marker.

54. The method of claim 53, wherein said marker is a fluorescent compound.

55. The method of claim 54, wherein said device is coupled to a fluorimeter or fluorescent microscope.

56. The method of claim 54, further comprising the step of introducing a cellular lysis agent in said port.

57. The method of claim 56, wherein said reagent specifically interacts or detects an intracellular compound.

58. A method of high-throughput, multi-step product formation, the method comprising the steps of:
   a. introducing a first liquid comprising a precursor to a first port of a device;
   b. introducing a second liquid comprising a reagent, catalyst, reactant, cofactor, or combination thereof to said first port, or a second port of said device, said device comprising at least one chamber comprising a plurality of stepped electrodes proximal to, or positioned on, a surface of said chamber, wherein at least two of said plurality of electrodes are connected to a source, providing an electric field in said chamber and said electrodes or portions thereof are varied in height by at least 1% along flow direction in the region defined by the electrodes and with respect to said surface, whereby upon application of said electric field, electro-osmotic flows with at least one varied trajectory is generated in a region of said chamber, resulting in mixing of said electrolyte fluid; a dominant electroosmotic flow is generated, which drives said electrolyte fluid across said chamber, or a combination thereof, and a product of said precursor is formed in said device; and
   c. collecting said product from said device.

59. The method of claim 58, further comprising carrying out iterative introductions of said second liquid, as in (b), to additional ports.

60. The method of claim 58, wherein said reagent is an antibody, a nucleic acid, an enzyme, a substrate, a ligand, a reactant or a combination thereof.

61. A method of drug processing and delivery, the method comprising the steps of:
   a. introducing a drug and a liquid comprising a buffer, a catalyst, or combination thereof to a device, comprising at least one chamber comprising a plurality of stepped electrodes proximal to, or positioned on, a surface of said chamber, wherein at least two of said plurality of electrodes are connected to a source, providing an electric field in said chamber and said electrodes or portions thereof are varied in height by at least 1% along flow direction in the region defined by the electrodes and with respect to said surface, whereby upon application of said electric field, electro-osmotic flows with at least one varied trajectory is generated in a region of said chamber, resulting in mixing of said electrolyte fluid comprising said drug; a dominant electroosmotic flow is generated, which drives said electrolyte fluid comprising said drug across said chamber, or a combination thereof; and
   b. collecting said drug, delivering said drug to a subject, or a combination thereof.

62. The method of claim 61, further comprising carrying out iterative introductions of a liquid to said device.

63. The method of claim 61, wherein introduction of said liquid serves to dilute said drug to a desired concentration.

64. A method of analyte detection or assay, comprising the steps of:
   a. introducing a first fluid comprising an analyte to a first port of a microfluidic device;
   b. introducing a second fluid comprising a reagent to said first port or to a second port of said microfluidic device, said microfluidic device comprising at least one chamber comprising a plurality of stepped electrodes proximal to, or positioned on, a surface of said chamber, wherein at least two of said plurality of electrodes are connected to a source, providing an electric field in said chamber and said electrodes or portions thereof are varied in height by at least 1% along flow direction in the region defined by the electrodes and with respect to said surface, whereby upon application of said electric field, electro-osmotic flows with at least one varied trajectory is generated in a region of said chamber, resulting in mixing of said fluid comprising said analyte and reagent; a dominant electroosmotic flow is generated, which drives said electrolyte fluid comprising said analyte and reagent across said chamber, or a combination thereof; and
   c. detecting, analyzing, or a combination thereof, of said analyte.

* * * * *